United States Patent
Davis et al.

(10) Patent No.: US 9,956,418 B2
(45) Date of Patent: May 1, 2018

(54) GRAPHICAL MANIPULATION OF POSTURE ZONES FOR POSTURE-RESPONSIVE THERAPY

(75) Inventors: Jon P. Davis, St. Michael, MN (US); Rajeev M. Sahasrabudhe, Maple Grove, MN (US); David Simons, Oakdale, MN (US)

(73) Assignee: Medtronic, Inc., Minneapolis, MN (US)

( * ) Notice: Subject to any disclaimer, the term of this patent is extended or adjusted under 35 U.S.C. 154(b) by 396 days.

(21) Appl. No.: 12/986,039

(22) Filed: Jan. 6, 2011

(65) Prior Publication Data
US 2011/0172738 A1   Jul. 14, 2011

Related U.S. Application Data
(60) Provisional application No. 61/293,555, filed on Jan. 8, 2010.

(51) Int. Cl.
*A61N 1/372* (2006.01)
*A61B 5/00* (2006.01)
(Continued)

(52) U.S. Cl.
CPC ........ *A61N 1/37247* (2013.01); *A61B 5/0031* (2013.01); *A61B 5/1116* (2013.01);
(Continued)

(58) Field of Classification Search
CPC ............ A61N 1/1116–1/1118; A61N 1/36535
(Continued)

(56) References Cited

U.S. PATENT DOCUMENTS

| 4,297,685 A | 10/1981 | Brainard, II |
| 4,365,633 A | 12/1982 | Loughman |

(Continued)

FOREIGN PATENT DOCUMENTS

| DE | 19831109 | 1/2000 |
| DE | 10024103 | 11/2001 |

(Continued)

OTHER PUBLICATIONS

International Search Report and Written Opinion for corresponding PCT Application No. PCT/US2011/020554, dated Feb. 18, 2011, (12 pgs.).

(Continued)

*Primary Examiner* — Joseph Dietrich
(74) *Attorney, Agent, or Firm* — Shumaker & Sieffert, P.A.

(57) ABSTRACT

The disclosure provides a system that displays graphical representations of posture zones associated with posture states of a patient, on a display device communicatively coupled to a medical device. The medical device is configured to deliver therapy to the patient based on detected posture states of the patient, where the detected posture state is based on the posture zones. The display device may allow a user to manipulate the graphical representations of the posture zones, including changing the size of the posture zones. Additionally, the display device may allow a user to change transition times associated with transitions between posture states, and displaying an indication of the changed transition time by highlighting the two graphical representations of the posture zones corresponding to the posture states associated with the changed transition time.

49 Claims, 24 Drawing Sheets

(51) Int. Cl.
*A61B 5/11* (2006.01)
*G06F 19/00* (2018.01)
*A61N 1/36* (2006.01)
*A61N 1/365* (2006.01)

(52) U.S. Cl.
CPC .......... *A61B 5/1117* (2013.01); *A61B 5/4839* (2013.01); *G06F 19/3418* (2013.01); *G06F 19/3468* (2013.01); *A61B 5/1118* (2013.01); *A61B 5/686* (2013.01); *A61B 5/744* (2013.01); *A61B 2560/0219* (2013.01); *A61N 1/36071* (2013.01); *A61N 1/36535* (2013.01); *A61N 1/37264* (2013.01); *A61N 1/37282* (2013.01)

(58) Field of Classification Search
USPC ...................................................... 607/17–20
See application file for complete search history.

(56) References Cited

U.S. PATENT DOCUMENTS

| | | |
|---|---|---|
| 4,543,955 A | 10/1985 | Schroeppel |
| 4,550,736 A | 11/1985 | Broughton et al. |
| 4,566,456 A | 1/1986 | Koning et al. |
| 4,771,780 A | 9/1988 | Sholder |
| 4,776,345 A | 10/1988 | Cohen et al. |
| 4,846,180 A | 7/1989 | Buffet |
| 4,846,195 A | 7/1989 | Alt |
| 5,031,618 A | 7/1991 | Mullett |
| 5,040,534 A | 8/1991 | Mann et al. |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,158,078 A | 10/1992 | Bennett et al. |
| 5,167,229 A | 12/1992 | Peckham et al. |
| 5,233,984 A | 8/1993 | Thompson |
| 5,275,159 A | 1/1994 | Griebel |
| 5,312,446 A | 5/1994 | Holschbach et al. |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,469,861 A | 11/1995 | Piscopo et al. |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A | 1/1997 | Sheldon |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,044,297 A | 3/2000 | Sheldon et al. |
| 6,083,475 A | 3/2000 | Sikorski et al. |
| 6,045,513 A | 4/2000 | Stone et al. |
| 6,059,576 A | 5/2000 | Brann |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,152,890 A | 11/2000 | Kupfer et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend |
| 6,853,863 B2 | 2/2005 | Carter et al. |
| 6,878,121 B2 | 4/2005 | Krausman et al. |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |

(56) References Cited

U.S. PATENT DOCUMENTS

| | | |
|---|---|---|
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Temes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |
| 7,082,333 B1 | 7/2006 | Bauhahn |
| 7,092,759 B2 | 8/2006 | Nehls et al. |
| 7,095,424 B2 | 8/2006 | Satoh et al. |
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 | 12/2006 | Koh et al. |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |
| 7,210,240 B2 | 5/2007 | Townsend et al. |
| 7,212,862 B2 | 5/2007 | Park et al. |
| 7,214,197 B2 | 5/2007 | Prass |
| 7,218,964 B2 | 5/2007 | Hill et al. |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 | 2/2008 | Heruth et al. |
| 7,366,569 B2 | 4/2008 | Belalcazar |
| 7,366,572 B2 | 4/2008 | Heruth et al. |
| 7,387,610 B2 | 6/2008 | Stahmann |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,664,546 B2 | 2/2010 | Hartley et al. |
| 7,672,806 B2 | 3/2010 | Tronconi |
| 7,717,848 B2 | 5/2010 | Heruth et al. |
| 7,769,464 B2 | 8/2010 | Gerber et al. |
| 7,792,583 B2 | 9/2010 | Heruth et al. |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0151824 A1 | 10/2002 | Fischer |
| 2002/0165586 A1 | 11/2002 | Hill et al. |
| 2002/0169485 A1 | 11/2002 | Pless et al. |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2004/0015103 A1 | 1/2004 | Aminian et al. |
| 2004/0049132 A1 | 3/2004 | Barron et al. |
| 2004/0088020 A1 | 5/2004 | Condie et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2005/0042589 A1 | 2/2005 | Hatlestad et al. |
| 2005/0043767 A1 | 2/2005 | Belalcazar |
| 2005/0060001 A1 | 3/2005 | Singhal et al. |
| 2005/0061320 A1 | 3/2005 | Lee et al. |
| 2005/0113710 A1 | 5/2005 | Stahmann et al. |
| 2005/0113887 A1 | 5/2005 | Bauhahn |
| 2005/0126026 A1 | 6/2005 | Townsend et al. |
| 2005/0137627 A1 | 6/2005 | Koshiol et al. |
| 2005/0145246 A1 | 7/2005 | Hartley et al. |
| 2005/0172311 A1 | 8/2005 | Hjelt et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245988 A1* | 11/2005 | Miesel ............ A61B 5/0205 607/46 |
| 2005/0270163 A1 | 12/2005 | Littell |
| 2005/0283210 A1 | 12/2005 | Blischak et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0206167 A1 | 9/2006 | Flaherty et al. |
| 2006/0212080 A1 | 9/2006 | Hartley et al. |
| 2006/0213267 A1 | 9/2006 | Tronconi et al. |
| 2006/0235289 A1 | 10/2006 | Wesselink et al. |
| 2006/0235472 A1 | 10/2006 | Goetz et al. |
| 2006/0241513 A1 | 10/2006 | Hatlestad et al. |
| 2006/0247732 A1 | 11/2006 | Wesselink |
| 2006/0247739 A1 | 11/2006 | Wahlstrand et al. |
| 2006/0259099 A1 | 11/2006 | Goetz et al. |
| 2006/0262120 A1 | 11/2006 | Rosenberg |

(56) References Cited

U.S. PATENT DOCUMENTS

| | | |
|---|---|---|
| 2006/0265025 A1 | 11/2006 | Goetz et al. |
| 2006/0287686 A1 | 12/2006 | Cullen et al. |
| 2007/0015976 A1 | 1/2007 | Miesel et al. |
| 2007/0038265 A1 | 2/2007 | Tcheng et al. |
| 2007/0050715 A1 | 3/2007 | Behar |
| 2007/0073355 A1 | 3/2007 | DiLorenzo et al. |
| 2007/0115277 A1 | 5/2007 | Wang et al. |
| 2007/0118056 A1 | 5/2007 | Wang et al. |
| 2007/0123758 A1 | 5/2007 | Miesel et al. |
| 2007/0129622 A1 | 6/2007 | Bourget et al. |
| 2007/0129641 A1 | 6/2007 | Sweeney |
| 2007/0129769 A1 | 6/2007 | Bourget et al. |
| 2007/0129774 A1 | 6/2007 | Bourget et al. |
| 2007/0150026 A1 | 6/2007 | Bourget et al. |
| 2007/0150029 A1 | 6/2007 | Bourget et al. |
| 2007/0213789 A1 | 9/2007 | Nolan et al. |
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0255154 A1 | 11/2007 | Lu et al. |
| 2007/0265664 A1 | 11/2007 | Gerber et al. |
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0079444 A1 | 4/2008 | Denison |
| 2008/0081958 A1 | 4/2008 | Denison et al. |
| 2008/0114219 A1 | 5/2008 | Zhang et al. |
| 2008/0164979 A1 | 7/2008 | Otto |
| 2008/0177355 A1 | 7/2008 | Miesel et al. |
| 2008/0188901 A1 | 8/2008 | Sanghera et al. |
| 2008/0188909 A1 | 8/2008 | Bradley |
| 2008/0194998 A1 | 8/2008 | Holmstrom et al. |
| 2008/0204255 A1 | 8/2008 | Flexer et al. |
| 2008/0269812 A1 | 10/2008 | Gerber et al. |
| 2008/0269843 A1 | 10/2008 | Gerber |
| 2008/0281376 A1 | 11/2008 | Gerber et al. |
| 2008/0281379 A1 | 11/2008 | Wesselink |
| 2008/0281381 A1 | 11/2008 | Gerber et al. |
| 2008/0288200 A1 | 11/2008 | Noble |
| 2008/0300449 A1 | 12/2008 | Gerber et al. |
| 2008/0300470 A1 | 12/2008 | Gerber et al. |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | Kristofer et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0137933 A1 | 5/2009 | Lieberman et al. |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0270747 A1 | 10/2009 | van Dam et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0030286 A1 | 2/2010 | Goetz et al. |
| 2010/0121415 A1 | 5/2010 | Skelton et al. |
| 2010/0174155 A1 | 7/2010 | Heruth et al. |

FOREIGN PATENT DOCUMENTS

| | | |
|---|---|---|
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1331022 A2 | 7/2003 |
| EP | 1391846 | 2/2004 |
| EP | 1437159 | 7/2004 |
| EP | 1731088 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/87433 | 11/2002 |
| WO | 02/96512 | 12/2002 |
| WO | 02/100267 | 12/2002 |
| WO | 03/51356 | 6/2003 |
| WO | 03/65891 | 8/2003 |
| WO | 05/28029 | 3/2005 |
| WO | 05/35050 | 4/2005 |
| WO | 05/79487 | 9/2005 |
| WO | 05/89646 | 9/2005 |
| WO | 05/89647 | 9/2005 |
| WO | 05/89860 | 9/2005 |
| WO | 05/102499 | 11/2005 |
| WO | 05/120348 | 12/2005 |
| WO | 07/09088 | 1/2007 |
| WO | 07/51196 | 5/2007 |
| WO | 07/64682 | 6/2007 |
| WO | 07/64936 | 6/2007 |
| WO | 08/26970 | 3/2008 |

OTHER PUBLICATIONS

Muhannad Quwaider, Subir Biswas: "Body Posture Identification using Hidden Markov Model with a Wearable Sensor Network," Bodynets '08 Proceedings of the ICST 3rd International Conference on Body Area Networks, XP002632420, 2008 (8 pgs.).

"Analysis of heart rate dynamics by methods derived from non-linear mathematics: Clinical applicability and prognostic significance," http://herkules.oulu.fi.isbn9514250133/html, 4 pp., 2004.

(56) References Cited

OTHER PUBLICATIONS

"Design Competition: Runners-Up for the Best Three Designs," EPN, vol. 26, No. 1, 1 pg., 2002.
"IBM and Citizen Watch develop Linux-Based WatchPad," http://wwwlinuxdevices.com/news/NS6580187845.html, 5 pp., 2006.
"MiniMitter® Physiological and Behavioral Monitoring for Humans and Animals," http://www.minimitter.com/Products/Actiwatch, 3 pp., 2006.
"Watch," Wikipedia, 6 pp., http://en.wikipedia.org/wiki/Watch, 2006.
Aminian et al., "Physical Activity Monitoring Based on Accelerometry: Validation and Comparison with Video Observation," Medical & Biological Engineering and Computing, vol. 37, No. 2, pp. 304-308,1999.
Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.
Ang et al., "Physical model of a MEMS accelerometer for low-g motion tracking applications," 2004 IEEE International Conference on Robotics and Automation, vol. 2, pp. 1345-1351, 2004.
Buchser et al., "Improved Physical Activity in Patients Treated for Chronic Pain by Spinal Cord Stimulation," Neuromodulation, vol. 8, Issue 1, pp. 40-48, Mar. 2005.
Crago et al., "An Elbow Extension Neuroprosthesis for Individuals with Tetraplegia," IEEE Transactions on Rehabilitation Engineering, vol. 6, No. 1, pp. 1-6, Mar. 1998.
Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.
Dinner, "Effect of Sleep on Epilepsy," Journal of Clinical Neurophysiology, American Clinical Neurophysiology Society, 19(6), pp. 504-513, 2002.
Foerster et al., "Motion Pattern and Posture: Correctly Assessed by Calibrated Accelerometers," Forschungsgrupe Psychophysiologie, Universität Freiburg, Germany, Mar. 2000, 28 pp.
Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.
Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.
Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.
Goodrich et al., "The Prediction of Pain Using Measures of Sleep Quality," Pain Digest, 8:23-25, 1998.
Heinz et al., "Using Wearable Sensors for Real-time Recognition Tasks in Games of Martial Arts—An Initial Experiment," Institute for Computer Systems and Networks (CSN), UMIT—University of Health Systems, Medical Informatics and Technology Hall in Tyrol, Austria, 2006 5 pp. http://eis.comp.lancs.ac.uk/fileadmin/relate/publication/2006-WearableSensors.pdf.
Hendelman et al., "Validity of Accelerometry for the Assessment of Moderate Intensity Physical Activity in the Field," Medicine & Science in Sports & Exercise, pp. S442-S449, 2000.
Hinckley, K., Pierce, J., Sinclair, M., Horvitz, E., *Sensing Techniques for Mobile Interaction,* ACM UIST 2000 Symposium on User Interface Software & Technology, CHI Letters 2 (2), pp. 91-100, 2000.
Husak, "Model of Tilt Sensor Systems, "ICECS 2002, 9$^{th}$ IEEE International Conference on Electronics, Circuits and Systems, vol. 1, pp. 227-230, 2002.
Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.
Kassam, "2005 EDP Topic "MK4": Tremor Data-Logger for Parkinson's Disease Patients," http://www.ee.ryerson.ca/~courses/edp2005/MK4.html, 3 pp., 2005.
Kerr et al., "Analysis of the sit-stand-sit movement cycle in normal subjects," Clinical Biomechanics, vol. 12, No. 4, pp. 236-245, 1977.
Kiani et al., "Computerized Analysis of Daily Life Motor Activity for Ambulatory Monitoring," Technology and Health Care 5, pp. 307-318, 1997.
Kitchin et al., "Compensating for the 0 g Offset Drift of the ADXL50 Accelerometer," Analog Devices Application Note AN-380, 2 pp, 1994.
Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.
Leiper et al., "Sensory Feedback for Head Control in Cerebral Palsy," Physical Therapy, vol. 61, No. 4, pp. 512-518, Apr. 1981.
Lorussi, "Wearable, Redundant Fabric-Based Sensor Arrays for Reconstruction of Body Segment Posture," IEEE Sensors Journal, vol. 4, No. 6, pp. 808-817, Dec. 2004.
Mathie et al., "A Pilot Study of Long-Term Monitoring of Human Movements in the Home Using Accelerometer," Journal of Telemedicine and Telecare10:144-151, Jun. 2007.
Mathie et al., "Determining Activity Using a Triaxial Accelerometer," Proceedings of the Second Joint EMBS/BMES Conference, Houston, TX, pp. 2481-2482, Oct. 23-26, 2002.
Mattmann et al., "Recognizing Upper Body Postures Using Textile Strain Sensors," Proceedings Eleventh IEEE International Symposium on Wearable Computers, ISWC, pp. 29-36, 2007.
Mendez et al., "Interactions Between Sleep and Epilepsy," Journal of Clinical Neurophysiology, American Clinical Neurophysiology Society, 18(2), pp. 106-127, 2001.
Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.
Slyper et al., "Action Capture with Accelerometers," Eurographics/ACM SIGGRAPH Symposium on Computer Animation, Carnegie Mellon University, 7 pp. 2008.
Smith et al., "How do sleep disturbance and chronic pain interrelate? Insights from the longitudinal and cognitive-behavioral clinical trials literature," Sleep Medicine Reviews, YSMRV 286, pp. 1-14, 2003.
Smith et al., "Presleep cognitions in Patients with Insomnia Secondary to Chronic Pain," Journal of Behavioral Medicine, vol. 24, No. 1, pp. 93-114, 2001.
Emmanuel Munguia Tapia, "Activity Recognition from Accelerometer Data for Videogame Applications," http://alumni.media.mit.edu/~emunguia/html/videogames.htm, 7 pp., Dec. 2, 2003, printed Oct. 1, 2009.
Trolier-Mckinstry et al., "Thin Film Piezoelectrics for MEMS," Journal of Electroceramics, v. 12, No. 1-2, pp. 7-17, Jan./Mar. 2004.
Tuck, "Implementing Auto-Zero Calibration Technique for Accelerometers," Freescale Semiconductor Application Note AN3447, 5 pp., Mar. 2007.
Tuisku, "Motor Activity Measured by Actometry in Neuropsychiatric Disorders," Department of Psychiatry, University of Helsinki, Helsinki, Finland, 115 pp., 2002.
Vega-Gonzalez, "Upper Limb Activity Monitoring," Arch Phys Med Rehabil, vol. 86, pp. 541-548, Mar. 2005.
Velten et al., "A New Three-Axis Accelerometer," Sensor '99—9$^{th}$ Int'l Traide Fair and Conference for Sensors/Transducers & Systems, Nurnberg, Germany, May 18-20, 1999, Sensor '99 Proceedings II, A 5.2, pp. 47-52, 1999.
http://eis.comp.lances.ac.uk/fileadmin/relate/publications/2006-WearableSensors.pdf.
U.S. Appl. No. 12/815,834, filed Jun. 15, 2010, Gerber et al.
U.S. Appl. No. 12/433,856, filed Apr. 30, 2009, Skelton et al.
U.S. Appl. No. 12/433,750, filed Apr. 30, 2009, Skelton et al.
U.S. Appl. No. 12/433,103, filed Apr. 30, 2009, Skelton et al.
U.S. Appl. No. 12/433,632, filed Apr. 30, 2009, Skelton et al.

(56) References Cited

OTHER PUBLICATIONS

U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,520, filed Apr. 30, 2009, Skelton.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.
U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.
U.S. Appl. No. 12/433,684, filed Apr. 30, 2009, Skelton et al.
U.S. Appl. No. 12/433,017, filed Apr. 30, 2009, Skelton et al.
U.S. Appl. No. 12/433,004, filed Apr. 30, 2009, Panken et al.
U.S. Appl. No. 12/548,227, filed Aug. 26, 2009, Skelton et al.
U.S. Appl. No. 12/433,038, filed Apr. 30, 2009, Panken.
U.S. Appl. No. 12/433,029, filed Apr. 30, 2009, Panken et al.
U.S. Appl. No. 12/432,993, filed Apr. 30, 2010, Panken et al.
U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.
U.S. Appl. No. 12/895,919, filed Jan. 6, 2011, Davis et al.
U.S. Appl. No. 61/293,393, filed Jan. 8, 2010, Davis et al.
U.S. Appl. No. 61/330,063, filed Apr. 30, 2010, Davis et al.
U.S. Appl. No. 61/293,538, filed Jan. 8, 2010, Davis et al.
U.S. Appl. No. 12/985,965, filed Jan. 6, 2011, Davis et al.
Search Report from counterpart European Application No. 11700221.2, dated Jan. 7, 2016, 6 pp.
Response to counterpart European Examination Report dated Jan. 7, 2016, from counterpart European Patent Application No. 11700221.2, filed on Jul. 18, 2016, 5 pp.
Communication pursuant to Article 94(3) EPC from counterpart European Application No. 11700221.2, dated Apr. 10, 2017, 5 pp.
Response to Examination Report dated Apr. 10, 2017, from counterpart European Application No. 11700221.2, filed Oct. 20, 2017, 4 pp.

* cited by examiner

GRAPHICAL MANIPULATION OF POSTURE ZONES FOR POSTURE-RESPONSIVE THERAPY

This application claims the benefit of U.S. Provisional Application No. 61/293,555, entitled "GRAPHICAL MANIPULATION OF POSTURE ZONES FOR POSTURE-RESPONSIVE THERAPY," filed on Jan. 8, 2010, the entire content of which is incorporated herein by reference.

TECHNICAL FIELD

The disclosure relates to medical devices and, more particularly, to programmable medical devices that deliver therapy.

BACKGROUND

A variety of medical devices may be used for chronic, e.g., long-term, delivery of therapy to patients suffering from a variety of conditions, such as chronic pain, tremor, Parkinson's disease, epilepsy, urinary or fecal incontinence, sexual dysfunction, obesity, or gastroparesis. One example of medical devices is medical electrical stimulation devices, which may deliver electrical stimulation therapy to a patient via implanted electrodes. Electrical stimulation therapy may include stimulation of nerve, muscle, or brain tissue, or other tissue within a patient.

An electrical stimulation device may be fully implanted within the patient. For example, an electrical stimulation device may include an implantable electrical stimulation generator and one or more implantable leads carrying electrodes. As examples, electrical stimulation generators are used for chronic delivery of electrical stimulation therapies such as cardiac pacing, neurostimulation, muscle stimulation, or the like. Alternatively, the electrical stimulation device may comprise a leadless stimulator. In some examples, implantable electrodes may be coupled to an external electrical stimulation generator via one or more percutaneous leads or fully implanted leads.

Other examples of medical devices are pumps or other fluid delivery devices, which may be used for chronic delivery of therapeutic agents, such as drugs. Typically, such devices provide therapy continuously or periodically according to parameters contained within a program. A program may comprise respective values for each of a plurality of parameters, specified by a clinician.

In some examples, the patient may be allowed to activate and/or modify the therapy delivered by the medical device. For example, a patient can be provided with a patient programming device. The patient programming device communicates with a medical device to allow the patient to activate therapy and/or adjust therapy parameters. For example, an implantable medical device (IMD), such as an implantable neurostimulator or a fluid delivery device, may be accompanied by an external patient programmer that permits the patient to activate and deactivate neurostimulation or fluid delivery therapy and/or adjust the intensity of the delivered neurostimulation or the delivered amount of the therapeutic agent. The patient programmer may communicate with the IMD via wireless telemetry to control the IMD and/or retrieve information from the IMD.

SUMMARY

In general, the disclosure describes techniques for presenting, to a user of an external device associated with an IMD, an avatar of a patient and graphical representation associated with zones corresponding to one or more postures, where the IMD delivers therapy to the patient based on a posture detected based on the zones. The user may manipulate parameters and settings associated with the therapy delivered by the IMD by manipulating the graphical representation associated with the zones. The external device may include a user interface that displays the avatar and the graphical representation of the zones to the user, allowing the user to set up and modify parameters associated with the zones corresponding to the postures of the patient represented by the avatar. The graphical representations may be displayed on the user interface to allow the user to graphically manipulate the posture zones and parameters. The external device may allow the user to manipulate the posture zones by re-sizing them and modify other parameters associated with the postures such as, the transition times used to determine whether a posture change has occurred.

In one example, the disclosure is directed to a programmer device for an implantable medical device comprising a display device that displays a graphical representation of posture zones associated with a patient on a display device, wherein the display device is communicatively coupled to a medical device, wherein the medical device is configured to deliver therapy to the patient based on a detected posture of the patient, and wherein the posture is detected based on the posture zones, a user interface that receives user input, wherein the user input comprises an indication to change one or more parameters associated with one or more of the posture zones, and a processor configured to change at least one of the posture zones in response to the user input.

In another example, the disclosure is directed to a method comprising displaying a graphical representation of posture zones associated with a patient on a display device, wherein the display device is communicatively coupled to a medical device, wherein the medical device is configured to deliver therapy to the patient based on a detected posture of the patient, and wherein the posture is detected based on the posture zones, receiving user input, wherein the user input comprises an indication to change one or more parameters associated with one or more of the posture zones, and changing at least one of the posture zones in response to the user input.

In another example, the disclosure is directed to a system comprising means for displaying a graphical representation of posture zones associated with a patient on a display device, wherein the display device is communicatively coupled to a medical device, wherein the medical device is configured to deliver therapy to the patient based on a detected posture of the patient, and wherein the posture is detected based on the posture zones, means for receiving user input, wherein the user input comprises an indication to change one or more parameters associated with one or more of the posture zones, and means for changing at least one of the posture zones in response to the user input.

In another example, the disclosure is directed to a computer-readable medium comprising instructions that, upon execution, cause a processor to display a graphical representation of posture zones associated with a patient on a display device, wherein the display device is communicatively coupled to a medical device, wherein the medical device is configured to deliver therapy to the patient based on a detected posture of the patient, and wherein the posture is detected based on the posture zones, receive user input, wherein the user input comprises an indication to change one or more parameters associated with one or more of the posture zones, and change at least one of the posture zones in response to the user input.

In another example, the disclosure is directed to a system comprising an implantable medical device configured to deliver therapy to a patient, a display device that displays a graphical representation of posture zones associated with a patient on a display device, wherein the display device is communicatively coupled to the implantable medical device, wherein the implantable medical device is configured to deliver therapy to the patient based on a detected posture of the patient, and wherein the posture is detected based on the posture zones, a user interface that receives user input, wherein the user input comprises an indication to change one or more parameters associated with one or more of the posture zones, and a processor configured to change at least one of the posture zones in response to the user input.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1A:
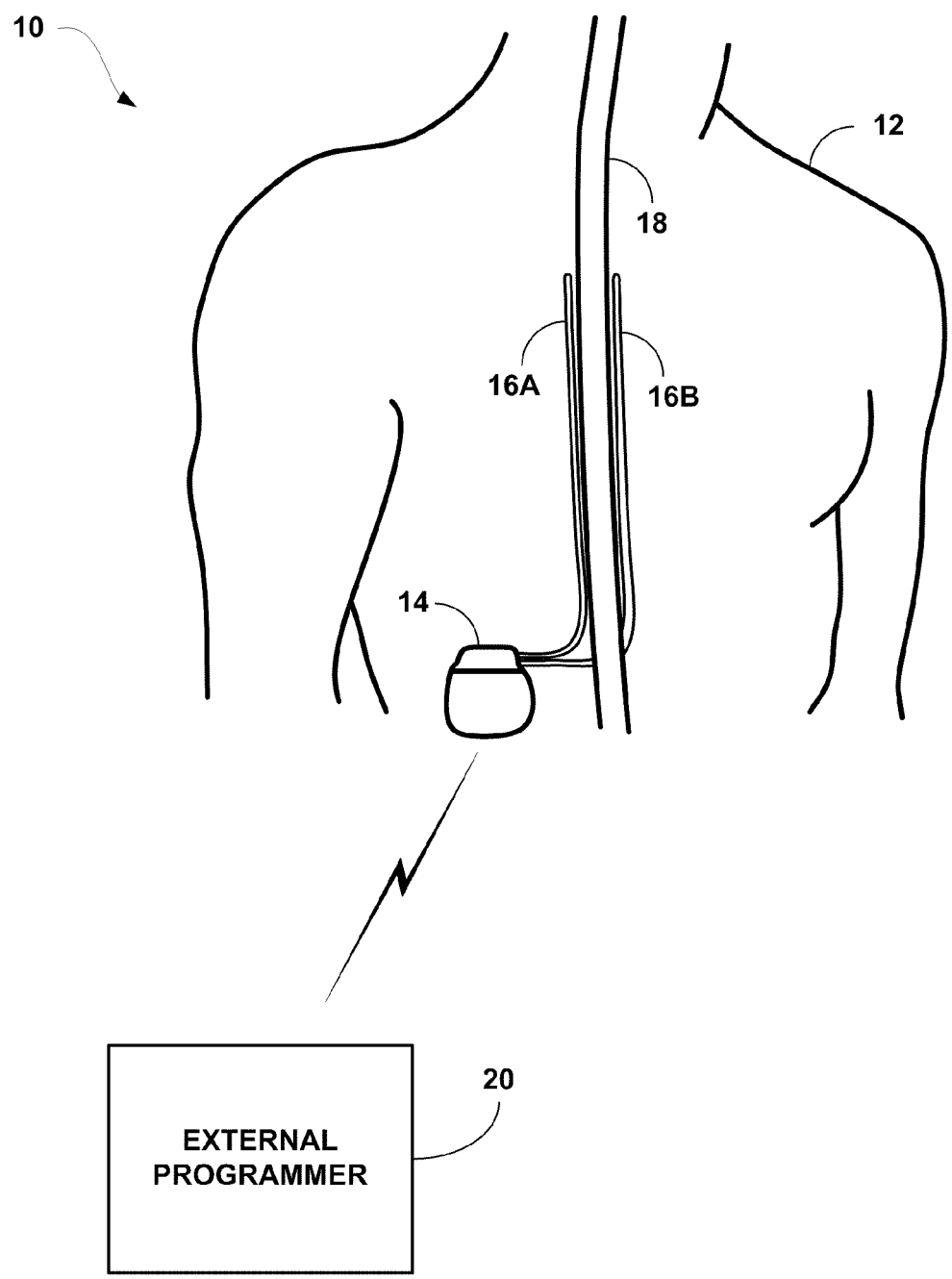
FIG. 1A is a conceptual diagram illustrating an example implantable stimulation system including two implantable stimulation leads.

A medical device may be configured to deliver therapy (e.g., electrical stimulation, therapeutic agent or drug, or the like) based upon a detected posture state of the patient. In such a medical device, posture state information may be used to automatically select therapy parameters to target certain symptoms or conditions that may change with different anatomical posture states. In the context of programming or evaluation of therapy, it may be useful for the clinician and/or patient to visualize how the medical device is detecting the posture state of the patient. The techniques described in this disclosure allow a user to configure and modify posture zones relative to an avatar of a patient, where the posture zones correspond to postures to be used in delivery of posture responsive therapy, and where an external device (e.g., a programmer device) associated with the medical device may display a graphical representation of the posture zones and the avatar to the user on a user interface.

A medical device may deliver one or more types of therapy to a patient, including electrical stimulation therapy and/or non-electrical stimulation therapy. An example of non-electrical stimulation therapy may include fluid delivery therapy. For purposes of illustration, the examples in this disclosure will be described with respect to the delivery of electrical stimulation therapy. However, it should be understood that, in some examples, similar principles may be applicable to the delivery of non-electrical stimulation therapy.

A medical device, such as an implantable medical device (IMD), may deliver electrical stimulation therapy to a patient for a variety of reasons. For example, an IMD may deliver electrical stimulation therapy to treat patients that suffer from chronic back pain, leg pain, movement disorders, epilepsy, or other conditions that cannot be effectively or efficiently treated through other methods. Generally, values for one or more stimulation parameters associated with the electrical stimulation therapy can be defined to treat one or more of the conditions experienced by a patient. However, as a patient changes posture states, which may include changes in posture and/or activity level, the stimulation therapy delivered by the IMD to the patient may have to be adjusted to maintain therapeutic efficacy.

In some examples, an IMD may detect changes in the posture state of a patient and automatically modify one or more parameters of the stimulation therapy being delivered to the patient based on the detected posture state change so as to achieve or maintain effective therapeutic results. When a patient transitions from an upright to a lying-down posture, for example, the IMD may adjust the stimulation amplitude value (e.g., voltage or current amplitude) from a value appropriate for the upright posture to a different value appropriate for the lying-down posture. In this example, the amplitude values for lying-down and upright postures may be different due to differences in effects of the stimulation, e.g., in terms of alleviation of symptoms, side effects, or both, when the patient occupies the different postures.

An IMD may detect the posture state of a patient by determining posture sensor data using information provided by a posture state module in the IMD. The posture sensor data may define a three-dimensional reference coordinate vector and a range of coordinates within a predetermined distance from the reference coordinate vector. In such an example, the posture state reference data may, in effect, define a posture volume or zone, such as, e.g., a posture cone. While this disclosure discusses posture cones, it should be understood that cones are discussed for purposes of illustration, and posture zones may be defined by any one of different volumetric shapes, e.g., cylinders, spheres, toroid, or the like.

As noted above, the posture zones may be represented using cones. Using the example of a posture cone, the cone and the range of vector coordinates within the cone may be defined in a variety of ways. For example, the posture cone may be defined by a distance or angle relative to a reference coordinate vector (e.g., an angle based on a center vector passing through the tip of the cone and the center of the base of the cone). As an alternative, a range of cosine values may define vectors within the cone in the sense that a cosine value computed for each of the vectors in the cone and the reference coordinate vector falls within the range of cosine values.

In an example, a set of default posture zones may not be appropriate for the therapy or the particular patient with which it is associated. As a result, a user (e.g., a clinician) may want to have the ability to resize posture zones. Additionally, a user may want to modify parameters associated with detecting transitions from one posture to another, by modifying, for example, the transition time required to set a detected posture as the current posture and apply the appropriate therapy for the current posture. In particular, the transition time may specify a minimum time for which the patient occupies a newly detected posture before the newly detected posture is accepted as the current posture for purposes of posture-responsive therapy.

If the posture sensor data falls within the range of coordinates defined by a set of the posture state reference data, the IMD determines that the patient occupies the posture state associated with that set of posture state reference data. Different posture states may be associated with different sets of posture state reference data. If the coordinates indicated by posture sensor data falls within the range of posture coordinates specified by the posture state reference data corresponding to an upright posture state, for example, then the IMD may detect that the patient is in the upright posture state. The posture sensor data may be compared to multiple sets of posture state reference data until a matching posture state is detected.

In accordance with this disclosure, in some examples, an external device (e.g., a programmer device) may be used to set up parameters and zones associated with postures of a patient, which may be displayed on a user interface to allow the user to graphically manipulate the posture zones and parameters associated therewith. The external device may allow the user to manipulate the posture zones by re-sizing them to define posture states, as will be described in more detail below. The user may manipulate other parameters associated with the posture states such as, for example, the transition times used to determine whether a posture change has occurred.

FIG. 1A is a schematic diagram illustrating an implantable stimulation system 10 including a pair of implantable electrode arrays in the form of stimulation leads 16A and 16B. Although the techniques described in this disclosure may be generally applicable to a variety of medical devices including external and implantable medical devices (IMDs), application of such techniques to IMDs and, more particularly, implantable electrical stimulators, such as neurostimulators, will be described for purposes of illustration. More particularly, the disclosure will refer to an implantable spinal cord stimulation (SCS) system for purposes of illustration, but without limitation as to other types of medical devices. In some examples, the stimulator may be an external stimulator used for screening therapy prior to implant.

As shown in FIG. 1A, system 10 includes an IMD 14 and external programmer 20 shown in conjunction with a patient 12, who is ordinarily a human patient. In the example of FIG. 1A, IMD 14 is an implantable electrical stimulator that delivers SCS, e.g., for relief of chronic pain or other symptoms. Again, although FIG. 1A shows an IMD, other examples may include an external stimulator, e.g., with percutaneously-implanted leads. Stimulation energy is delivered from IMD 14 to spinal cord 18 of patient 12 via one or more electrodes of implantable leads 16A and 16B (collectively "leads 16"). In some applications, such as spinal cord stimulation (SCS) to treat chronic pain, the adjacent implantable leads 16 may have longitudinal axes that are substantially parallel to one another.

Although FIG. 1A is directed to SCS therapy, system 10 may alternatively be directed to any other condition that may benefit from stimulation therapy. For example, system 10 may be used to treat tremor, Parkinson's disease, epilepsy, urinary or fecal incontinence, pelvic pain, sexual dysfunction, obesity, gastroparesis, or psychiatric disorders (e.g., depression, mania, obsessive compulsive disorder, anxiety disorders, and the like). In this manner, system 10 may be configured to provide therapy taking the form of deep brain stimulation (DBS), peripheral nerve stimulation, pelvic floor stimulation, gastric stimulation, or any other stimulation therapy.

Each of leads 16 may include electrodes (not shown in FIG. 1A), and the parameters for a program that controls delivery of stimulation therapy by IMD 14 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms such as, for example, substantially continuous waveforms. Programs that control delivery of other therapies by IMD 14 may include other parameters, e.g., such as dosage amount, rate, or the like for drug delivery.

In the example of FIG. 1A, leads 16 carry one or more electrodes that are placed adjacent to the target tissue of the spinal cord. One or more electrodes may be disposed at a distal tip of a lead 16 and/or at other positions at intermediate points along the lead. Leads 16 may be implanted and coupled to IMD 14. Alternatively, as mentioned above, leads 16 may be implanted and coupled to an external stimulator, e.g., through a percutaneous port. In some examples, an external stimulator may be a trial or screening stimulation used on a temporary basis to evaluate potential efficacy to aid in consideration of chronic implantation for a patient. In some examples, IMD 14 may be a leadless stimulator with one or more arrays of electrodes arranged on a housing of the stimulator in addition to or instead of leads that extend from the housing.

IMD 14 delivers electrical stimulation therapy to patient 12 via selected combinations of electrodes carried by one or both of leads 16. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1A, the target tissue is tissue proximate to spinal cord 18, such as within an intrathecal space or epidural space of spinal cord 18, or, in some examples, adjacent nerves that branch off of spinal cord 18. Leads 16 may be introduced into spinal cord 18 via any suitable region, such as the thoracic, cervical, or lumbar regions. Stimulation of spinal cord 18 may, for example, prevent pain signals from traveling through the spinal cord and to the brain of the patient. Patient 12 may perceive the interruption of pain signals as a reduction in pain and, therefore, efficacious therapy results.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns). Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead.

In the example of FIG. 1A, stimulation energy is delivered by IMD 14 to spinal cord 18 to reduce the amount of pain perceived by patient 12. As described above, IMD 14 may be used with a variety of different therapies, e.g., for pain or other symptoms or disorders, such as peripheral nerve stimulation (PNS), peripheral nerve field stimulation (PNFS), DBS, cortical stimulation (CS), pelvic floor stimulation, gastric stimulation, or the like. The electrical stimulation delivered by IMD 14 may take the form of electrical stimulation pulses or substantially continuous stimulation waveforms, and may be characterized by controlled voltage levels or controlled current levels, as well as pulse width and pulse rate in the example of stimulation pulses.

In some examples, IMD 14 may deliver stimulation therapy according to one or more programs. A program defines one or more stimulation parameters, which define an aspect of the therapy delivered by IMD 14 according to that program. For example, a program that controls delivery of stimulation by IMD 14 in the form of pulses may define one or more therapy parameters such as a voltage or current pulse amplitude, a pulse width, a pulse rate, for stimulation pulses delivered by IMD 14 according to that program. Moreover, therapy may be delivered according to multiple programs, wherein each program may target a different symptom or pain area. In some examples, multiple programs may be contained within each of a plurality of groups. In another example, separate programs may be selected for a set of program slots. Each slot may include one or more programs that form therapy options for the slot, and each slot may target a different symptom or area of pain. One program may be selected from each slot, where the selection of a program in one slot is independent of the programs selected in other slots.

Each program group may support an alternative therapy selectable by patient 12, and IMD 14 may deliver therapy according to the multiple programs. IMD 14 may rotate through the multiple programs of the group when delivering stimulation such that numerous conditions of patient 12 are treated. As an illustration, in some examples, stimulation pulses formulated according to parameters defined by different programs may be delivered on a time-interleaved basis. For example, a group may include a program directed to leg pain, a program directed to lower back pain, and a program directed to abdominal pain. In this manner, IMD 14 may treat different symptoms substantially simultaneously.

During use of IMD 14 to treat patient 12, movement of patient 12 among different posture states may affect the ability of IMD 14 to deliver consistent efficacious therapy. For example, leads 16 may migrate toward IMD 14 when patient 12 bends over, resulting in displacement of electrodes and possible disruption in delivery of effective therapy. For example, stimulation energy transferred to target tissue may be reduced due to electrode migration, causing reduced efficacy in terms of relief of symptoms such as pain. As another example, leads 16 may be compressed towards spinal cord 18 when patient 12 lies down. Such compression may cause an increase in the amount of stimulation energy transferred to target tissue. In this example, the amplitude of stimulation therapy may need to be decreased to avoid causing patient 12 additional pain or unusual sensations, which may be considered undesirable side effects that undermine overall efficacy.

Also, posture state changes may present changes in symptoms or symptom levels, e.g., pain level. In some examples, to avoid interruptions in effective therapy, IMD 14 may include a posture state module that detects the patient posture state. IMD 14 may automatically adjust stimulation according to the posture state detection, thereby providing posture state-responsive therapy. For example, the posture state module may include one or more accelerometers that detect when patient 12 occupies a posture state in which it is appropriate to decrease the stimulation amplitude, e.g., when patient 12 lies down. The IMD may automatically reduce stimulation amplitude so that patient 12 does not manually have to do so. Example posture states may include "Upright," "Upright and Active," "Lying Down," "Reclining," and so forth.

Many other examples of reduced efficacy due to increased coupling or decreased coupling of stimulation energy to target tissue may occur due to changes in posture and/or activity level associated with patient posture state. To avoid or reduce possible disruptions in effective therapy due to posture state changes, IMD 14 may include a posture state module that detects the posture state of patient 12 and causes the IMD 14 to automatically adjust stimulation according to the detected posture state. For example, a posture state module may include a posture state sensor such as an accelerometer that detects when patient 12 lies down, stands up, or otherwise changes postures. In some examples, the posture state module may also detect an activity level of the patient.

In response to a posture state detected by the posture state module, IMD 14 may change program group, program, stimulation current or voltage amplitude, pulse width, pulse rate, and/or one or more other parameters, groups, or programs to maintain therapeutic efficacy. When a patient lies down, for example, IMD 14 may automatically reduce stimulation amplitude so that patient 12 does not need to reduce stimulation amplitude manually. In some examples, IMD 14 may automatically increase stimulation amplitude based on posture state. In some examples, IMD 14 may communicate with external programmer 20 to present a proposed change in stimulation in response to a posture state change, and receive approval or rejection of the change from a user, such as patient 12 or a clinician, before automatically applying the therapy change. In some examples, posture state detection may also be used to provide notifications, such as providing notification via a wireless link to a caregiver that a patient has potentially experienced a fall.

Referring still to FIG. 1A, a user, such as a clinician or patient 12, may interact with a user interface of an external device, e.g., external programmer 20, to program IMD 14. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy changes due to posture changes by patient 12. As another example, a user may select programs or program groups. Again, a program may be characterized by an electrode combination, electrode polarities, voltage or current amplitude, pulse width, pulse rate, and/or duration. A group may be characterized by multiple programs that are delivered simultaneously or on an interleaved or rotating basis.

The user interface of external programmer 20 may indicate to the user the posture state in which the patient 12 currently resides. This patient posture state may be a static posture that does not take into account activity level, an activity level that does not take into account posture, or some combination of the posture and activity level that describes the physical position and movement of patient 12. As an example, posture may be characterized as one of the following postures: standing, sitting, lying down on back, lying down on front, lying down on left side, lying down on right side, and reclining. Activity level may be characterized as one of: high, medium and low, or, e.g., walking, biking, running, or the like.

The patient posture state may be represented by a posture state indication presented to patient 12 and generated by the user interface of programmer 20 as a visible, audible, or tactile indication. When presented as a visible indication, the posture state indication may be, for example, a graphical representation, a symbolic icon, a textual representation such as word or number, an arrow, or any other type of indication. The visible indication may be presented via a display, such as an a liquid crystal display (LCD), dot matrix display, organic light-emitting diode (OLED) display, touch screen, or the like. In other examples, the visible indication may be provided in a translucent area that is selectively backlit to indicate a posture. An audible indication may be produced by programmer 20 as spoken words stating a posture state, or different audible tones, different numbers of tones, or other audible information generated by the programmer to indicate posture state. A tactile indication may be produced by programmer 20 different numbers of vibratory pulses delivered in sequence or vibratory pulses of different lengths, amplitudes, or frequencies.

Programmer 20 may present multiple indications representative of different patient posture states. IMD 14 may communicate a patient posture state according to a posture state parameter value sensed by a posture state module to external programmer 20, e.g., by wireless telemetry. IMD 14 may communicate the detected posture state, i.e., posture state detection, or a posture state parameter value used to detect the posture state. For example, IMD 14 may transmit a posture state detection to programmer 20 on a periodic, intermittent, or continuous basis, or in response to a posture state change. Alternatively, programmer 20 may request a posture state detection from IMD 14 on a periodic, intermittent, or continuous basis. The posture state detection provided from IMD 14 to programmer 20 may be a posture state value that is interpreted to determine posture state, or simply an indication of the detected posture state, e.g., upright, lying front, lying back, lying left, lying right, or the like. External programmer 20 may then select and present the associated posture state indication.

In some examples, external programmer 20 may be characterized as a physician or clinician programmer if it is primarily intended for use by a physician or clinician. In other examples, external programmer 20 may be characterized as a patient programmer if it is primarily intended for use by a patient. A patient programmer is generally accessible to patient 12 and, in many examples, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use.

IMD 14 may be constructed with a biocompatible housing, such as titanium or stainless steel, or a polymeric material such as silicone or polyurethane, and surgically implanted at a site in patient 12 near the pelvis. IMD 14 may also be implanted in patient 12 at a location minimally noticeable to patient 12. Alternatively, IMD 14 may be external with percutaneously implanted leads. For SCS, IMD 14 may be located in the lower abdomen, lower back, upper buttocks, or other location to secure IMD 14. Leads 16 may be tunneled from IMD 14 through tissue to reach the target tissue adjacent to spinal cord 18 for stimulation delivery. For DBS or other applications, IMD 14 may be implanted elsewhere, such as in the upper chest area near the clavicle.

Figure 1B:
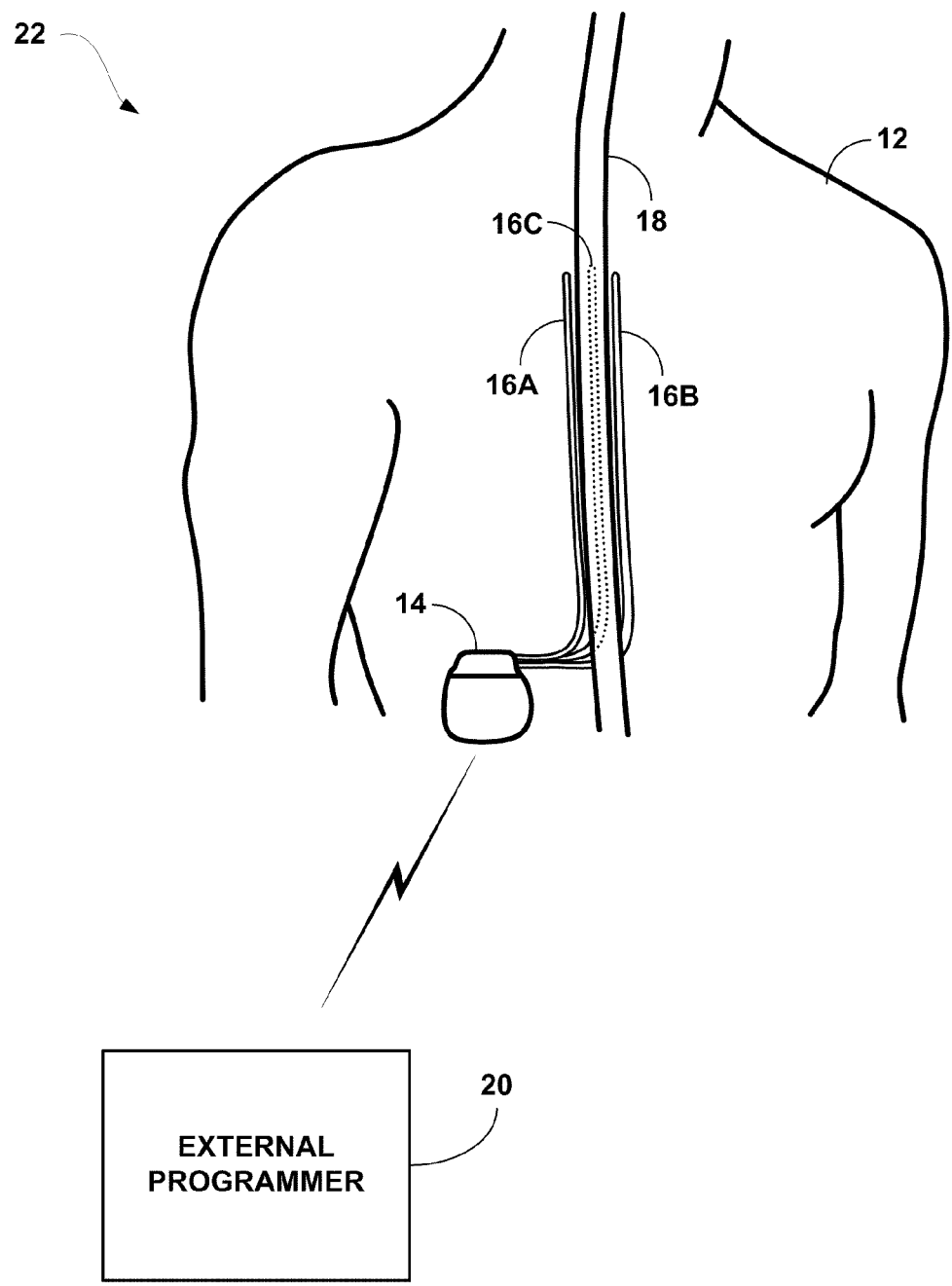
FIG. 1B is a conceptual diagram illustrating an example implantable stimulation system including three implantable stimulation leads.

FIG. 1B is a conceptual diagram illustrating an implantable stimulation system 22 including three implantable stimulation leads 16A, 16B, and 16C (collectively leads 16). System 22 generally conforms to system 10 of FIG. 1A, but includes a third lead. Accordingly, IMD 14 may deliver stimulation via combinations of electrodes carried by all three leads 16, or a subset of the three leads. The third lead, e.g., lead 16C, may include a greater number of electrodes than leads 16A and 16B and be positioned between leads 16A and 16B or on one side of either lead 16A or 16B. The number and configuration of leads 16 may be stored within external programmer 20 to allow programmer 20 to appropriately program stimulation therapy or assist in the programming of stimulation therapy. In some examples, the stimulator may be an external stimulator used for screening therapy prior to implant.

For example, leads 16A and 16B could include four electrodes, while lead 16C includes eight or sixteen electrodes, thereby forming a so-called 4-8-4 or 4-16-4 lead configuration. Other lead configurations, such as 8-16-8, 8-4-8, 16-8-16, 16-4-16, are possible. In some examples, electrodes on lead 16C may be smaller in size and/or closer together than the electrodes of leads 16A or 16B. Movement of lead 16C due to changing activities or postures of patient 12 may, in some instances, more severely affect stimulation efficacy than movement of leads 16A or 16B. Patient 12 may further benefit from the ability of IMD 14 to detect posture states and associated changes and automatically adjust stimulation therapy to maintain therapy efficacy in a three lead system 22.

Figure 1C:
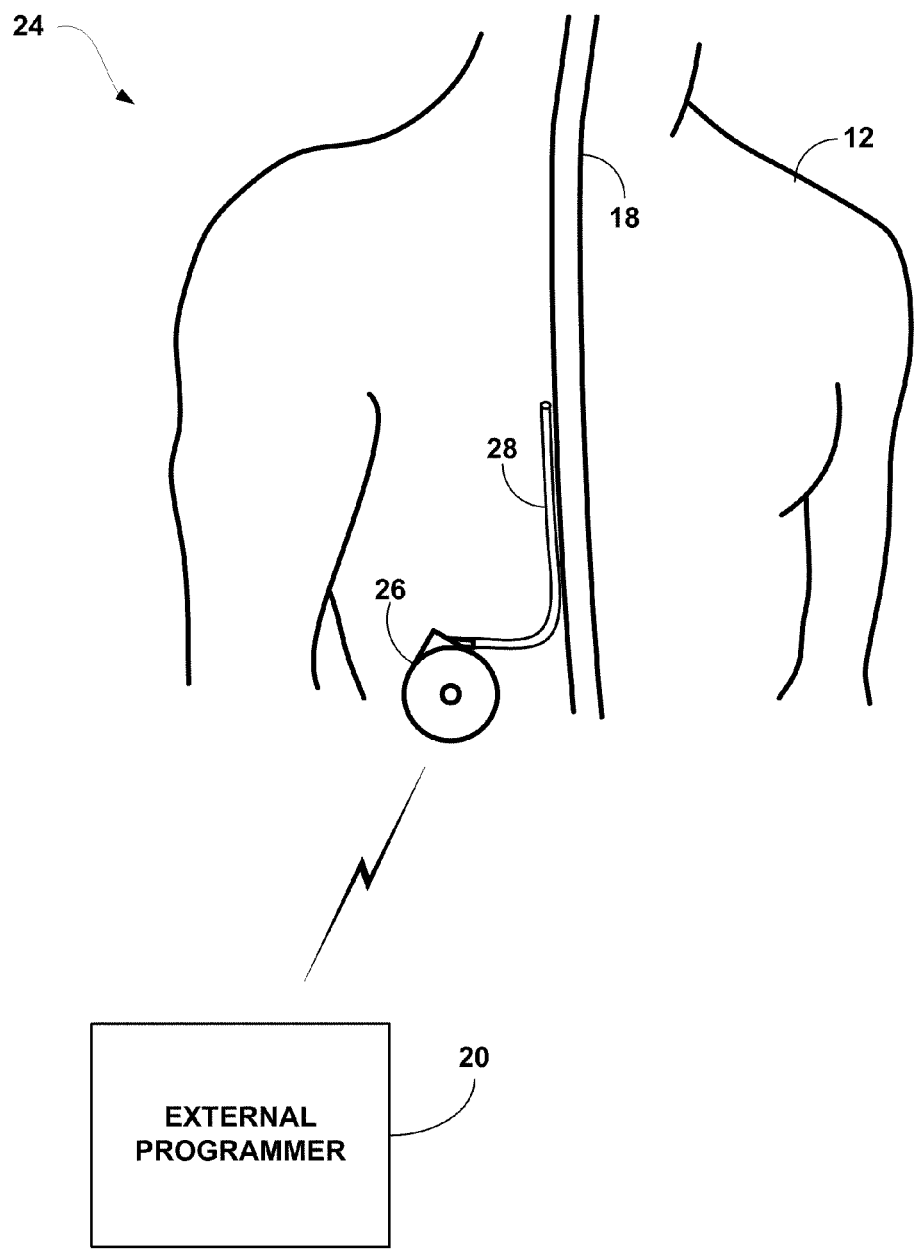
FIG. 1C is a conceptual diagram illustrating an example implantable drug delivery system including a delivery catheter.

FIG. 1C is a conceptual diagram illustrating an implantable drug delivery system 24 including one delivery catheter 28 coupled to an IMD 26 in the form of an implantable fluid delivery pump. As shown in the example of FIG. 1C, drug delivery system 24 may be substantially similar to systems 10 and 22. However, drug delivery system 24 performs similar therapy functions via delivery of one or more therapeutic agents instead of electrical stimulation therapy. IMD 26 functions as a drug pump in the example of FIG. 1C, and IMD 26 communicates with external programmer 20 to initialize therapy or modify therapy during operation. In addition, IMD 26 may be refillable to allow chronic drug delivery.

A fluid delivery port of catheter 28 may be positioned within an intrathecal space or epidural space of spinal cord 18, or, in some examples, adjacent nerves that branch off of spinal cord 18. Although IMD 26 is shown as coupled to only one catheter 28 positioned along spinal cord 18, additional catheters may also be coupled to IMD 26. Multiple catheters may deliver drugs or other therapeutic agents to the same anatomical location or the same tissue or organ. Alternatively, each catheter may deliver therapy to different tissues within patient 12 for the purpose of treating multiple symptoms or conditions. In some examples, IMD 26 may be an external device that includes a percutaneous catheter to deliver a therapeutic agent to patient 12, e.g., in the same manner as catheter 28. Alternatively, the percutaneous catheter can be coupled to catheter 28, e.g., via a fluid coupler. In other examples, IMD 26 may include both electrical stimulation capabilities as described in IMD 14 (FIGS. 1A and 1B) and drug delivery therapy.

IMD 26 may also operate using parameters that define the method of drug delivery. IMD 26 may include programs, or groups of programs, that define different delivery methods for patient 14. For example, a program that controls delivery of a drug or other therapeutic agent may include a titration rate or information controlling the timing of bolus deliveries. Patient 14 may use external programmer 20 to adjust the programs or groups of programs to regulate the therapy delivery.

During use of IMD 26 to treat patient 12, movement of patient 12 among different posture states may affect the ability of IMD 26 to deliver consistent efficacious therapy. For example, catheter 28 may migrate from one location to another when patient 12 bends over or is at a certain high activity level (e.g., working out), resulting in possible disruption in delivery of the fluid (e.g., drug or therapeutic agent). For example, the amount and/or location of delivered fluid may be affected due to catheter migration, causing reduced efficacy in terms of relief of symptoms, for example.

Similar to IMD 14, IMD 26 may include a posture state module that monitors the patient posture state. IMD 26 may adjust therapy based on the posture state. For example, the posture state module may indicate that patient 12 transitions from lying down to standing up. IMD 26 may automatically increase the rate of drug delivered to patient 12 in the standing position if patient 12 has indicated that pain increased when standing. This automated adjustment to therapy based upon posture state may be activated for all or only a portion of the programs used by IMD 26 to deliver therapy.

Figure 2:
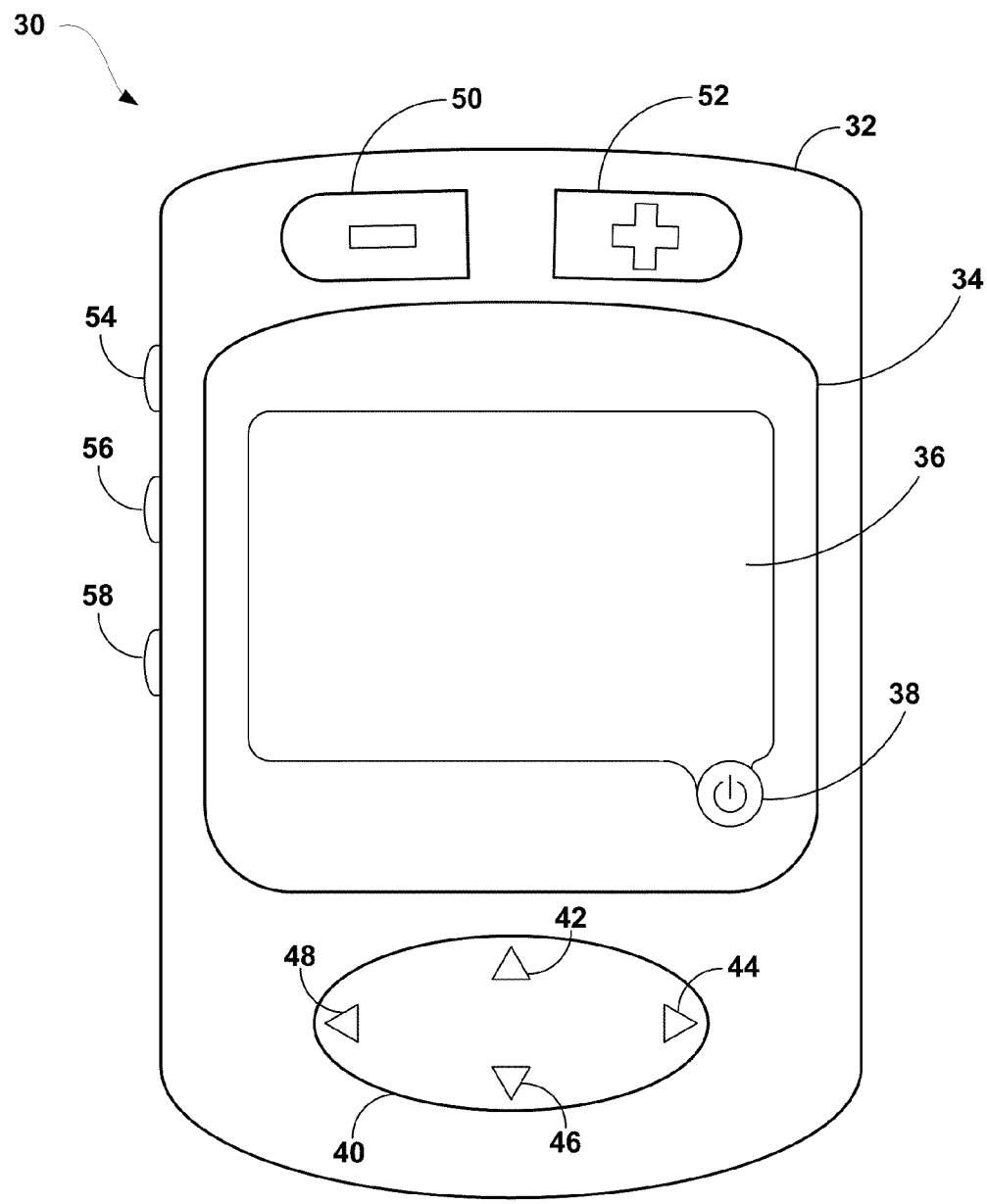
FIG. 2 is a conceptual diagram illustrating an example patient programmer for programming stimulation therapy delivered by an implantable medical device.

FIG. 2 is a conceptual diagram illustrating an example patient programmer 30 for programming stimulation therapy delivered by an IMD. Patient programmer 30 is an example of external programmer 20 illustrated in FIGS. 1A, 1B and 1C and may be used with either IMD 14 or IMD 26. In alternative examples, patient programmer 30 may be used with an external medical device. As shown in FIG. 2, patient programmer 30 provides a user interface (not shown) for a user, such as patient 12, to manage and program stimulation therapy. Patient programmer 30 is protected by housing 32, which encloses circuitry necessary for patient programmer 30 to operate. Although patient programmer 30 may limit some programming features for patient 12, programmer 30 may be configured to display any of example user interfaces 200 described herein.

Patient programmer 30 also includes display 36, power button 38, increase button 52, decrease button 50, sync button 58, stimulation ON button 54, and stimulation OFF button 56. Cover 34 protects display 36 from being damaged during use of patient programmer 30. Patient programmer 30 also includes control pad 40 which allows a user to navigate through items displayed on display 36 in the direction of arrows 42, 44, 46, and 48. In some examples, the buttons and pad 40 may take the form of soft keys (e.g., with functions and contexts indicated on display 36), with functionality that may change, for example, based on current programming operation or user preference. In alternative examples, display 36 may be a touch screen with which patient 12 may directly interact without the use of control pad 40. A touch screen display may eliminate the use of buttons, such as increase button 52 and decrease button 50, although buttons may be used in addition to a touch screen display.

In the illustrated example, patient programmer 30 is a hand held device. Patient programmer 30 may accompany patient 12 throughout a daily routine. In some examples, patient programmer 30 may be used by a clinician when patient 12 visits the clinician in a hospital or clinic. In other examples, patient programmer 30 may be a clinician programmer that remains with the clinician or in the clinic and is used by the clinician and/or patient 12 when the patient is in the clinic. In the example of a clinician programmer, small size and portability may be less important. Accordingly, a clinician programmer may be sized larger than a patient programmer, and it may provide a larger screen for more full-featured programming.

Housing 32 may be constructed of a polymer, metal alloy, composite, or combination material suitable to protect and contain components of patient programmer 30. In addition, housing 32 may be partially or completely sealed such that fluids, gases, or other elements may not penetrate the housing and affect components therein. Power button 38 may turn patient programmer 300N or OFF as desired by patient 12. Patient 12 may control the illumination level, or backlight level, of display 36 by using control pad 40 to navigate through the user interface and increase or decrease the illumination level with decrease and increase buttons 50 and 52.

In some examples, illumination may be controlled by a knob that rotates clockwise and counter-clockwise to control patient programmer 30 operational status and display 36 illumination. Patient programmer 30 may be prevented from turning OFF during telemetry with IMD 14 or another device to prevent the loss of transmitted data or the stalling of normal operation. Alternatively, patient programmer 30 and IMD 14 may include instructions that handle possible unplanned telemetry interruption, such as battery failure or inadvertent device shutdown.

Display 36 may include one or more of a liquid crystal display (LCD), dot matrix display, organic light-emitting diode (OLED) display, touch screen, or similar monochrome or color display capable of providing visible information to patient 12. Display 36 may provide a user interface regarding current stimulation therapy, posture state information, provide a user interface for receiving feedback or medication input from patient 12, display an active group of stimulation programs, and display operational status of patient programmer 30 or IMDs 14 or 26. For example, patient programmer 30 may provide a scrollable list of groups, and a scrollable list of programs within each group, via display 36. In addition, display may present a visible posture state indication based on the posture state detection.

Patient 12 or another user may interact with control pad 40 to navigate through items displayed on display 36. Patient 12 may press control pad 40 on any of arrows 42, 44, 46, and 48 in order to move between items presented on display 36 or move to another screen not currently shown on the display. In some examples, pressing the middle of control pad 40 selects any item highlighted in display 36. In other examples, scroll bars, a scroll wheel, individual buttons, or a joystick may perform the complete or partial functions of control pad 40. In alternative examples, control pad 40 may be a touch pad that allows patient 12 to move a cursor within the user interface displayed on display 36 to manage therapy.

Decrease button 50 and increase button 52 provide an input mechanism for patient 12. In general, activation of decrease button 50 (e.g., by pressing button 50) may decrease the value of a highlighted stimulation parameter every time the decrease button is pressed. In contrast, activation of increase button 52 may increase the value of a highlighted stimulation parameter one step every time the increase button is pressed. While buttons 50 and 52 may be used to control the value of any stimulation parameter, buttons 50 and 52 may also control patient feedback input. When either buttons 50 or 52 is selected, patient programmer 30 may initialize communication with IMD 14 or 26 to change therapy accordingly.

When depressed by patient 12, stimulation ON button 54 directs programmer 30 to generate a command for communication to IMD 14, where the command instructs IMD 14 to turn on stimulation therapy. Stimulation OFF button 56 turns off stimulation therapy when depressed by patient 12. Sync button 58 forces patient programmer 30 to communicate with IMD 14. When patient 12 enters an automatic posture response screen of the user interface, pressing sync button 58 turns on the automatic posture response to allow IMD 14 to automatically change therapy according to the posture state of patient 12. Pressing sync button 58 again, when the automatic posture response screen is displayed, turns off the automatic posture response. In the example of FIG. 2, patient 12 may use control pad 40 to adjust the volume, contrast, illumination, time, and measurement units of patient programmer 30.

In some examples, buttons 54 and 56 may be configured to perform operational functions related to stimulation therapy or the use of patient programmer 30. For example, buttons 54 and 56 may control the volume of audible sounds produced by programmer 20, wherein button 54 increases the volume and button 56 decreases the volume. Button 58 may be pressed to enter an operational menu that allows patient 12 to configure the user interface of patient programmer 30 to the desires of patient 12. For example, patient 12 may be able to select a language, backlight delay time, display brightness and contrast, or other similar options. In alternative examples, buttons 50 and 52 may control all operational and selection functions, such as those related to audio volume or stimulation therapy.

Patient programmer 30 may take other shapes or sizes not described herein. For example, patient programmer 30 may take the form of a clam-shell shape, similar to some cellular phone designs. When patient programmer 30 is closed, some or all elements of the user interface may be protected within the programmer. When patient programmer 30 is opened, one side of the programmer may contain a display while the other side may contain input mechanisms. In any shape, patient programmer 30 may be capable of performing the requirements described herein. Alternative examples of patient programmer 30 may include other input mechanisms such as a keypad, microphone, camera lens, or any other media input that allows the user to interact with the user interface provided by patient programmer 30.

In alternative examples, the buttons of patient programmer 30 may perform different functions than the functions provided in FIG. 2 and/or may have a different arrangement. In addition, other examples of patient programmer 30 may include different button layouts or different numbers of buttons. For example, patient programmer 30 may even include a single touch screen that incorporates all user interface functionality with a limited set of buttons or no other buttons.

Figure 3:
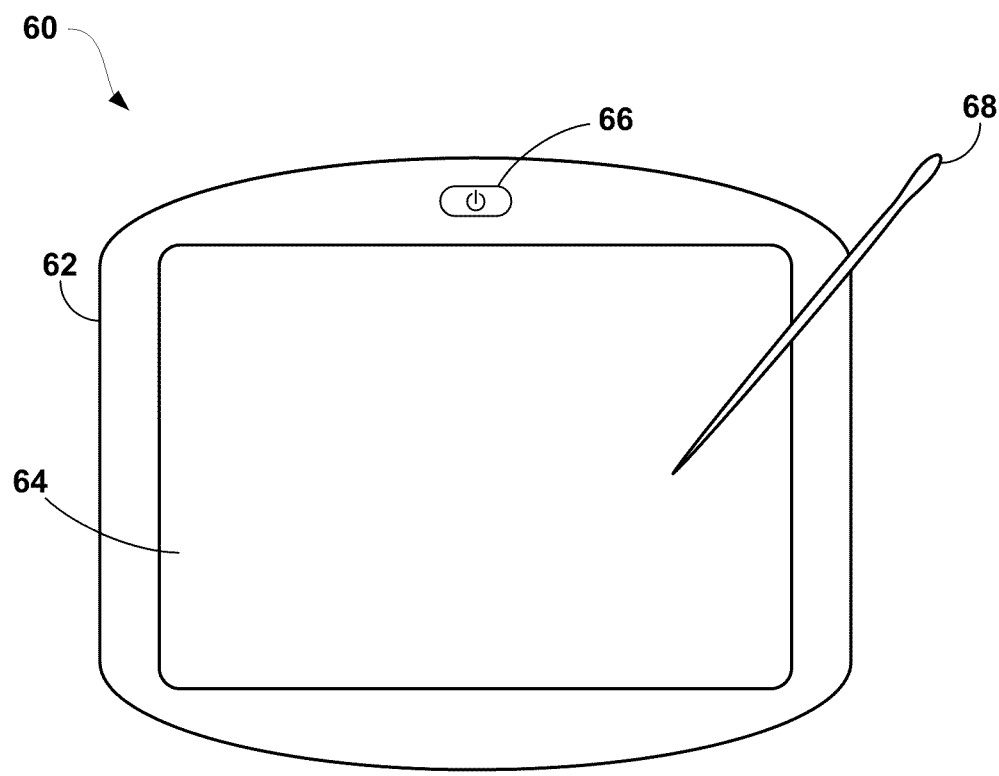
FIG. 3 is a conceptual diagram illustrating an example clinician programmer for programming stimulation therapy delivered by an implantable medical device.

FIG. 3 is a conceptual diagram illustrating an example clinician programmer 60 for programming stimulation therapy delivered by an IMD. Clinician programmer 60 is an example of external programmer 20 illustrated in FIGS. 1A, 1B and 1C and may be used with either IMD 14 or IMD 26. In alternative examples, clinician programmer 60 may be used with an external medical device. As shown in FIG. 3, clinician programmer 60 provides a user interface (not shown) for a user, such as a clinician, physician, technician, or nurse, to manage and program stimulation therapy. Clinician programmer 60 is protected by housing 62, which encloses circuitry necessary for clinician programmer 60 to operate. As described herein, clinician programmer 60 may be configured to display any of example user interfaces 200 described herein.

Clinician programmer 60 is used by the clinician or other user to modify and review therapy to patient 12. The clinician may define therapy parameter values for programs that define stimulation therapy. The clinician may use clinician programmer 60 to define each posture state of patient 12 by using posture cones or other posture volumes as described herein or other techniques for associating posture state sensor output to the posture state of patient 12. Further, the clinician may use clinician programmer 60 to manipulate posture cones or other posture volumes and to manipulate parameters associated with transitions from one posture to another, as will be described in more detail herein.

Clinician programmer 60 includes display 64 and power button 66. In the example of FIG. 3, display 64 is a touch screen that accepts user input via touching certain areas within display 64. The user may use stylus 68 to touch display 64 and select virtual buttons, sliders, keypads, dials, or other such representations presented by the user interface shown by display 64. In some examples, the user may be able to touch display 64 with a finger, pen, or any other pointing device. In alternative examples, clinician programmer 60 may include one or more buttons, keypads, control pads, touch pads, or other devices that accept user input, similar to patient programmer 30.

In the illustrated example, clinician programmer 60 is a hand held device. Clinician programmer 60 may be used within the clinic or on in-house patient calls. Clinician programmer 60 may be used to communicate with multiple IMDs 14 and 26 within different patients. In this manner, clinician programmer 60 may be capable of communicating with many different devices and retain patient data separate for other patient data. In some examples, clinician programmer 60 may be a larger device that may be less portable, such as a notebook computer, workstation, or even a remote computer that communicates with IMD 14 or 26 via a remote telemetry device to display example user interfaces 200.

In some examples, many, if not all, clinician programmer 60 functions may be completed via the touch screen of display 64. The user may program stimulation therapy (e.g., selecting stimulation parameter values), modify programs or groups, retrieve stored therapy data, retrieve posture state information from an IMD or another device, define posture states and other activity information, change the contrast and backlighting of display 64, or any other therapy related function. In addition, clinician programmer 60 may be capable of communicating with a networked server in order to send or receive an email or other message, retrieve programming instructions, access a help guide, send an error message, or perform any other function that may be beneficial to prompt therapy.

Housing 62 may be constructed of a polymer, metal alloy, composite, or combination material suitable to protect and contain components of clinician programmer 60. In addition, housing 62 may be partially or completely sealed such that fluids, gases, or other elements may not penetrate the housing and affect components therein. Power button 66 may turn clinician programmer 60 ON or OFF as desired by the user. Clinician programmer 60 may require a password, biometric input, or other security measure to be entered and accepted before the user can use clinician programmer 60.

Clinician programmer 60 may take other shapes or sizes not described herein. For example, clinician programmer 60 may take the form of a clam-shell shape, similar to some cellular phone designs. When clinician programmer 60 is closed, at least a portion of display 64 is protected within housing 62. When clinician programmer 60 is opened, one side of the programmer may contain a display while the other side may contain input mechanisms. In any shape, clinician programmer 60 may be capable of performing the requirements described herein.

Figure 4:
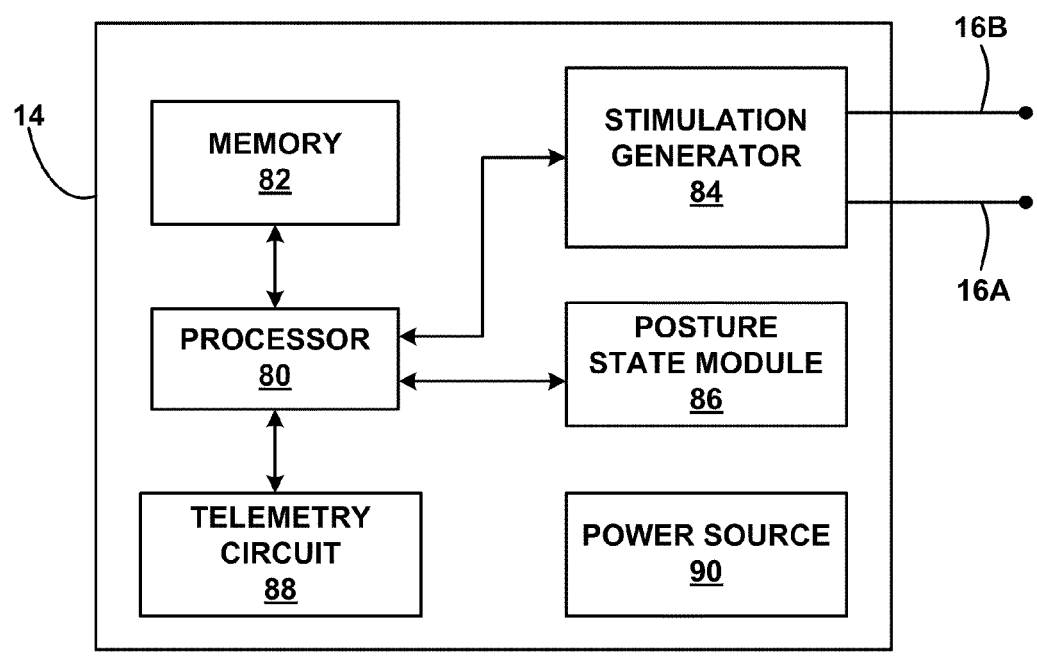
FIG. 4 is a functional block diagram illustrating various components of an implantable medical device in the form of an example implantable electrical stimulator.

FIG. 4 is a functional block diagram illustrating various components of an example implantable medical device (IMD 14) in the form of an example implantable electrical stimulator. In the example of FIG. 4, IMD 14 includes a processor 80, memory 82, stimulation generator 84, posture state module 86, telemetry circuit 88, and power source 90. The stimulation generator 84 forms a therapy delivery module.

Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 82 may store instructions for execution by processor 80, stimulation therapy data, posture state information, posture state indications, and any other information regarding therapy or patient 12. Therapy information may be recorded for long-term storage and retrieval by a user, and the therapy information may include any data created by or stored in IMD 14. Memory 82 may include separate memories for storing instructions, posture state information, program histories, and any other data that may benefit from separate physical memory modules.

Processor 80 controls stimulation generator 84 to deliver electrical stimulation via electrode combinations formed by electrodes in one or more electrode arrays. For example, stimulation generator 84 may deliver electrical stimulation therapy via electrodes on one or more leads 16, e.g., as stimulation pulses or continuous waveforms. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination. The functions attributed to processors described herein may be embodied as software, firmware, hardware, or any combination thereof.

Stimulation generator 84 may include stimulation generation circuitry to generate stimulation pulses or waveforms and switching circuitry to switch the stimulation across different electrode combinations, e.g., in response to control by processor 80. In particular, processor 80 may control the switching circuitry on a selective basis to cause stimulation generator 84 to deliver electrical stimulation to selected electrode combinations and to shift the electrical stimulation to different electrode combinations in a first direction or a second direction when the therapy must be delivered to a different location within patient 12. In other examples, stimulation generator 84 may include multiple current sources to drive more than one electrode combination at one time. In this example, stimulation generator 84 may decrease current to the first electrode combination and simultaneously increase current to the second electrode combination to shift the stimulation therapy.

An electrode configuration, e.g., electrode combination and associated electrode polarities may be represented by a data stored in a memory location, e.g., in memory 82, of IMD 14. Processor 80 may access the memory location to determine the electrode combination and control stimulation generator 84 to deliver electrical stimulation via the indicated electrode combination. To adjust electrode combinations, amplitudes, pulse rates, or pulse widths, processor 80 may command stimulation generator 84 to make the appropriate changes to therapy according to instructions within memory 82 and rewrite the memory location to indicate the changed therapy. In other examples, rather than rewriting a single memory location, processor 80 may make use of two or more memory locations.

When activating stimulation, processor 80 may access not only the memory location specifying the electrode combination but also other memory locations specifying various stimulation parameters such as voltage or current amplitude, pulse width and pulse rate. Stimulation generator 84, e.g., under control of processor 80, then makes use of the electrode combination and parameters in formulating and delivering the electrical stimulation to patient 12.

An exemplary range of electrical stimulation parameters likely to be effective in treating chronic pain, e.g., when applied to spinal cord 18, are listed below. While stimulation pulses are described, stimulation signals may be of any of a variety of forms such as sine waves or the like.

1. Pulse Rate: between approximately 0.5 Hz and approximately 1200 Hz, more preferably between approximately 5 Hz and approximately 250 Hz, and still more preferably between approximately 30 Hz and approximately 130 Hz.

2. Amplitude: between approximately 0.1 volts and approximately 50 volts, more preferably between approximately 0.5 volts and approximately 20 volts, and still more preferably between approximately 1 volt and approximately 10 volts. In other examples, a current amplitude may be defined as the biological load in the voltage that is delivered. For example, the range of current amplitude may be between approximately 0.1 milliamps (mA) and approximately 50 mA.

3. Pulse Width: between approximately 10 microseconds and approximately 5000 microseconds, more preferably between approximately 100 microseconds and approximately 1000 microseconds, and still more preferably between approximately 180 microseconds and approximately 450 microseconds.

In other applications, different ranges of parameter values may be used. For DBS, as one example, alleviation or reduction of symptoms associated with Parkinson's disease, essential tremor, epilepsy, psychiatric disorders or other disorders may make use of stimulation having a pulse rate in the range of approximately 0.5 to approximately 1200 Hz, such as between approximately 5 to approximately 250 Hz, or between approximately 30 to approximately 185 Hz, and a pulse width in the range of approximately 10 microseconds and approximately 5000 microseconds, such as between approximately 60 microseconds and approximately 1000 microseconds, or between approximately 60 microseconds and approximately 450 microseconds, or between approximately 60 microseconds and approximately 150 microseconds. Amplitude ranges such as those described above with reference to SCS, or other amplitude ranges, may be used for different DBS applications.

Processor 80 accesses stimulation parameters in memory 82, e.g., as programs and groups of programs. Upon selection of a particular program group, processor 80 may control stimulation generator 84 to generate and deliver stimulation according to the programs in the groups, e.g., simultaneously or on a time-interleaved basis. A group may include a single program or multiple programs. Each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads. Processor 80 also may control telemetry circuit 88 to send and receive information to and from external programmer 20. For example, telemetry circuit 88 may send information to and receive information from patient programmer 30.

Posture state module 86 allows IMD 14 to sense the patient posture state, e.g., posture, activity, or any other static position or motion of patient 12. In the example of FIG. 4, posture state module 86 may include one or more accelerometers, such as three-axis accelerometers, capable of detecting static orientation or vectors in three-dimensions (e.g., x, y, z coordinate vectors). Example accelerometers may include micro-electro-mechanical systems (MEMS)-based accelerometers. In some examples, posture state module 86 may alternatively or additionally include one or more gyroscopes, piezoelectric crystals, pressure transducers, or other sensors to sense the posture state of patient 12. Posture sensor data generated by posture state module 86 and processor 80 may correspond to an activity and/or posture undertaken by patient 12 or a gross level of physical activity, e.g., activity counts based on footfalls or the like.

Posture sensor data from posture state module 86 may be stored in memory 82 for later review by a clinician, used to adjust therapy, present a posture state indication to patient 12 (e.g., via patient programmer 30), or some combination thereof. As an example, processor 80 may record the posture state parameter value, or output of the 3-axis accelerometer as posture sensor data and use the posture sensor data to form posture state reference data for a certain predefined posture indicated by the posture sensor data. In this manner, IMD 14 may be able to track how often patient 12 remains within a certain posture. IMD 14 may also store which group or program was being used to deliver therapy when patient 12 was in the sensed posture.

Further, processor 80 may also adjust therapy for a newly-detected posture when posture state module 86 indicates that patient 12 has in fact changed posture states. Therefore, IMD 14 may be configured to provide posture-responsive stimulation therapy to patient 12. Stimulation adjustments in response to posture state may be automatic or semi-automatic (e.g., subject to patient approval). In some examples, fully automatic adjustments may be desirable so that IMD 14 may react more quickly to posture state changes. The adjustments may be adjustments to one or more of voltage pulse amplitude or current pulse amplitude, pulse width, pulse rate, and electrode configuration, i.e., electrode combination and electrode polarity. In some examples, the adjustments may take the form of selection of different programs. In each example, adjustments may be made in response to detection of posture state changes, and include adjustments specified for particular posture states.

Posture sensor data from posture state module 86 that indicates the posture state may constantly vary throughout the day of patient 12. However, a certain activity (e.g., walking, running, or biking) or a posture (e.g., standing, sitting, or lying down) may include multiple posture sensor data values from posture state module 86. Memory 82 may include definitions for each posture state of patient 12 based on posture state reference data. In one example, the definitions of each posture state may be illustrated as a posture zone. A posture zone may be defined by any one of different volumetric shapes, e.g., cylinders, spheres, toroid, or the like. In one example, a posture zone may be defined by a cone in three-dimensional space. Whenever the posture sensor data, e.g., a coordinate vector, from the three-axis accelerometer of posture state module 86 resides within a predefined cone defined by the posture state reference data, processor 80 indicates that patient 12 is in the posture state associated with the cone. In some examples, posture sensor data from the 3-axis accelerometer may be compared to data in a look-up table or applied to an equation to determine the posture state in which patient 12 currently resides.

Posture-responsive stimulation may allow IMD 14 to implement a certain level of automation in therapy adjustments. Automatically adjusting stimulation may free patient 12 from the constant task of manually adjusting therapy each time patient 12 changes posture or starts and stops a certain posture state or activity. Such manual adjustment of stimulation parameters can be tedious, requiring patient 14 to, for example, depress one or more keys of patient programmer 30 multiple times during the patient posture state to maintain adequate symptom control. In some examples, patient 12 may eventually be able to enjoy posture state responsive stimulation therapy without the need to continue making changes for different postures via patient programmer 30. Instead, patient 12 may transition immediately or over a period of time to fully automatic adjustments based on posture state.

Although posture state module 86 is described as containing the 3-axis accelerometer, posture state module 86 may contain multiple single-axis accelerometers, dual-axis accelerometers, 3-axis accelerometers, or some combination thereof. In some examples, an accelerometer or other sensor may be located within or on IMD 14, on one of leads 16 (e.g., at the distal tip or at an intermediate position), an additional sensor lead positioned somewhere within patient 12, within an independent implantable sensor, or even worn on patient 12. For example, one or more microsensors may be implanted within patient 12 to communicate posture state information wirelessly to IMD 14. In this manner, the posture state of patient 12 may be determined from multiple posture state sensors placed at various locations on or within the body of patient 12.

In other examples, posture state module 86 may additionally or alternatively be configured to sense one or more physiological parameters of patient 12. For example, physiological parameters may include heart rate, electromyography (EMG), an electroencephalogram (EEG), an electrocardiogram (ECG), temperature, respiration rate, or pH. These physiological parameters may be used by processor 80, in some examples, to confirm or reject changes in sensed posture state that may result from vibration, patient travel (e.g., in an aircraft, car or train), or some other false positive of posture state.

In some examples, processor 80 processes the analog output of the posture state sensor in posture state module 86 to determine activity and/or posture data. For example, where the posture state sensor comprises an accelerometer, processor 80 or a processor of posture state module 86 may process the raw signals provided by the posture state sensor to determine activity counts. In some examples, processor 80 may process the signals provided by the posture state sensor to determine velocity of motion information along each axis.

In one example, each of the x, y, and z signals provided by the posture state sensor has both a DC component and an AC component. The DC components describes the gravitational force exerted upon the sensor and can thereby be used to determine orientation of the sensor within the gravitational field of the earth. Assuming the orientation of the sensor is relatively fixed with respect to the patient, the DC components of the x, y and z signals may be utilized to determine the patient's orientation within the gravitational field, and hence to determine the posture of the patient, assuming proper orientation of the sensor to the patient's body.

The AC component of the x, y and z signals yields information about patient motion. In particular, the AC component of a signal may be used to derive a value for an activity describing the patient's motion. This activity may involve a level, direction of motion, or acceleration of the patient.

One method for determining the patient activity is by determining an activity count. An activity count may be used to indicate the activity or activity level of patient 12. For example, a signal processor may sum the magnitudes of the AC portion of an accelerometer signal for N consecutive samples. For instance, assuming sampling occurs at 25 Hz, N may be set to 25, so that count logic provides the sum of the samples that are obtained in one second. This sum may be referred to as an "activity count." The number "N" of consecutive samples may be selected by the processor based on the current posture state, if desired. The activity count may be the activity portion of the activity parameter value that is added to the posture portion. The resulting activity parameter value may then incorporate both activity and posture to generate an accurate indication of the motion of patient 12.

As another example, the activity parameter value may be defined describing direction of motion. This activity parameter value may be associated with a coordinate vector and an associated tolerance, which may be a distance from the coordinate vector. Another example of an activity parameter value relates to acceleration. The value quantifying a level of change of motion over time in a particular direction may be associated with this parameter referenced in the activity parameter value.

IMD 14 wirelessly communicates with an external device, e.g., external programmer 20, patient programmer 30 or clinician programmer 60, or another device by radio frequency (RF) communication or proximal inductive interaction of IMD 14 with external programmer 20. Telemetry circuit 88 may send information to and receive information from external programmer 20 on a continuous basis, at periodic intervals, at non-periodic intervals, or upon request from the stimulator or programmer. To support RF communication, telemetry circuit 88 may include appropriate electronic components, such as amplifiers, filters, mixers, encoders, decoders, or the like. In some examples, telemetry circuit 88 may support other standard communication protocols such as, for example, Bluetooth® and may include the appropriate components.

Power source 90 delivers operating power to the components of IMD 14. Power source 90 may include a small rechargeable or non-rechargeable battery and a power generation circuit to produce the operating power. Recharging may be accomplished through proximal inductive interaction between an external charger and an inductive charging coil within IMD 14. In some examples, power requirements may be small enough to allow IMD 14 to utilize patient motion and implement a kinetic energy-scavenging device to trickle charge a rechargeable battery. In other examples, traditional batteries may be used for a limited period of time. As a further alternative, an external inductive power supply could transcutaneously power IMD 14 when needed or desired.

Figure 5:
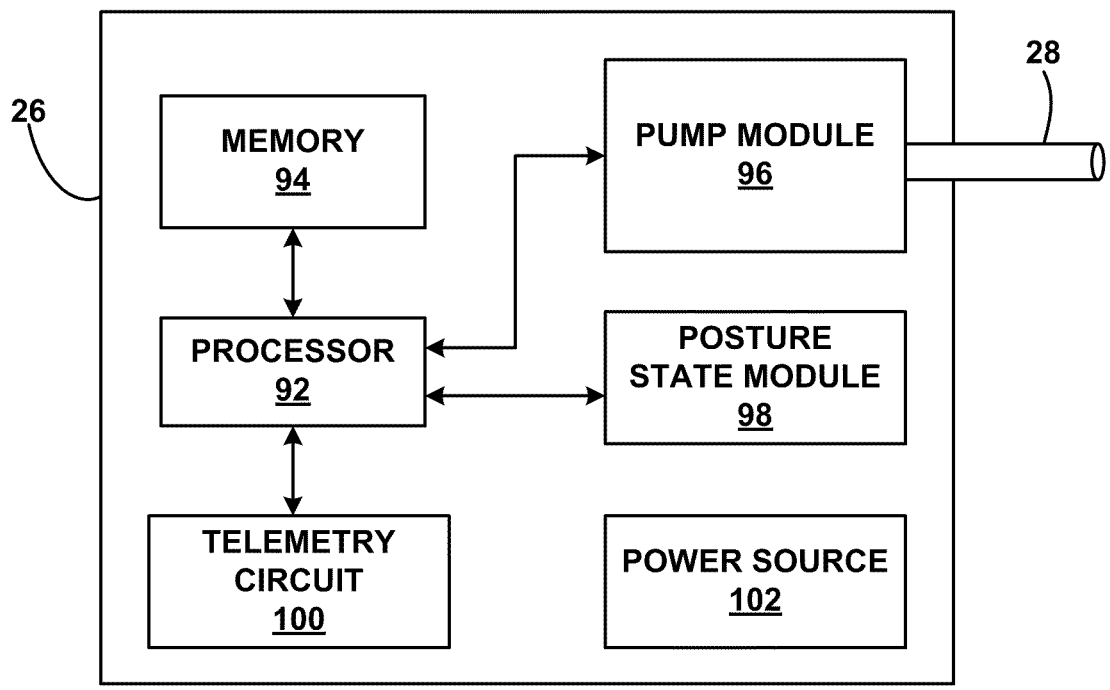
FIG. 5 is a functional block diagram illustrating various components of an implantable medical device in the form of an example implantable drug pump.

FIG. 5 is a functional block diagram illustrating various components of an example implantable medical device (IMD 26) in the form of an example implantable drug pump. IMD 26 is a drug pump that operates substantially similar to IMD 14 of FIG. 4, but delivers a therapeutic agent instead of electrical stimulation. IMD 26 includes processor 92, memory 94, pump module 96, posture state module 98, telemetry circuit 100, and power source 102. Instead of stimulation generator 84 of IMD 14, IMD 26 includes pump module 96 for delivering drugs or some other therapeutic agent via catheter 28. Pump module 96 may include a reservoir to hold the drug and a pump mechanism to force drug out of catheter 28 and into patient 12.

Processor 92 controls pump module 96 according to therapy instructions stored within memory 94. For example, memory 94 may contain the programs or groups of programs that define the drug delivery therapy for patient 12. A program may indicate the bolus size or flow rate of the drug, and processor 92 may accordingly deliver therapy. Processor 92 may also use posture state information from posture state module 98 to adjust drug delivery therapy when patient 12 changes posture states, e.g., adjusts his or her posture.

Figure 6:
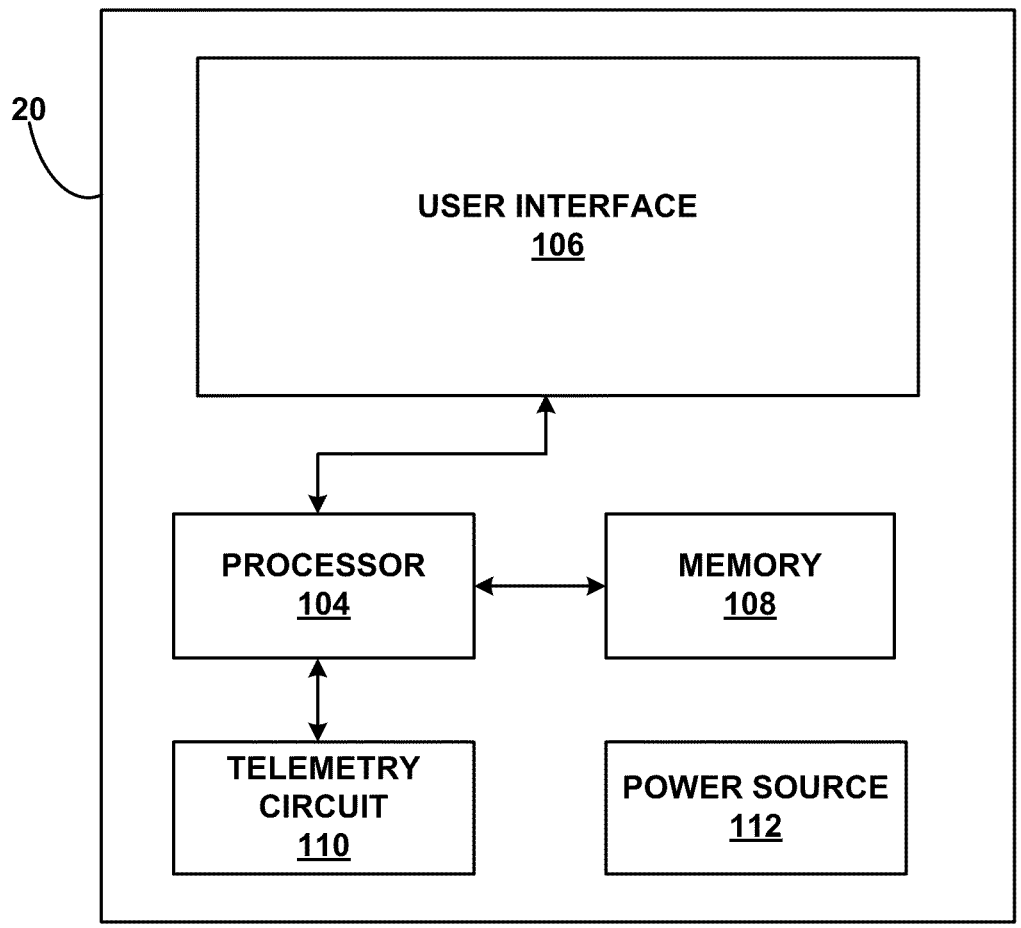
FIG. 6 is a functional block diagram illustrating various components of an example external programmer for an implantable medical device.

FIG. 6 is a functional block diagram illustrating various components of an external programmer 20 for IMDs 14 or 26. Programmer 20 may be a handheld computing device, a workstation or another dedicated or multifunction computing device. For example, programmer 20 may be a general purpose computing device (e.g., a personal computer, personal digital assistant (PDA), cell phone, and so forth) or may be a computing device dedicated to programming the IMD. As shown in FIG. 6, external programmer 20 may include processor 104, memory 108, telemetry circuit 110, user interface 106, and power source 112. External programmer 20 may be embodied as patient programmer 30 (FIG. 2) or clinician programmer 60 (FIG. 3).

Processor 104 may process instructions by memory 108 and may store user input received through user interface 106 into the memory when appropriate for the current therapy. In addition, processor 104 may provide and support any of the functionality described herein with respect to each example of user interface 106. Processor 104 may comprise any one or more of a microprocessor, DSP, ASIC, FPGA, or other digital logic circuitry, and the functions attributed to programmer 104 may be embodied as software, firmware, hardware or any combination thereof.

Memory 108 may include any one or more of a RAM, ROM, EEPROM, flash memory or the like. Memory 108 may include instructions for operating user interface 106, telemetry module 110 and managing power source 112. Memory 108 may store program instructions that, when executed by processor 104, cause processor 104 and programmer 20 to provide the functionality ascribed to them herein. Memory 108 also includes instructions for generating and delivering programming commands to IMD 14, such as a programming command that instructs IMD 14 to activate or deactivate a posture-responsive therapy mode. Memory 108 may also include a removable memory portion that may be used to provide memory updates or increases in memory capacities. A removable memory may also allow patient data to be easily transferred to another computing device, or to be removed before programmer 20 is used to program therapy for another patient.

A clinician, patient 12, or another user (e.g., a patient caretaker) interacts with user interface 106 in order to manually change the stimulation parameter values of a program, change programs within a group, turn posture-responsive stimulation ON or OFF, view therapy information, view posture state information, or otherwise communicate with IMDs 14 or 26. A clinician or patient 12 may also interact with user interface 106 to manually change the definition of a posture state, e.g., by changing the posture cone associate with a posture state, and to modify times associated with transitioning from one state to another. The user may be given a visual representation of the posture zones so that the user may re-size the zones to more accurately to fit the patient. Additionally, using color coding or shading techniques for areas affected by changes made by the user to the size of the zones or the transition times between postures, may provide an easier and more user friendly programming experience for the user. Using the techniques of this disclosure may reduce user confusion and error as a user defines a zone size more fitting for a patient.

User interface 106 may include a screen and one or more mechanisms, such as, buttons, as in the example of patient programmer 30, that allow external programmer 20 to receive input from a user. Alternatively or additionally, user interface 106 may utilize a touch screen display, as in the example of clinician programmer 60. The screen may be a liquid crystal display (LCD), dot matrix display, organic light-emitting diode (OLED) display, touch screen, or any other device capable of delivering and/or accepting information. For visible posture state indications, a display screen may suffice. For audible and/or tactile posture state indications, programmer 20 may further include one or more audio speakers, voice synthesizer chips, piezoelectric buzzers, or the like.

Processor 104 controls user interface 106, retrieves data from memory 108 and stores data within memory 108. Processor 104 also controls the transmission of data through telemetry circuit 110 to IMDs 14 or 26. Memory 108 includes operation instructions for processor 104 and data related to patient 12 therapy.

Telemetry circuit 110 allows the transfer of data to and from IMD14, or IMD 26. Telemetry circuit 110 may communicate automatically with IMD 14 at a scheduled time or when the telemetry circuit detects the proximity of the stimulator. Alternatively, telemetry circuit 110 may communicate with IMD 14 when signaled by a user through user interface 106. To support RF communication, telemetry circuit 110 may include appropriate electronic components, such as amplifiers, filters, mixers, encoders, decoders, and the like. Power source 112 may be a rechargeable battery, such as a lithium ion or nickel metal hydride battery. Other rechargeable or conventional batteries may also be used. In some examples, external programmer 20 may be used when coupled to an alternating current (AC) outlet, i.e., AC line power, either directly or via an AC/DC adapter. In some examples, telemetry circuit 110 may support other standard communication protocols such as, for example, Bluetooth® and may include the appropriate components.

Figure 7:
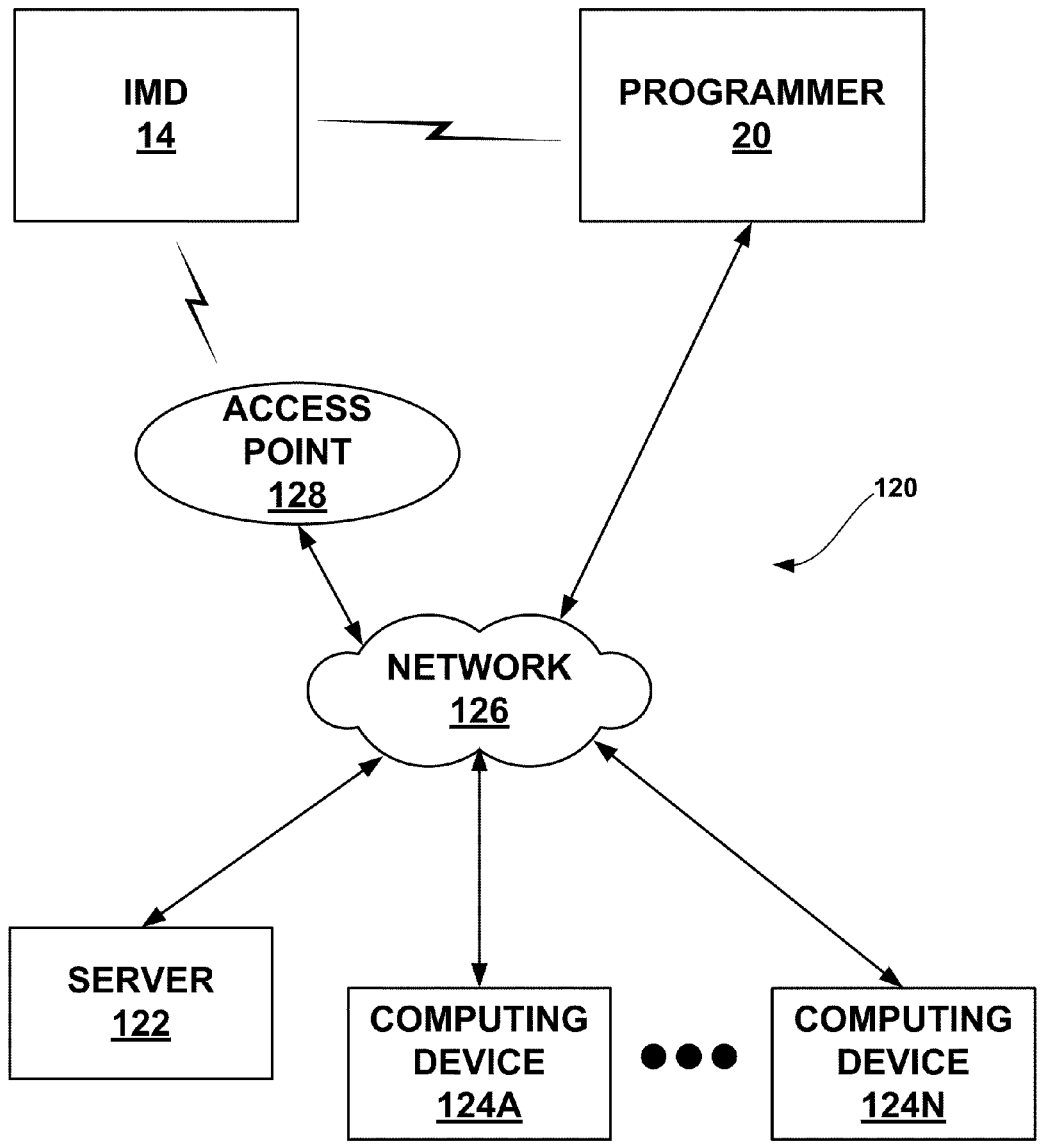
FIG. 7 is a block diagram illustrating an example system that includes an external device, such as a server, and one or more computing devices that are coupled to an implantable medical device and external programmer shown in FIGS. 1A-1C via a network.

FIG. 7 is a block diagram illustrating an example system 120 that includes an external device, such as a server 122, and one or more computing devices 124A-124N, that are coupled to IMD 14 and external programmer 20 shown in FIGS. 1A-1C via a network 126. In this example, IMD 14 may use its telemetry circuit 88 to communicate with external programmer 20 via a first wireless connection, and to communication with an access point 128 via a second wireless connection. In other examples, IMD 26 may also be used in place of IMD 14, and external programmer 20 may be either patient programmer 30 or clinician programmer 60.

In the example of FIG. 7, access point 128, external programmer 20, server 122, and computing devices 124A-124N may be interconnected, and able to communicate with each other, through network 126. In some examples, one or more of access point 128, external programmer 20, server 122, and computing devices 124A-124N may be coupled to network 126 through one or more wireless connections. IMD 14, external programmer 20, server 122, and computing devices 124A-124N may each comprise one or more processors, such as one or more microprocessors, DSPs, ASICs, FPGAs, programmable logic circuitry, or the like, that may perform various functions and operations, such as those described in this disclosure.

Access point 128 may comprise a device, such as a home monitoring device, that connects to network 126 via any of a variety of connections, such as telephone dial-up, digital subscriber line (DSL), or cable modem connections. In other examples, access point 128 may be coupled to network 126 through different forms of connections, including wired or wireless connections.

During operation, IMD 14 may collect and store various forms of data. For example, IMD 14 may collect sensed posture state information during therapy that indicate how patient 12 moves throughout each day. In some examples, IMD 14 may directly analyze the collected data to evaluate the patient posture state, such as what percentage of time patient 12 was in each identified posture. In other examples, however, IMD 14 may send stored data relating to posture state information to external programmer 20 and/or server 122, either wirelessly or via access point 128 and network 126, for remote processing and analysis. For example, IMD 14 may sense, process, trend and evaluate the sensed posture state information. This communication may occur in real time, and network 126 may allow a remote clinician to review the current patient posture state by receiving a presentation of a posture state indication on a remote display, e.g., computing device 124A. Alternatively, processing, trending, and evaluation functions may be distributed to other devices such as external programmer 20 or server 122, which are coupled to network 126. In addition, posture state information may be archived by any of such devices, e.g., for later retrieval and analysis by a clinician.

In some examples, IMD 14, external programmer 20 or server 122 may process posture state information or raw data and/or therapy information into a displayable posture state report, which may be displayed via external programmer 20 or one of computing devices 124A-124N. The posture state report may contain trend data for evaluation by a clinician, e.g., by visual inspection of graphic data. In some examples, the posture state report may include the number of activities patient 12 conducted, a percentage of time patient 12 was in each posture state, the average time patient 12 was continuously within a posture state, what group or program was being used to deliver therapy during each activity, the number of adjustments to therapy during each respective posture state, or any other information relevant to patient 12 therapy, based on analysis and evaluation performed automatically by IMD 14, external programmer 20 or server 122. A clinician or other trained professional may review and/or annotate the posture state report, and possibly identify any problems or issues with the therapy that should be addressed.

In some examples, server 122 may be configured to provide a secure storage site for archival of posture state information that has been collected from IMD 14 and/or external programmer 20. Network 126 may comprise a local area network, wide area network, or global network, such as the Internet. In some examples, external programmer 20 or server 122 may assemble posture state information in web pages or other documents for viewing by trained professionals, such as clinicians, via viewing terminals associated with computing devices 124A-124N. System 120 may be implemented, in some aspects, with general network technology and functionality similar to that provided by the Medtronic CareLink® Network developed by Medtronic, Inc., of Minneapolis, Minn.

Although some examples of the disclosure may involve posture state information and data, system 120 may be employed to distribute any information relating to the treatment of patient 12 and the operation of any device associated therewith. For example, system 120 may allow any issues with the therapy or device to be immediately reported to the clinician. In addition, system 120 may allow the clinician to remotely intervene in the therapy and reprogram IMD 14, patient programmer 30, or communicate with patient 12. In one example, the clinician may utilize system 120 to monitor multiple patients and share data with other clinicians in an effort to coordinate rapid evolution of effective treatment of patients.

Furthermore, although the disclosure is described with respect to SCS therapy, such techniques may be applicable to IMDs that convey other therapies in which posture state information is important, such as, e.g., DBS, pelvic floor stimulation, gastric stimulation, occipital stimulation, functional electrical stimulation, and the like. Also, in some examples, techniques for evaluating posture state information, as described in this disclosure, may be applied to IMDs that are generally dedicated to sensing or monitoring and do not include stimulation or other therapy components. For example, an implantable monitoring device may be implanted in conjunction with an implantable stimulation device, and configured to evaluate sensing integrity of leads or electrodes associated with the implantable monitoring device based on sensed signals evoked by delivery of stimulation by the implantable stimulation device. Furthermore, while the disclosure is described with respect to an implantable stimulator, in some examples, the stimulator may be an external stimulator used for screening therapy prior to implant.

Figure 8A:
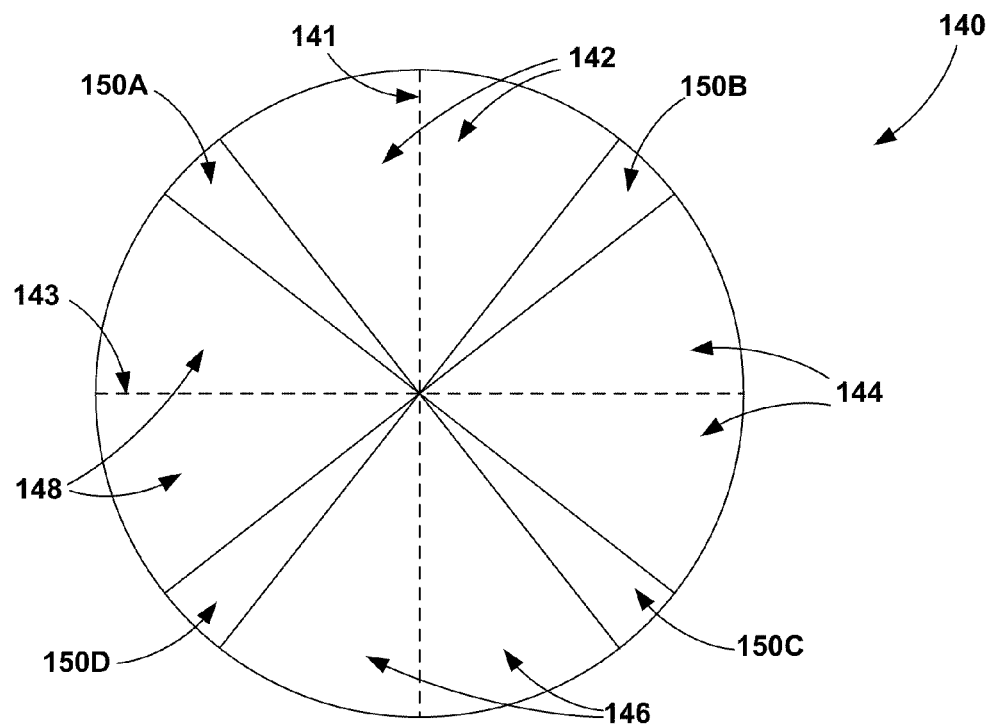
FIGS. 8A-8C are conceptual illustrations of example posture state spaces within which postures state reference data may define the posture state of a patient.
Figure 8B:
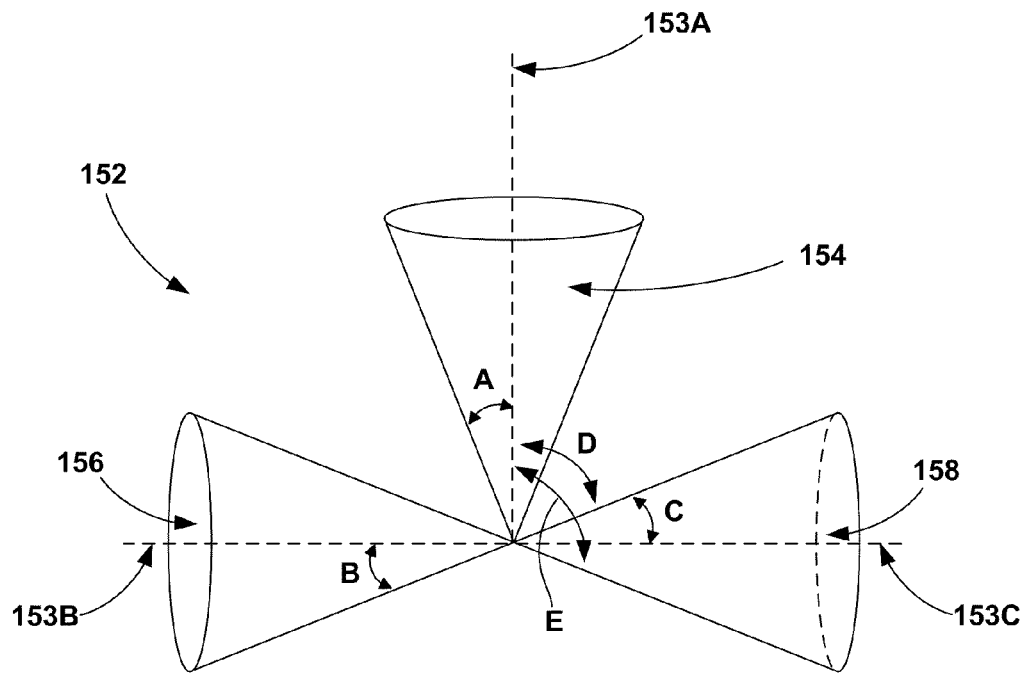
Figure 8C:
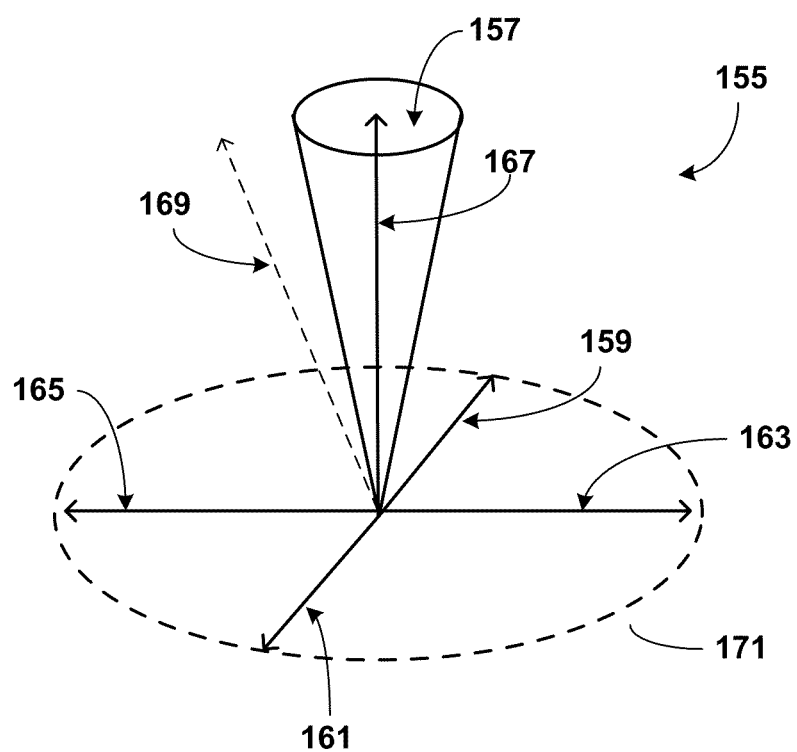

FIGS. 8A-8C are conceptual illustrations of posture state spaces 140, 152, 155 within which posture state reference data may define the posture state of patient 12 based on posture zones within each of the posture state spaces. Posture state reference data may define certain zones associated with particular posture states of patient 12 within the respective posture state spaces 140, 152, 155. The output of one or more posture state sensors may be analyzed by posture state module 86 with respect to posture state spaces 140, 152, 155 to determine the posture state of patient 12 by determining the posture zone within the posture state space. For example, if the output of one or more posture state sensors is within a particular posture zone defined by posture state reference data, posture state module 86 may determine that patient 12 is within the posture state associated with the respective posture state zone.

In some examples, one or more posture state zones may be defined by any one of different volumetric shapes, e.g., cylinders, spheres, toroid, or the like. In one example, posture state cones may be used to define a posture state of patient 12 based on the output from a posture state sensor of a posture state according to an example method for posture state detection. A posture state cone may be centered about a posture state reference coordinate vector that corresponds to a particular posture state. In the examples of FIGS. 8A and 8B, the posture state module 86 of IMD 14 or IMD 26 may use a posture state sensor, e.g., a three-axis accelerometer that provides data indicating the posture state of patient 12, to sense posture vectors. While the sensed data may be indicative of any posture state, postures of patient 12 will generally be used below to illustrate the concept of posture cones. As shown in FIG. 8A, posture state space 140 represents a vertical plane dividing patient 12 from left and right sides, or the sagittal plane. A posture state parameter value from two axes of the posture state sensor may be used to determine the current posture state of patient 12 according to the posture state space 140 by determining the posture zone in which patient 12 is. The posture state data may include x, y and z coordinate values. While this disclosure discusses the example of posture cones, it should be understood that cones are discussed for purposes of illustration, and posture zones may be defined by any one of different volumetric shapes.

In one example, a posture cone may be defined by a reference coordinate vector for a given posture state in combination with a distance or angle defining a range of coordinate vectors within a cone surrounding the posture reference coordinate vector. In other examples, a posture cone may be defined by a reference coordinate vector and a range of cosine values computed using the reference coordinate vector as an adjacent vector and any of the outermost vectors of the cone as a hypotenuse vector. If a sensed posture state vector is within an applicable angle or distance of the reference coordinate vector, or if the sensed posture state vector and the reference coordinate vector produce a cosine value in a specified cosine range, then posture state vector is determined to reside within the posture cone defined by the reference coordinate vector.

Posture state space 140 is segmented into different posture zones (e.g., cones) that are indicative of a certain posture state of patient 12. In the example of FIG. 8A, upright cone 142 indicates that patient 12 is sitting or standing upright, lying back cone 148 indicates that patient 12 is lying back down, lying front cone 144 indicates that patient 12 is lying chest down, and inverted cone 146 indicates that patient 12 is in an inverted position. Other cones may be provided, e.g., to indicate that patient 12 is lying on the right side or left side. For example, a lying right posture cone and a lying left posture cone positioned outside of the sagittal plane illustrated in FIG. 8A. In particular, the lying right and lying left posture cones may be positioned in a coronal plane substantially perpendicular to the sagittal plane illustrated in FIG. 8A. For ease of illustration, lying right and lying left cones are not shown in FIG. 8A. Additionally, other cones may be provided for intermediate positions between upright and lying down, e.g., to indicate that patient 12 is in a reclining position. For example, a reclining posture cone may be positioned in the region between the upright posture cone and the lying posture cone.

Vertical axis 141 and horizontal axis 143 are provided for orientation of posture state space 140, and are shown as orthogonal for purposes of illustration. However, posture cones may have respective posture reference coordinate vectors that are not orthogonal in some examples. For example, individual reference coordinate vectors for cones 142 and 146 may not share the same axis, and reference coordinate vectors for cones 144 and 148 may not share the same axis. Also, reference coordinate vectors for cones 144 and 148 may or may not be orthogonal to reference coordinates vectors for cones 142, 146. Therefore, although orthogonal axes are shown in FIG. 8A for purposes of illustration, respective posture cones may be defined by individualized reference coordinate vectors for the cones.

IMD 14 may monitor the posture state parameter value of the posture state sensor to produce a sensed coordinate vector and identify the current posture of patient 12 by identifying the cone in which the sensed coordinated vector of the posture state sensor module 86 resides. For example, if the posture state parameter value corresponds to a sensed coordinate vector that falls within lying front cone 144, IMD 14 determines that patient 12 is lying down on their chest. IMD 14 may store this posture information as a determined posture state or as raw output from the posture state sensor, change therapy according to the posture, or both. Additionally, IMD 14 may communicate the posture information to patient programmer 30 so that the patient programmer can present a posture state indication to patient 12.

In addition, posture state space 140 may include hysteresis zones 150A, 150B, 150C, and 150D (collectively "hysteresis zones 150"). Hysteresis zones 150 are positions within posture state space 140 where no posture zones have been defined. Hysteresis zones 150 may be particularly useful when IMD 14 utilizes the posture state information and posture zones to adjust therapy automatically. If the posture state sensor indicates that patient 12 is in upright cone 142, IMD 14 would not detect that patient 12 has entered a new posture cone until the posture state parameter value indicates a different posture cone. For example, if IMD 14 determines that patient 12 moves to within hysteresis zone 150A from upright cone 142, IMD 14 retains the posture as upright. In this manner, IMD 14 does not change the corresponding therapy until patient 12 fully enters a different posture cone. Hysteresis zones 150 prevent IMD 14 from continually oscillating between different therapies when patient 12's posture state resides near a posture cone boundary. In one example, for certain patients and/or certain conditions and therapies, instead of hysteresis zones, the zones between the upright posture and lying postures may be defined as a reclining posture zone. For example, the IMD 14 may determine that patient 12 moves to within zone 150A, and depending on other parameters such as, for example, how long patient 12 stays within zone 150A, IMD 14 may determine that patient 12 is in the reclining position, and may apply a therapy corresponding to the reclining posture. In other examples, IMD 14 may determine based on the amount of time the patient is in the reclining position that patient 12 may be in a transition between the upright posture and a lying posture, and may treat zone 150A as it would a hysteresis zone.

While the example of IMD 14 is utilized, it should be understood that the techniques discussed above may be similarly used by other medical devices such as, for example, IMD 26. Additionally, as previously noted, while the specific example of posture cones is used in this disclosure, it should be understood that posture cones are illustrative of posture zones, which may be defined by any one of different volumetric shapes.

Each posture cone 142, 144, 146, 148 may be defined by an angle or cosine value in relation to a reference coordinate vector defined for the respective posture cone. Alternatively, some posture cones may be defined by an angle or cosine value relative to a reference coordinate vector for another posture cone. For example, lying postures may be defined by an angle with respect to a reference coordinate vector for an upright posture cone. In each example, as described in further detail below, each posture cone may be defined by an angle in relation to a reference coordinate posture vector defined for a particular posture state. The reference coordinate vector may be defined based on posture sensor data generated by a posture state sensor while patient 12 occupies a particular posture state desired to be defined using the reference coordinate vector. For example, a patient may be asked to occupy a posture so that a reference coordinate vector can be sensed for the respective posture. In this manner, vertical axis 141 may be specified according to the patient's actual orientation. Then, a posture cone can be defined using the reference coordinate vector as the center of the cone.

Vertical axis 141 in FIG. 8A may correspond to a reference coordinate vector sensed while the patient was occupying an upright posture state. Similarly, a horizontal axis 143 may correspond to a reference coordinate vector sensed while the patient is occupying a lying posture state. A posture cone may be defined with respect to the reference coordinate vector. Although a single axis is shown extending through the upright and inverted cones 142, 146, and another single axis is shown extending through the lying down and lying up cones 144, 148, individual reference coordinate vectors may be used for respective cones, and the reference coordinate vectors may not share the same axes, depending on differences between the reference coordinate vectors obtained for the posture cones.

Posture cones may be defined by the same angle or different angles, symmetrical to either axis, or asymmetrical to either axis. For example, upright cone 142 may have an angle of eighty degrees, +40 degrees to −40 degrees from the positive vertical axis 141. In some examples, lying cones may be defined relative to the reference coordinate vector of the upright cone 142. For example, lying up cone 148 may have an angle of eighty degrees, −50 degrees to −130 degrees from the positive vertical axis 141. Inverted cone 146 may have an angle of eighty degrees, −140 degrees to +140 degrees from vertical axis 141. In addition, lying down cone 144 may have an angle of eighty degrees, +50 degrees to +130 degrees from the positive vertical axis 141. In other examples, each posture cone may have varying angle definitions, and the angles may change during therapy delivery to achieve the most effective therapy for patient 12.

Alternatively or additionally, instead of an angle, posture cones 144, 146, 148, 148 may be defined by a cosine value or range of cosine values in relation to vertical axis 141, horizontal axis 143, or some other axis, such as, e.g., individual reference coordinate vectors for the respective cones. For example, a posture cone may be defined by a cosine value that defines the minimum cosine value, calculated using a reference coordinate vector and a respective coordinate vector sensed by a posture state sensor at any point in time. In the cosine computation, the value (adjacent/hypotenuse) can be computed using the magnitude of the coordinate reference vector as the adjacent and a vector at the outermost extent of the cone as the hypotenuse to define a range of cosine values consistent with the outer bound of the cone.

For upright cone 142, the cosine range may extend from the maximum cosine value of 1.0, corresponding to a sensed vector that matches the reference coordinate vector of the upright cone, to a minimum cosine value that corresponds to a sensed vector at the outer limit of the upright cone. As another example, for lying cone 144, the cosine range may extend from the maximum cosine value of 1.0, corresponding to a sensed vector that matches the reference coordinate vector of the lying cone, to a minimum cosine value that corresponds to a sensed vector at the outer limit of the lying cone. Alternatively, the lying cone 144 may be defined with reference to the upright cone 142, such that the cosine range may extend between a maximum and minimum values determined relative to the reference coordinate vector for the upright cone.

In other examples, posture state space 140 may include additional posture cones than those shown in FIG. 8A. For example, a reclining cone may be located between upright cone 142 and lying back cone 148 to indicate when patient 12 is reclining back (e.g., in a dorsal direction). In this position, patient 12 may need a different therapy to effectively treat symptoms. Different therapy programs may provide efficacious therapy to patient 12 when patient 12 is in each of an upright posture (e.g., within upright cone 142), lying back posture (e.g., within lying back cone 148), and a reclining back posture. Thus, a posture cone that defines the reclining back posture may be useful for providing efficacious posture-responsive therapy to patient 12. In other examples, posture state space 140 may include fewer posture cones than cones 142, 144, 146, 148 shown in FIG. 8A. For example, inverted cone 146 may be replaced by a larger lying back cone 148 and lying front cone 144. In other examples, posture zones within a posture space may be defined using one or more different volumetric shapes. For example, some of the posture zones may be defined using cones, while other posture zones may be defined using a toroid.

FIG. 8B illustrates an example posture state space 152 that is a three-dimensional space in which the posture state parameter value from the posture state sensor is placed in relation to the posture zones (e.g., posture cones). Posture state space 152 is substantially similar to posture state space 140 of FIG. 8A. However, the posture state parameter value derived from all three axes of a 3-axis accelerometer may be used to accurately determine the posture state of patient 12. In the example of FIG. 8B, posture state space 152 includes upright cone 154, lying back cone 156, and lying front cone 158. Posture state space 152 also includes hysteresis zones (not shown) similar to those of posture state space 140. In the example of FIG. 8B, the hysteresis zones are the spaces not occupied by a posture cone, e.g., upright cone 154, lying back cone 156, and lying front cone 158. In one example, instead of the hysteresis zones, there may be another posture cone in the space between the upright cone 154 and the lying cones 156 and 158, representing the reclining posture.

Posture cones 154, 156 and 158 also are defined by a respective center line 153A, 153B, or 153C, and associated cone angle A, B or C. For example, upright cone 154 is defined by center line 153A that runs through the center of upright cone 154. Center line 153A may correspond to an axis of the posture state sensor or some other calibrated vector. In some examples, each center line 153A, 153B, 153C may correspond to a posture reference coordinate vectors defined for the respective postures, e.g., the upright posture. For instance, assuming that patient 12 is standing, the DC portion of the x, y, and z signals detected by the posture state sensor of posture state module 86 define a posture vector that corresponds to center line 153A.

The x, y, and z signals may be measured while patient 12 is known to be in a specified position, e.g., standing, and the measured vector may be correlated with the upright posture state. Thereafter, when the DC portions of the posture state sensor signal are within some predetermined cone tolerance or proximity, e.g., as defined by an angle, distance or cosine value, of the posture reference coordinate vector (i.e., center line 153A), it may be determined that patient 12 is in the upright posture. In this manner, a sensed posture coordinate vector may be initially measured based on the output of one or more posture state sensors of posture state module 86, associated with a posture state, such as upright, as a reference coordinate vector, and then later used to detect a patient's posture state.

As previously indicated, it may be desirable to allow some tolerance to be associated with a defined posture state, thereby defining a posture zone using a cone or other volumetric shapes. For instance, in regard to the upright posture state, it may be desirable to determine that a patient who is upright but leaning slightly is still in the same upright posture state. Thus, the definition of a posture state may generally include not only a posture reference coordinate vector (e.g., center line 153A), but also a specified tolerance. One way to specify a tolerance is by providing an angle, such as cone angle A, relative to coordinate reference vector 153A, which results in posture cone 154 as described herein. Cone angle A is the deflection angle, or radius, of upright cone 154. The total angle that each posture cone spans is double the cone angle. The cone angles A, B, and C may be generally between approximately 1 degree and approximately 70 degrees. In other examples, cone angles A, B, and C may be between approximately 10 degrees and 30 degrees. In the example of FIG. 8B, cone angles A, B, and C are approximately 20 degrees. Cone angles A, B, and C may be different, and center lines 153A, 153B, and 153C may not be orthogonal to each other.

In some examples, a tolerance may be specified by a cosine value or range of cosine values. The use of cosine values, in some examples, may provide substantial processing efficiencies. As described above, for example, a minimum cosine value, determined using the reference coordinate vector as adjacent and sensed coordinate vector as hypotenuse, indicates the range of vectors inside the cone. If a sensed coordinate vector, in conjunction with the reference coordinate vector for a posture cone, produces a cosine value that is less than the minimum cosine value for the posture cone, the sensed coordinate vector does not reside within the pertinent posture cone. In this manner, the minimum cosine value may define the outer bound of a range of cosine values within a particular posture cone defined in part by a reference coordinate vector.

While center lines 153A, 153B, 153C of each of the posture cones 154, 156, 158, respectively, are shown in FIG. 8B as being substantially orthogonal to each other, in other examples, center lines 153A, 153B, and 153C may not be orthogonal to each other. Again, the relative orientation of center lines 153A, 153B, 153C may depend on the actual reference coordinate vector output of the posture state sensor of posture state module 86 of IMD 14 when patient 12 occupies the respective postures.

In some examples, all of the posture zones (e.g., cones) may be individually defined based on actual reference coordinate vectors. Alternatively, in some examples, some posture zones may be defined with reference to one or more reference coordinate vectors for one or more other posture zones. For example, lying reference coordinate vectors could be assumed to be orthogonal to an upright reference coordinate vector. Alternatively, lying reference coordinate vectors could be individually determined based on sensed coordinate vectors when the patient is in respective lying postures. Hence, the actual reference coordinate vectors for different postures may be orthogonal or non-orthogonal with respect to one another, and need not reside within the same plane.

In addition to upright cone 154, lying back cone 156, and lying front cone 158, posture state space 152 may include additional posture cones or zones defined by other volumetric shapes. For example, a lying right cone may be provided to define a patient posture in which patient 12 is lying on his right side and a lying left cone may be provided to define a patient posture in which patient 12 is lying on his left side. In some examples, the lying right cone and lying left cone may be positioned approximately orthogonal to upright cones 154, in approximately the same plane as lying back cone 156 and lying front cone 158. Moreover, posture state space 152 may include an inverted cone positioned approximately opposite of upright cone 154. Such a cone indicates that the patient's posture is inverted from the upright posture, i.e., upside down.

In some examples, to detect the posture state of a patient, posture state module 86 of IMD 14 may determine a sensed coordinate vector based on the posture sensor data generated by one or more posture state sensors, and then analyze the sensed coordinate vector with respect to posture cones 154, 156, 158 of FIG. 8B. In an example in which a posture cone is defined by a reference coordinate vector and a tolerance angle, e.g., tolerance angle "A," posture state module 86 may determine whether the sensed coordinate vector is within upright posture cone 154 by calculating the angle between the sensed coordinate vector and reference coordinate vector, and then determine whether the angle is less than the tolerance angle "A." If so, posture state module 86 determines that the sensed coordinate vector is within upright posture cone 154 and detects that patient 12 is in the upright posture. If posture state module 86 determines that sensed coordinate vector is not within upright posture cone 154, posture state module 86 detects that patient 12 is not in the upright posture.

Posture state module 86 may analyze the sensed coordinate vector in posture state space 152 with respect to each individual defined posture zone (e.g., cone), such as posture cones 156 and 158, in such a manner to determine the posture state of patient 12. For example, posture state module 86 may determine the angle between the sensed coordinate vector and reference coordinate vector of individual posture cones defined for the posture state, and compare the determined angle to the tolerance angle defined for the respective posture cone. In this manner, a sensed coordinate vector may be evaluated against each posture zone (e.g., cone) until a match is detected, i.e., until the sensed coordinate vector is found to reside in one of the posture zones. Hence, a zone-by-zone analysis is one option for posture detection.

In other examples, different posture detection analysis techniques may be applied. For example, instead of testing a sensed coordinate vector against posture zones on a zone-by-zone basis, a phased approach may be applied where the sensed coordinate vector is classified as either upright or not upright. In this example, if the sensed coordinate vector is not in the upright zone, posture state module 86 may determine whether the sensed coordinate vector is in a lying posture, either by testing the sensed coordinate vector against individual lying posture zones or testing the sensed coordinate vector against a generalized lying posture volume, such as a donut- or toroid-like volume that includes all of the individual lying posture zones, and may be defined using an angle or cosine range relative to the upright vector, or relative to a modified or virtual upright vector as will be described. In some examples, if lying postures are defined by cones, the lying volume could be defined as a logical OR of the donut- or toroid-like volume and the volumes of the lying posture cones. If the cones are larger such that some portions extend beyond the lying volume, then those portions can be added to the lying volume using the logical OR-like operation.

If the sensed coordinate vector resides within the donut- or toroid-like lying volume, then the sensed coordinate vector may be tested against each of a plurality of lying posture zones in the lying volume. Alternatively, the posture detection technique may not use individual lying zones. Instead, a posture detection technique may rely on a proximity test between the sensed coordinate vector and each of the reference coordinate vectors for the respective lying postures. The proximity test may rely on angle, cosine value or distance to determine which of the lying posture reference coordinate vectors is closest to the sensed coordinate vector. For example, the reference coordinate vector that produces the largest cosine value with the sensed coordinate vector as hypotenuse and the reference coordinate vector as adjacent is the closest reference coordinate vector. In this example, the lying posture associated with the reference coordinate vector producing the largest cosine value is the detected posture. Hence, there are a variety of ways to detect posture, such as using posture cones, using an upright posture cone with lying volume and lying posture cone test, or using an upright posture cone with lying volume and lying vector proximity test.

As a further illustration of an example posture detection technique, posture state module 86 may first determine whether patient 12 is generally in a lying posture state or upright posture state by analyzing the sensed coordinate vector in posture state space 152 with respect to an axis 153A for the upright posture state. Axis 153A may correspond to the upright reference coordinate vector. For example, angle "A" may be used to define upright posture cone 154, as described above, and angles "D" and "E" may be used to define the vector space in which patient 12 may be generally considered to be in the lying posture state, regardless of the particular posture state zone, e.g., lying front cone 158, lying back cone 156, lying right cone (not shown), or lying left cone (not shown), in which the sensed coordinate vector falls.

If it is determined that a sensed coordinate vector is not within an angle A of the axis 153A, then it may be determined that the patient is not in the upright posture indicated by the upright posture cone. In this example, it may next be determined whether a sensed coordinated vector is generally in a lying posture zone volume, which may be considered somewhat donut- or toroid-like, and may be defined relative to the upright reference coordinate vector 153A. As shown, angles "D" and "E" define the minimum and maximum angle values, respectively, that a sensed vector may form with respect to axis 153A of patient 12 for a determination to be made that the patient is generally in the lying posture state. Again, cosine values may be used instead of angles to determine the positions of sensed coordinate vectors relative to posture zones (e.g., cones or other posture volumes), or relative to reference coordinate vectors.

As illustrated, angles "D" and "E" may be defined with respect to vertical axis 153A (which may correspond to an upright reference coordinate vector), which is the reference coordinate vector for the upright posture cone, rather than with respect to a reference coordinate vector of a lying posture state cone. If a sensed vector is within the angular range of D to E, relative to axis 153A, then it can be determined by posture state module 86 that the patient is generally in a lying posture. Alternatively, in some examples, an angle C could be defined according to a generally horizontal axis 153C (which may correspond to one of the lying reference coordinate vectors). In this example, if a sensed vector is within angle C of axis 153C, it can be determined by posture state module 86 that the patient is in a lying posture. In each example, the zone generally defining the lying posture state may be referred to by it shape, e.g., a posture cone, posture donut, or posture toroid. The posture donut may generally encompass a range of vectors that are considered to be representative of various lying down postures (e.g., lying down facing right, lying down facing left, lying down facing front, and so forth).

As an alternative, posture state module 86 may rely on cosine values or a range of cosine values to define the posture zone with respect to axis 153A. When the sensed vector falls within the vector space defined by axis 153A and angles "D" and "E", or produces a cosine value with the reference coordinate vector 153A in a prescribed range, posture state module 86 may determine that patient 12 is generally in a lying posture state. For example, if the sensed vector and reference coordinate vector 153 produce a cosine value in a first range, the posture is upright. If the cosine value is in a second range, the posture is lying. If the cosine value is outside of the first and second ranges, the posture may be indeterminate. The first range may correspond to the range of cosine values that would be produced by vectors in posture zone (e.g., cone) 154 defined by angle A, and the second range may be correspond to cosine values that would be produced by vectors in the posture zone (e.g., donut) defined by angles D and E.

When the sensed vector fall within the vector space defined by axis 153A and angles "D" and "E", as indicated by angle or cosine value, posture state module 86 may then determine the particular lying posture state occupied by patient 12, e.g., lying front, lying back, lying right, or lying left. To determine the particular lying posture state occupied by patient 12, posture state module 86 may analyze the sensed vector with respect to reference coordinate vectors for individual lying posture state zones, e.g., lying front cone 156, lying back cone 158, lying right cone (not shown), and lying left cone (not shown), using one more techniques previously described, such as angle or cosine techniques. For example, posture state module 86 may determine whether the sensed coordinated vector resides within one of the lying posture state zones and, if so, select the posture state corresponding to that zone as the detected posture state.

FIG. 8C illustrates an example posture state space 155 that is a three-dimensional space substantially similar to posture state space 152 of FIG. 8B. Posture state space 155 includes upright posture zone 157 represented by a cone and defined by reference coordinate vector 167. The tolerance that defines upright posture zone 157 with respect to reference coordinate vector 167 may include a tolerance angle or cosine value, as described above. In contrast to determining whether a sensed coordinate vector resides in a lying zone, FIG. 8C illustrates a method for detecting a lying posture based on proximity of a sensed coordinate vector to one of the reference coordinate vectors for the lying postures.

As shown in FIG. 8C, posture state space 155 includes four reference coordinate vectors 159, 161, 163, 165, which are associated with lying left, lying right, lying front, and lying back posture states, respectively. Posture state module 86 may have defined each of the four reference coordinated vector 159, 161, 163, 165 based on the output of one or more posture sensors while patient 12 occupied each of the corresponding posture states. Unlike lying front and lying back posture zones 158, 156 in the example of FIG. 8B, the posture state reference data for the four defined posture states corresponding to reference vectors 159, 161, 163, 165 need not include angles defined relative to the respective reference vector in a manner that defines a posture zone. Rather, as will be described below, the respective posture state reference vectors may be analyzed with respect to one another in terms of cosine values to determine which particular reference coordinate vector is nearest in proximity to a sensed coordinate vector.

In some examples, to determine the posture state of patient 12, posture state module 85 may determine whether a sensed coordinate vector is within upright posture zone (e.g., cone) 157 by analyzing the sensed coordinate vector in view of the tolerance angle or cosine value(s) defined with respect to upright posture reference coordinate vector 167, or whether the sensed vector is within a posture zone (e.g., donut or toroid) defined by a range of angles (as in FIG. 8B) or cosine values with respect to upright posture reference coordinate vector 167, in which case posture state module 86 may determine that patient 12 is in a general lying posture state.

If posture state module 86 determines that patient 12 is occupying a general lying posture state, posture state module 86 may then calculate the cosine value of the sensed coordinate vector with respect to each lying reference coordinate vectors 159, 161, 163, 165. In such an example, posture state module 86 determines the particular lying posture state of patient 12, i.e., lying left, lying right, lying front, lying back, based on which cosine value is the greatest of the four cosine values. For example, if the cosine value calculated with the sensed vector as the hypotenuse and the lying front reference vector 163 as the adjacent vector is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

In some examples, posture state module 86 may determine whether patient 12 is generally in a lying posture state based on the relationship of a sensed vector to upright reference vector 167. For example, as described above, a lying posture zone (e.g., donut or toroid) may be defined with respect to upright posture reference vector 167, e.g., using angles D and E as in FIG. 8B. Such a technique may be appropriate when lying posture reference vectors 159, 161, 163, 165 define a common plane substantially orthogonal to upright posture reference vector 167. However, the lying posture reference vectors 159, 161, 163, 165 may not in fact be orthogonal to the upright reference coordinate vector 167. Also, the lying posture reference vectors 159, 161, 163, 165 may not reside in the same plane.

To account for non-orthogonal reference vectors, in other examples, a lying posture zone (e.g., donut or toroid) may be defined with respect to a modified or virtual upright reference vector 169 rather than that actual upright posture reference vector 167. Again, such a technique may be used in situations in which the lying reference vectors 159, 161, 163, 165 are not in a common plane, or the common plane of reference vector 159, 161, 163, 165 is not substantially orthogonal to upright reference vector 167. However, use of the example technique is not limited to such situations.

To define virtual upright reference vector 169, posture state module 86 may compute the cross-products of various combinations of lying reference vectors 159, 161, 163, 165 and average the cross product values. In the example of FIG. 8C, posture state module 86 may compute four cross products and average the four cross product vectors to yield the virtual upright vector. The cross product operations that may be performed are: lying left vector 159×lying back vector 165, lying back vector 165×lying right vector 161, lying right vector 161×lying front vector 163, and lying front vector 163×lying left vector 159. Each cross product yields a vector that is orthogonal to the two lying reference vectors that were crossed. Averaging each of the cross product vectors yields a virtual upright reference vector that is orthogonal to lying plane 171 approximately formed by lying reference vectors 159, 161, 163, 165.

Using virtual upright reference vector 169, posture state module 86 may define a lying posture zone (e.g., donut or toroid) in a manner similar to that described with respect to upright reference vector 167, but instead with respect to virtual upright reference vector 169. In particular, when posture state module 86 determines that the patient is not in the upright posture, the posture state module determines whether the patient is in a lying posture based on an angle or cosine value with respect to the virtual upright reference vector 169.

Posture state module 86 may still determine whether patient 12 is in an upright posture state using upright posture zone (e.g., cone) 157. If posture state module 86 determines that patient 12 is occupying a general lying posture state based on the analysis of the sensed coordinate vector with respect to virtual upright reference vector 169, posture state module 86 may then calculate the cosine value of the sensed coordinate vector (as hypotenuse) with respect to each lying reference coordinate vectors 159, 161, 163, 165 (as adjacent).

In such an example, posture state module 86 determines the particular lying posture state of patient 12, i.e., lying left, lying right, lying front, lying back, based on which cosine value is the greatest of the four cosine values. For example, if the cosine value calculated with the lying front reference vector 163 is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

Additionally, posture state definitions are not limited to the posture zones discussed above, i.e., cones, donuts, and toroids. For example, a definition of a posture state may involve a posture vector and a tolerance, such as a maximum distance from the posture vector. So long as a detected posture vector is within this maximum distance from the posture vector that is included in the definition of the posture state, patient 12 may be classified as being in that posture state. This alternative method may allow posture states to be detected without calculating angles, as is exemplified above in the discussion related to posture cones.

Further to the foregoing, posture states may be defined that are specific to a particular patient's activities and/or profession. For instance, a bank teller may spend a significant portion of his working day leaning forward at a particular angle. A patient-specific "Leaning Forward" posture state including this angle may be defined. The posture zone for the "Leaning Forward" posture state may be defined, for example, by a cone angle or other tolerance value selected for this posture state that may be specific to the particular posture state definition for this patient. In this manner, the defined posture states may be tailored to a specific user, and need not be "hard-coded" in the IMD.

In some examples, individual posture states may be linked together, thereby tying posture states to a common set of posture reference data and a common set of therapy parameter values. This may, in effect, merge multiple posture zones for purposes of posture state-based selection of therapy parameter values. For example, all lying posture state zones (back, front, left, right) could be treated as one zone (e.g., cone or a donut/toroid) using a technique the same as or similar to that described with respect to FIGS. 8B and 8C to define a donut, toroid or other volume, for example. One program group or common set of therapy parameter values may apply to all posture states in the same merged zone, according to the linking status of the posture states, as directed via external programmer 20.

Merging posture zones or otherwise linking a plurality of posture states together may be useful for examples in which a common set of therapy parameter values provides efficacious therapy to patient 12 for the plurality of posture states. In such an example, linking a plurality of posture states together may help decrease the power consumption required to provide posture-responsive therapy to patient 12 because the computation required to track patient posture states and provide responsive therapy adjustments may be minimized when a plurality of posture states are linked together.

Linking of posture states also may permit a therapy parameter value adjustment in one posture state to be associated with multiple posture states at the same time. For example, the same amplitude level for one or more programs may be applied to all of the posture states in a linked set of posture states. Alternatively, the lying down posture states may all reside within a combination of zones (e.g., donut or toroid) that would be used instead of individual zones (e.g., cones) 156 and 158, for example. The combination of zones (e.g., toroid) may be divided into sectional segments that each correspond to different posture states, such as lying (back), lying (front), lying (right), lying (left) instead of individual zones (e.g., cones). In this example, different posture reference data and therapy parameter values may be assigned to the different sectional segments of the toroid.

FIGS. 9A-9L are conceptual diagrams illustrating example screens 202 and 252 of user interface 200 of an external programmer device for displaying a patient avatar 204 and permitting user manipulation of parameters associated with postures of patient 12 during setup of posture-responsive stimulation therapy for patient 12. For example, a user may utilize interface 200 to size or shape posture state zones relative to the patient avatar, modify transition times between detected posture states, or adjust other parameters associated with posture-responsive stimulation therapy. As discussed above, the programmer device may be in communication with an IMD (e.g., IMD 14 or IMD 26) associated with the patient, where the IMD provides therapy (e.g., electrical stimulation therapy, fluid delivery therapy, or the like) to the patient. The IMD may be configured to deliver the therapy based on the detected posture of the patient, where the posture is detected based on the defined posture state zones.

Figure 9A:
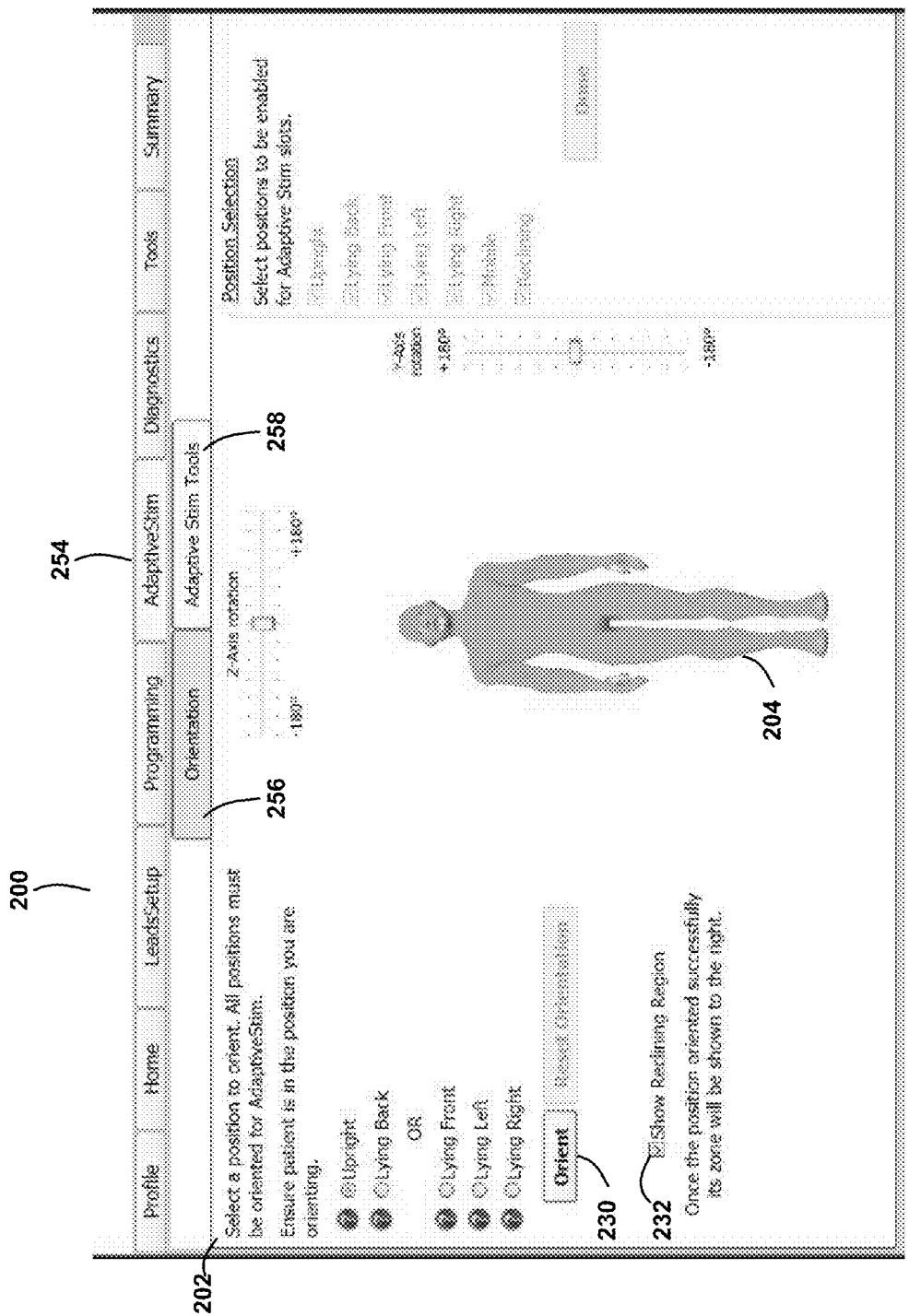
FIGS. 9A-L are conceptual diagrams illustrating example screens of a user interface for displaying an avatar and allowing manipulation of parameters associated with postures of a patient during set up of adaptive stimulation therapy for the patient.

Referring to FIG. 9A, a user may utilize an external device, such as, for example, programmer 20, 30, or 60 to set up the adaptive stimulation. When connected to a patient 12, a user interface 200 may allow the user to choose a tab associated with the different functionalities that a user may be capable of performing and modifying for therapy for patient 12. For the adaptive stimulation set up, the user may select the "AdaptiveStim" tab, 254, as shown in FIG. 9A, which has sub tabs "Orientation" 256 and "Adaptive Stim Tools" 258. "AdaptiveStim" may provide tools that a user may utilize for programming posture-responsive stimulation therapy. Selecting the "Orientation" tab 256 brings up screen 202. The user may utilize the functionalities in screen 202 to create, define, or adjust posture zones such a posture cones or other volumetric shapes for each of the postures of patient 12, where patient 12 is represented by avatar 204, which resembles the body of a patient relative to the posture zones. As shown in the examples illustrated by FIGS. 9A-9L, the posture zones are represented by cones.

In some examples, the reclining posture may be optional, and the user may be able to select whether to program parameters associated with the reclining posture (also referred to as "position" in the figures). As FIG. 9A illustrates, a user may be able to select or unselect a selection box 232 via user interface 200 to indicate whether or not to show a zone corresponding to the reclining posture.

Orientation of a posture may be performed, for example, during setup of the system (e.g., immediately after implantation of the IMD or if changes subsequently occur to the IMD or the adjustments are made to parameters of the therapy delivered by the IMD). Orientation of the postures may be performed to define posture zones associated with the different posture states that the IMD utilizes to deliver posture-based therapy to the patient. During orientation, while the patient is in a certain posture, information (e.g., sensor data used by posture state module 86 or 98) may be obtained by the IMD and associated with the current posture and a corresponding posture zone. Subsequently, when therapy is delivered, sensor data used by the posture state module may be utilized to determine the corresponding posture state of the patient based on the posture zones defined during orientation.

Figure 9B:
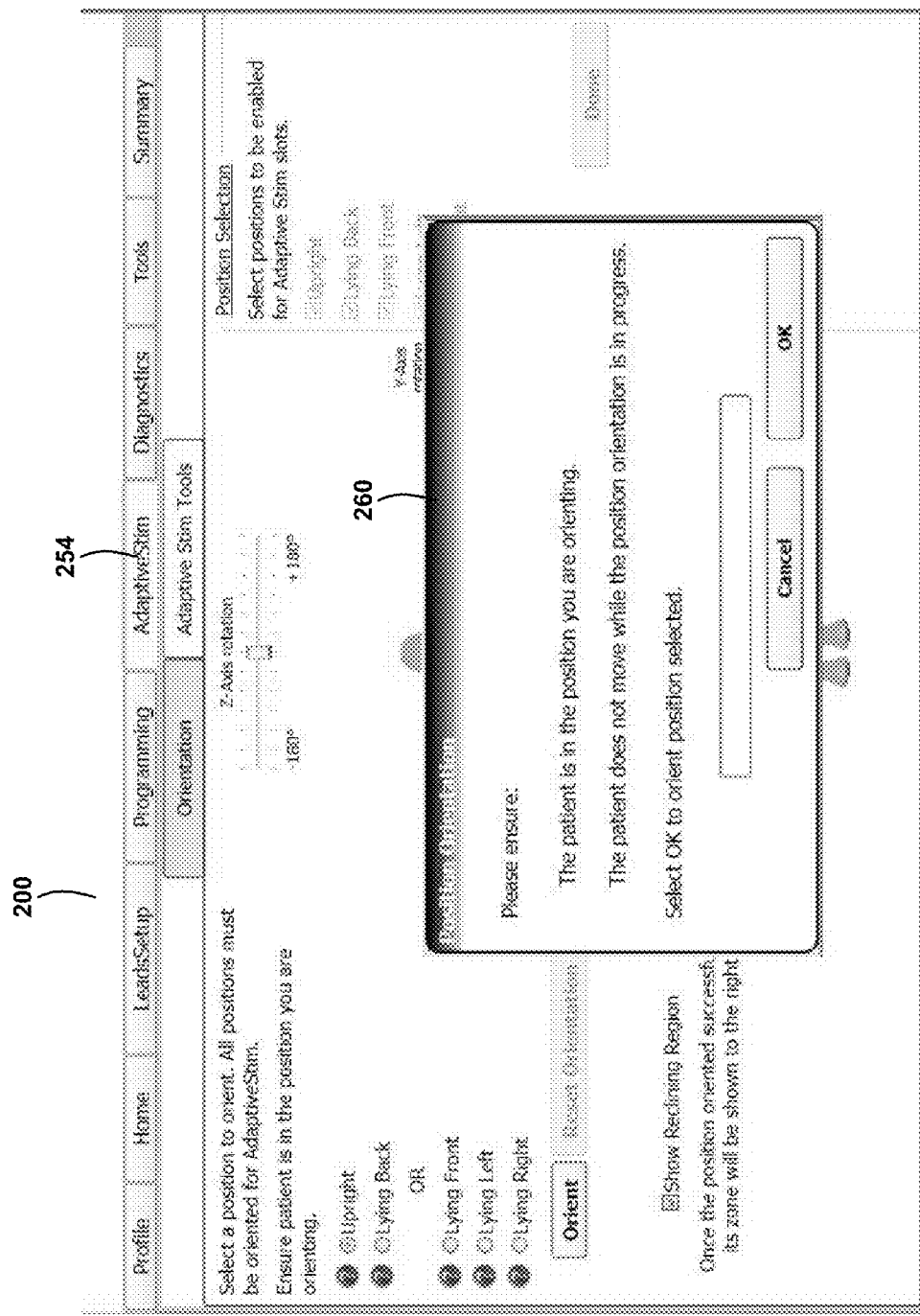

The user may select each of the postures, one-by-one, and click the "orient" button 230 to create the cone associated with the selected posture. For example, the user may begin by selecting "upright" and clicking "orient" to define the cone for the upright posture. As shown in FIG. 9A, the user may need to ensure that the patient is in the posture being oriented, e.g., standing up for the upright posture. When the user clicks the "orient" button 230, a pop up box 260 appears, telling the user to ensure that the patient is in the posture being oriented and to instruct the user not to move during the orientation process, as shown in FIG. 9B. The user may then select "OK" to orient the posture.

Figure 9C:
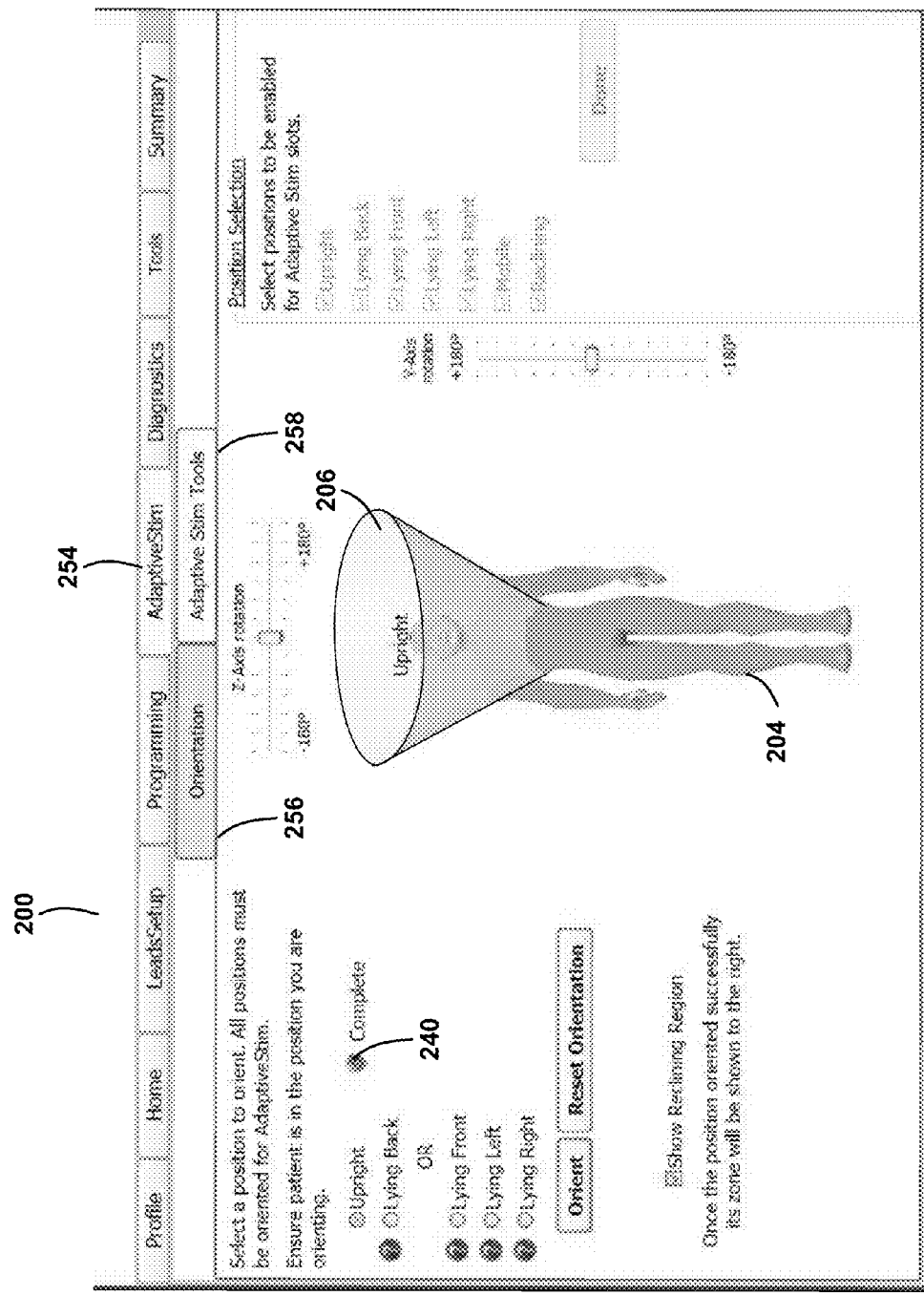

Once oriented, a cone associated with the posture may appear in relation to the avatar 204. For example, when the upright posture is oriented, an upright cone 206 is displayed, as shown in FIG. 9C. Initially, the upright cone 206 may be a default cone defined by data stored by the programmer device (e.g., programmer 20, 30, or 60). An icon indicating completion of orientation for a posture may be displayed when the user completes orientation for the posture. In the example of FIG. 9C, the icon 240 indicates that orientation of the upright posture is completed. During orientation for a posture, a default cone may be displayed to represent the associated posture relative to avatar 204. The user may subsequently manipulate the cones associated with the different postures by modifying their shape, size, or position relative to avatar 204, as described in more detail below.

Figure 9D:
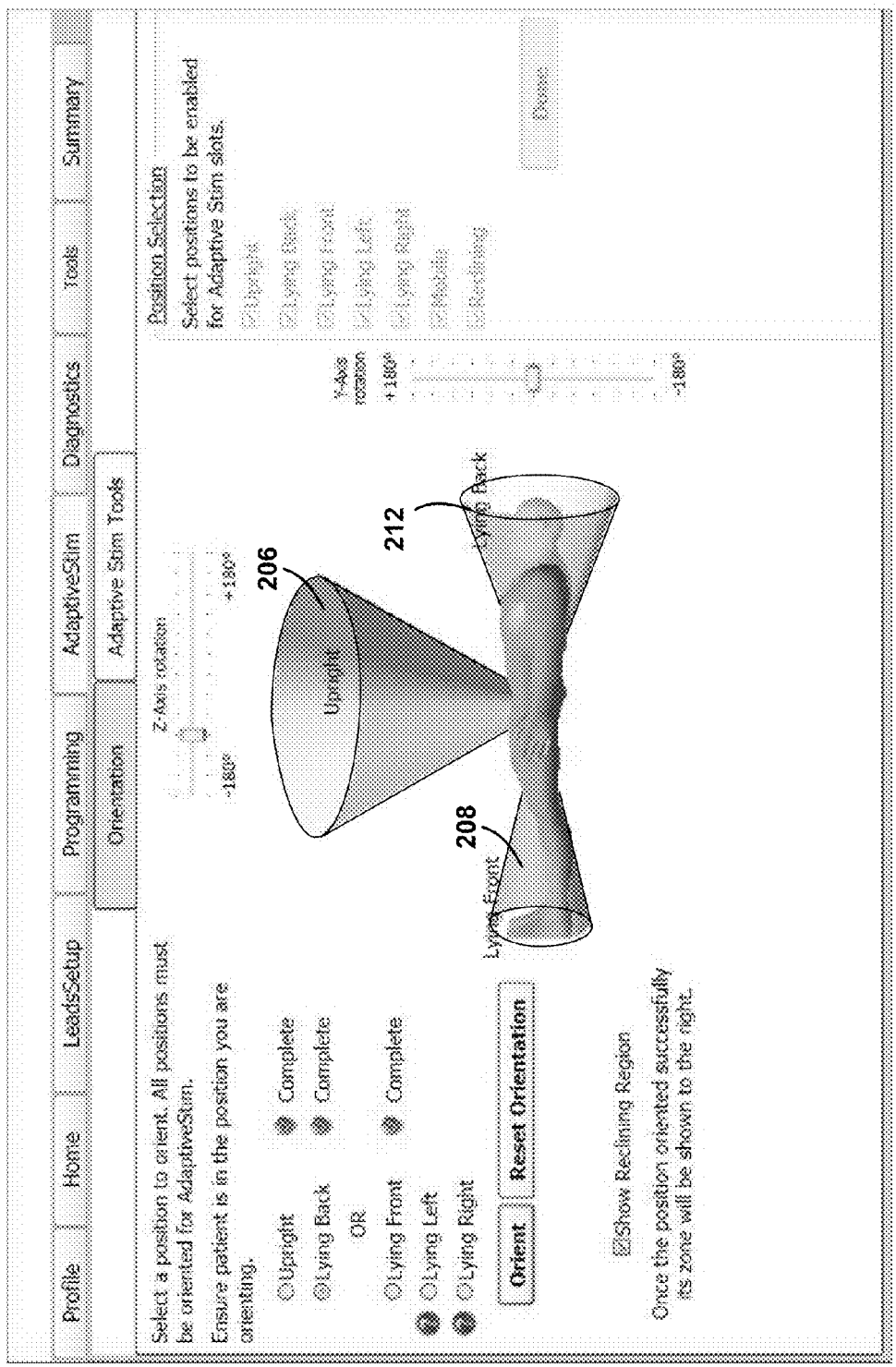
Figure 9E:
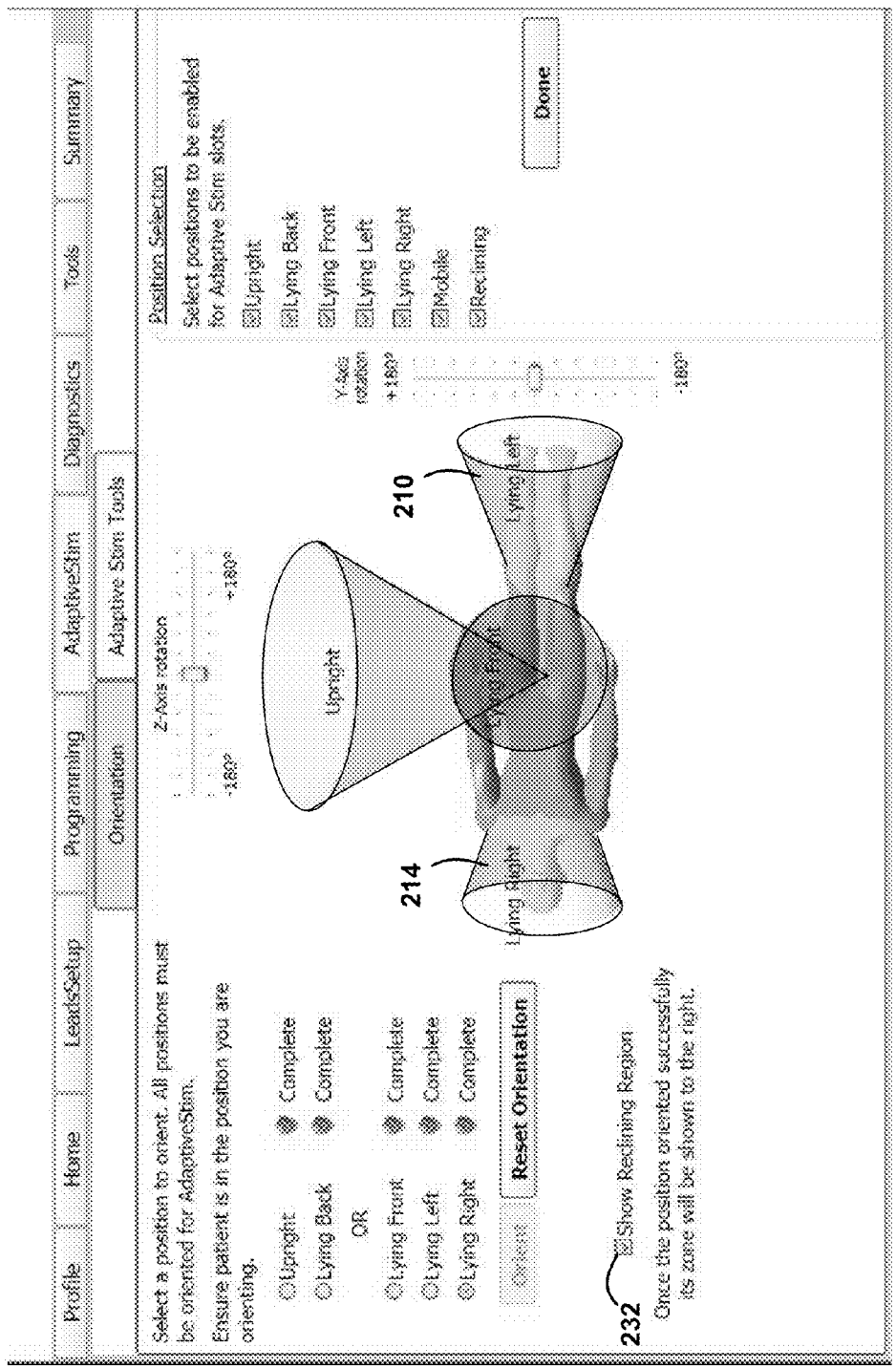

Orientation may then be performed for other postures (e.g., lying front/back indicated by cones 208 and 212, respectively, in FIG. 9D, and lying left/right indicated by cones 210 and 214, respectively, in FIG. 9E) as specified by the user. In some examples, depending on the therapy received by the patient, the reclining posture may or may not require different therapy parameters. As a result, the reclining posture may be optional, and the user may check or uncheck the box 232 to indicate whether or not the reclining posture cone should be displayed. When a reclining posture is not utilized, the corresponding region between the cones associated with the other postures may be considered a hysteresis zone as discussed above in FIG. 8A.

Figure 9F:
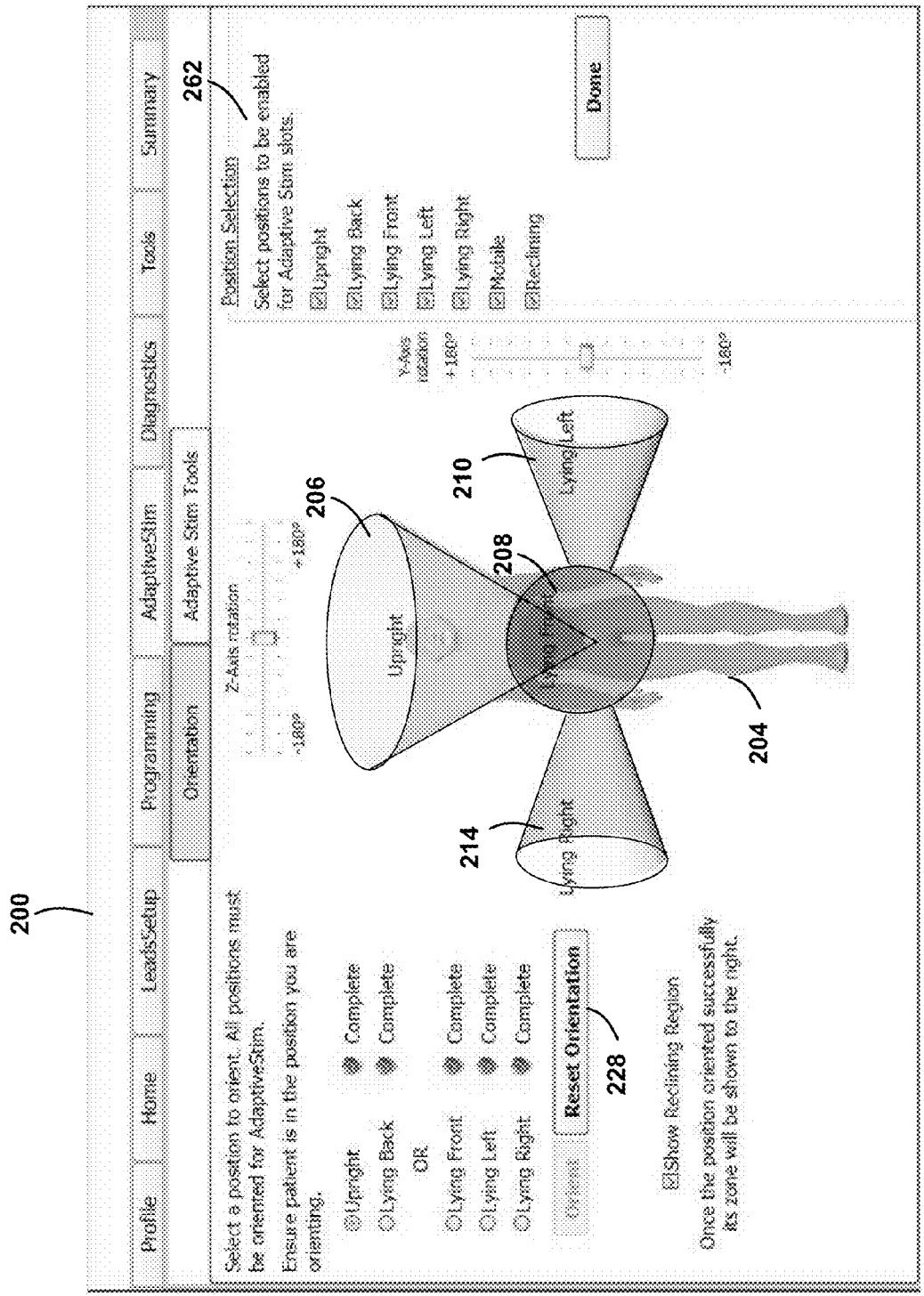
Figure 9G:
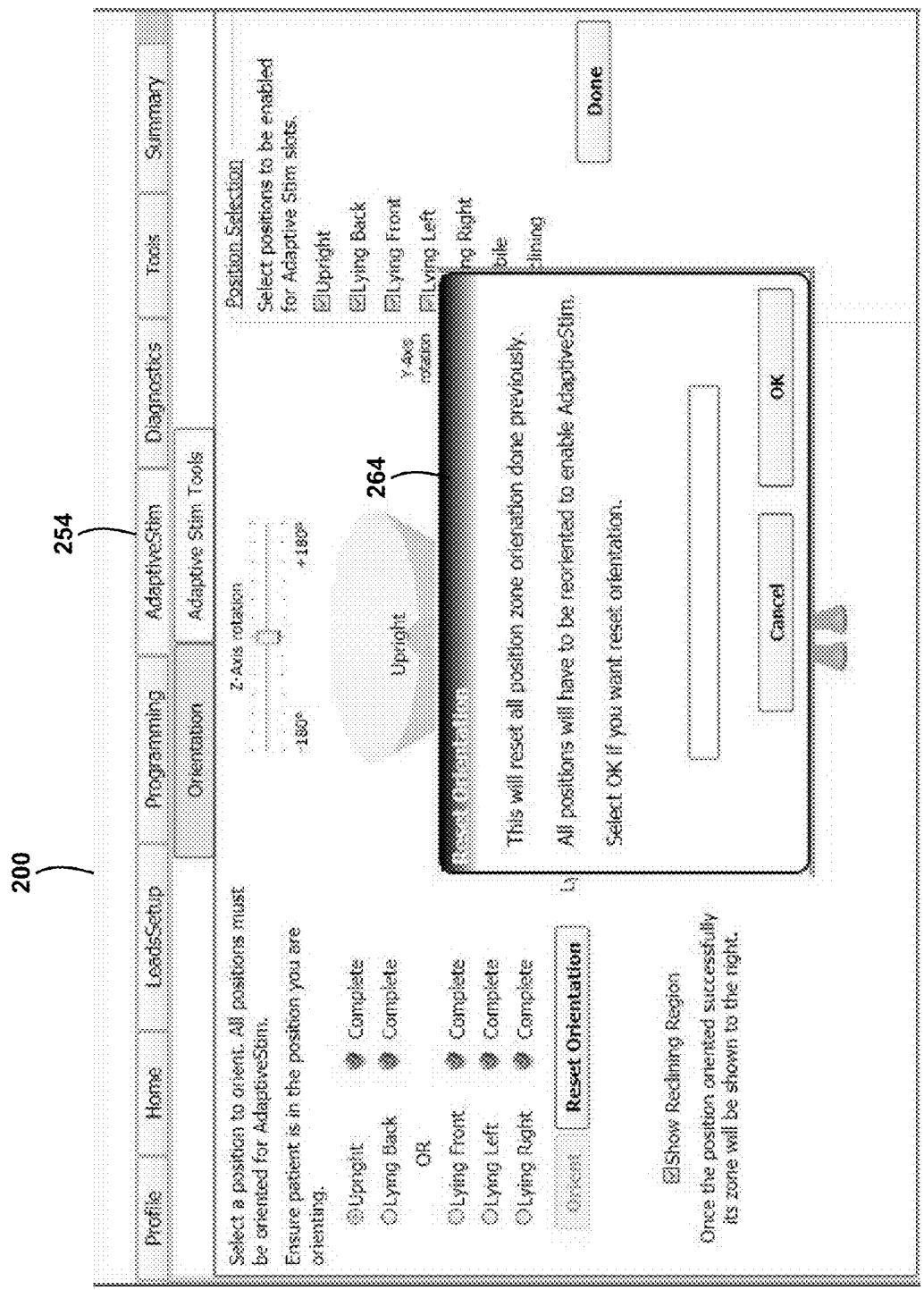

When the user completes orienting all postures, avatar 204 representing the patient may be displayed with all cones as shown in FIG. 9F. The cones displayed following completion of the orientation process may be default cones generated at a default angle around the reference vectors produced when the patient occupies the corresponding postures. Additionally, the user may be able to select the posture states that need to be enabled for the particular therapy being programmed for adaptive stimulation therapy using the selection panel 262. In an example, the user may not be satisfied with the postures and may wish to reorient the posture cones, by selecting the "reset orientation" button 228. Selecting the "reset orientation" button 228, may bring up a pop up message 264, as shown in FIG. 9G, indicating that the user has selected to reset the orientation of the posture states and to select OK if the user wants to reorient the posture states (i.e., obtain sensor readings to redefine the corresponding posture cones) or cancel to resume the previous screen. Selecting OK may cause the programmer device (e.g., programmer 20, 30, or 40) to revert to a screen of user interface 200 similar to the one displayed in FIG. 9A, and the user may then follow the same steps as described above to orient the postures.

Figure 9H:
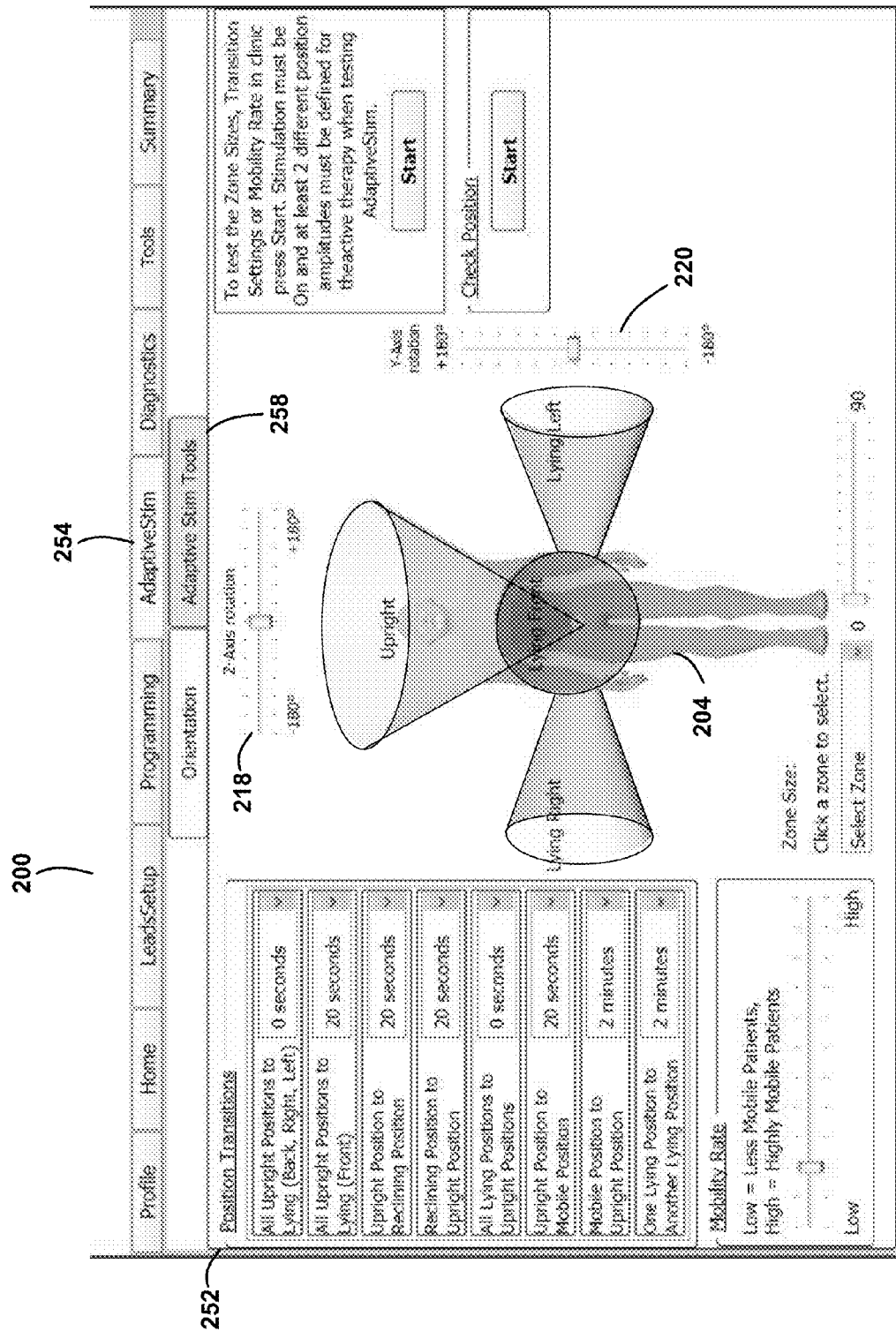
Figure 9I:
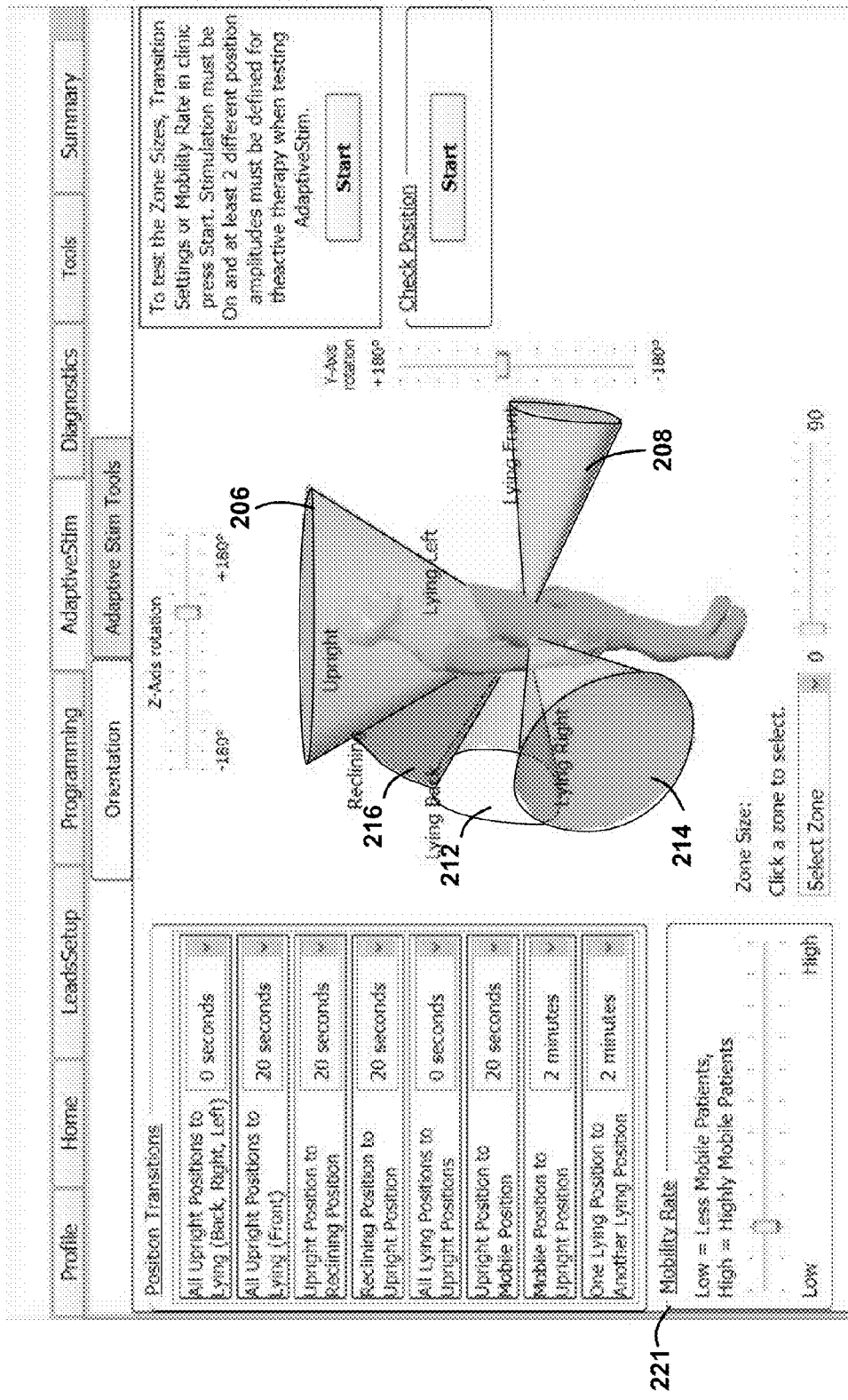

Once the user has oriented the postures to obtain corresponding posture zones, the user may select the "Adaptive Stim Tools" tab 258 to be able to manipulate parameters associated with the posture zones (e.g., cones), as shown in FIG. 9H. Selecting the "Adaptive Stim Tools" tab 258 brings up screen 252, which shows an avatar 204 of the patient, with posture cones representing the posture states upright, lying front, lying left, lying back (not shown), lying right, and reclining (not shown). The screen 202 may also include controls 218 and 220 that control rotation of the avatar 204 of the patient in the z-axis direction and the y-axis direction, respectively. Using controls 218 and 220, the user may rotate the avatar 204 around in the z-axis direction and y-axis direction to be able to spin the avatar and view from different perspectives, for example, to manipulate (e.g., modify the shape, change the size) the cones more easily and effectively. The user may manipulate the z-axis and y-axis rotation controls to rotate the avatar 204 to better view posture cones, such as reclining posture cone 216, as shown in FIG. 9I. The user may also indicate the mobility rate of the patient using mobility rate control 221. The mobility rate of the patient may indicate how mobile a patient is. For example, a patient with a more active lifestyle may have a higher mobility rate than a patient with a less active lifestyle. The mobility rate may be used as a threshold to determine when a posture state of the patient is mobile. For example, for a patient with a higher mobility rate, the threshold to change from the upright posture to the mobile posture may be higher than the threshold to effectuate that change for a patient of a lower mobility rate.

Figure 9J:
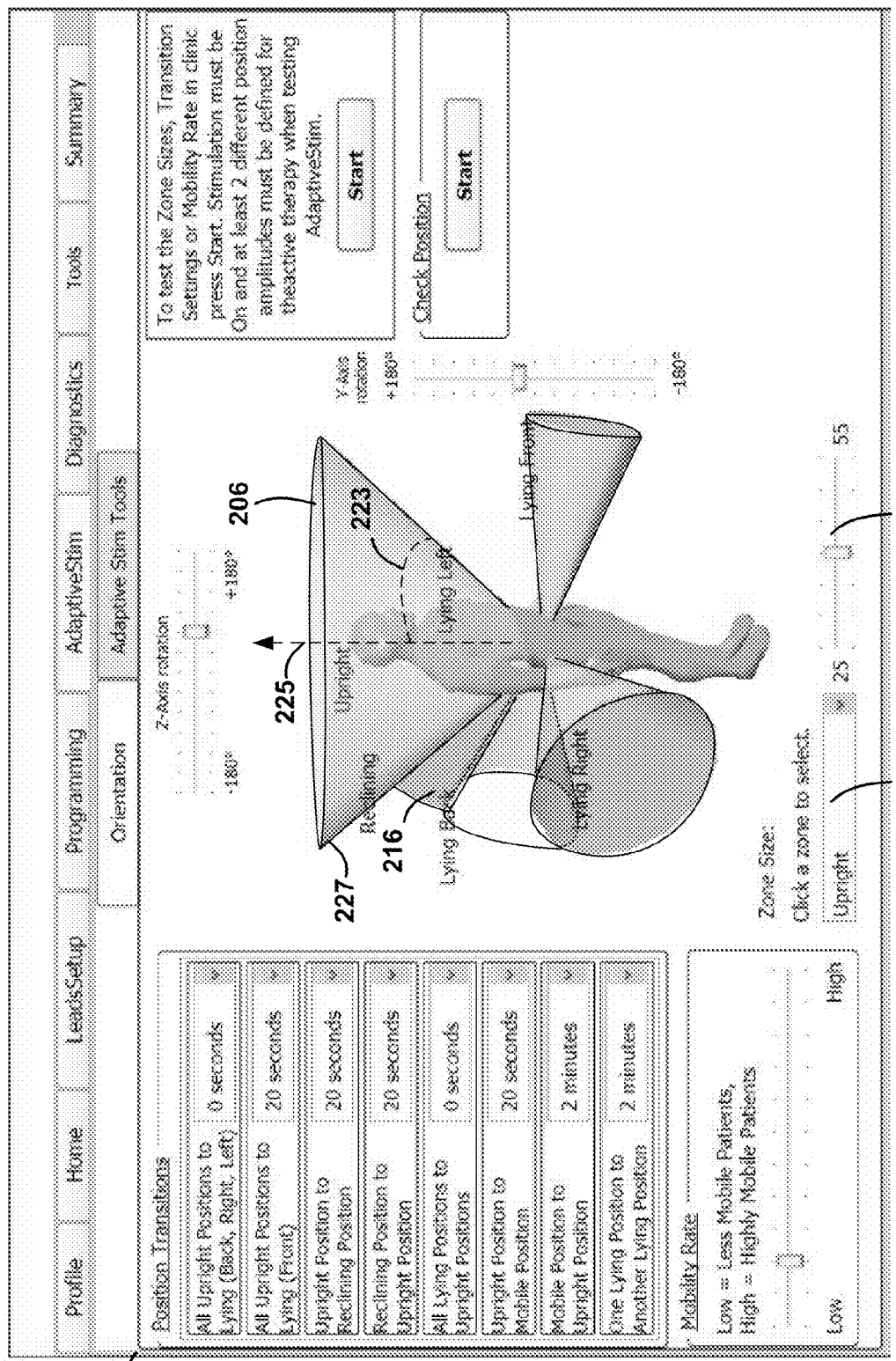

As illustrated in FIG. 9J, a user may wish to manipulate a posture cone by changing the size of the posture cone associated with a posture state, for example, to allow a larger margin for a given posture, to accommodate the size of a patient, or to accommodate the patient's normal stance relative to the implant location and orientation. In one example, the user may use the drop down menu 222 and control 224 to resize a cone of a posture state by changing an angle associated with the cone (e.g., the angle relative to a vector going through the center of the cone) or changing the diameter of the base of the cone, for example. The drop down menu 222 may allow the user to select a cone associated with a posture state, and may list the posture states "upright," "lying front," "lying left," "lying back," "lying right," and "reclining." Once the user selects one of the zones from the drop down menu 222, the corresponding cone may be highlighted or displayed using a color, pattern, or animation, for example, to distinguish it from the remaining cones. For example, if the user selects "upright," cone 206 may be highlighted to indicate the selection made by the user. Once selected, the user may change the size of the selected and highlighted cone by using control 224. Control 224 may indicate the size of the cone, for example, in terms of a range of angle values or cosine values. An angle value may indicate, for example, the angle associated with the cone surface relative to the center vector, as described above. In particular, the angle may be an angle 223, measured from the cone surface relative to a vector 225, that defines the size of the cone. The angle range may have minimum and maximum angle values beyond which a user may not decrease or increase the size of the cone. The minimum and maximum values may ensure that cones of adjacent postures do not have a large overlapping area. The minimum and maximum angles may vary from one posture cone to another. For example, the upright cone 206 may have a larger maximum angle than the reclining posture cone 216.

In another example, a user may select a cone by simply clicking on the graphical representation of the posture cone on the screen 252 and changing the angle using the control 224. In yet another example, the user may select a posture cone using either the drop down menu 222 or by clicking on the posture cone, and change the size of the posture cone by dragging one of the edges (e.g., edge 227) of the posture cone towards the center vector or away from the center vector to shrink or enlarge the posture cone size, respectively. The limits of the size of the posture cone by dragging an edge may correspond to the limits of the angle size of the control 224. In one example, the user may click and drag one edge of the posture cone (e.g., edge 227) to change its size, and the corresponding size change may be symmetric with respect to the center vector (e.g., vector 225). In another example, the user may select a cone and use buttons marked, for example, with "plus" and "minus" signs to increase and decrease the size (e.g., angle 223) of the posture cone, respectively. In another example, the programmer device (e.g., programmer 20, 30, or 40) may respond to touch gestures, and the user may select a posture cone and use a touch gesture to increase/decrease the size of the posture cone. In another example, the user may type in the desired angle or cosine value associated with the angle for a selected posture cone or select a broad generic indication such as, for example, small, medium, large, and extra large.

Figure 9K:
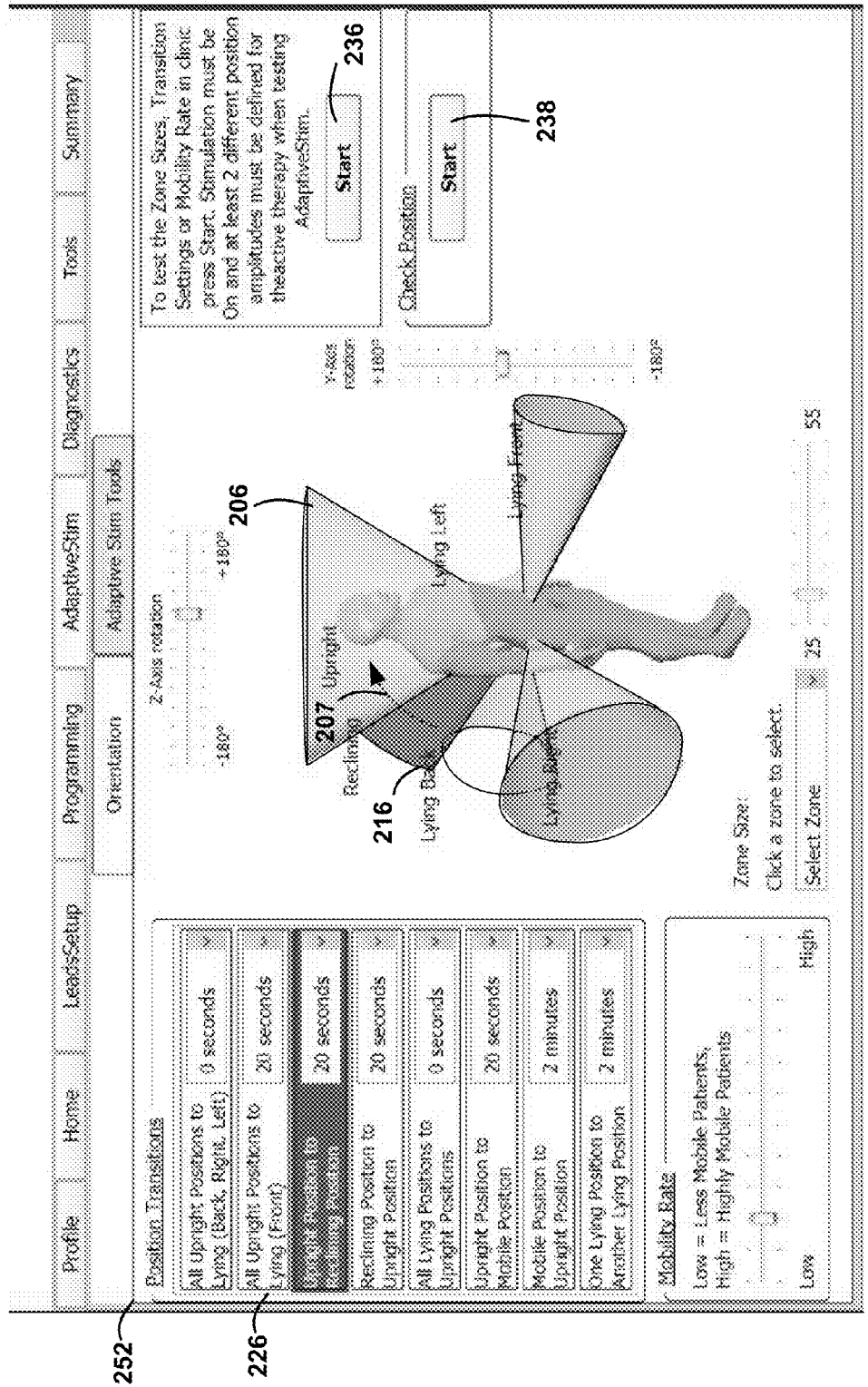
Figure 9L:
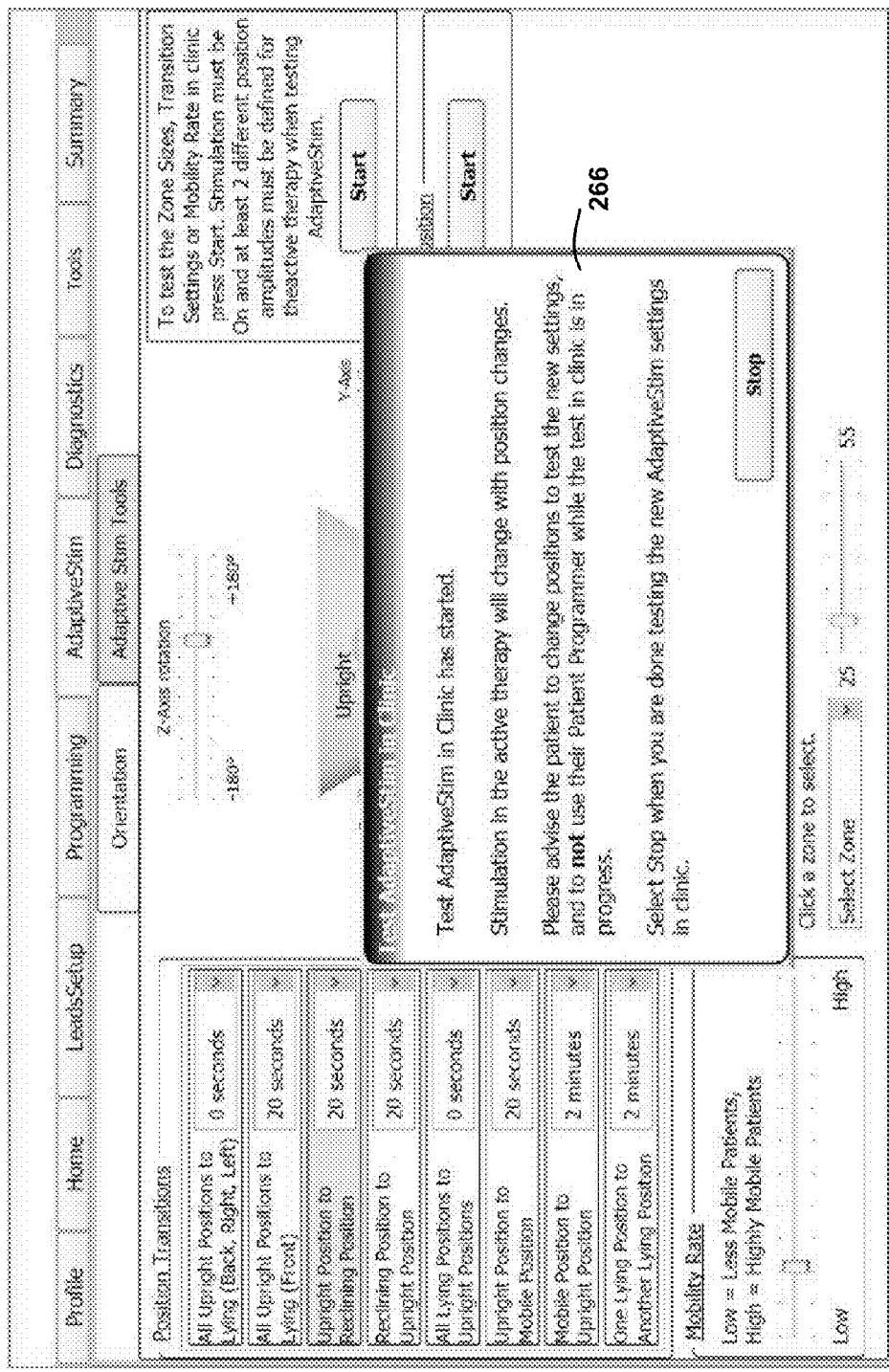

In one example of the disclosure, as illustrated in FIG. 9K, the user may also modify timing parameters associated with posture states. Timing parameters may include, for example, posture state transition times. Posture state transition time, which may be also referred to as dwell time, may be the time needed to recognize transition from one posture to another after a posture change is initially detected. For example, posture detection may detect posture change within a fraction of a second; however, the newly detected posture may be temporary and transient, and therefore, it may not be appropriate to change the applied therapy to that of the newly detected posture. When a new posture is detected, the therapy for the previous posture may be continued until the patient remains in the newly detected posture for an amount of time at least equal to the transition time associated with transitioning from the previous posture to the new posture. In one example, transition times may be set to default values, but may be subsequently altered by a user. As illustrated in FIG. 9K, for example, the transition time from all upright postures to the lying front posture is 20 seconds. Therefore, when a patient is in an upright posture and goes to the lying front posture, once the lying front posture is detected, the therapy applied to the patient remains that of the upright posture, until the patient is in the lying front posture for 20 seconds. Different posture state transitions may have different transition times.

The screen 252 may include a control panel 226 for viewing and modifying posture transition settings. A user may select one of the posture transitions, for example, upright posture to reclining posture, by highlighting it, as shown in FIG. 9K. Selecting a posture transition may cause the display to highlight the two associated posture cones. In this example, the reclining cone 216 and the upright cone 206 may be highlighted to indicate which transition time is being modified by the user. In one example, the starting position cone may be indicated with one color or pattern of colors (e.g., reclining cone 216 displayed in red), or with blinking or flashing patterns, and the end position cone may be indicated with another color or pattern of colors (e.g., upright cone 206 is displayed in green), or with blinking or flashing, for example. In another example, an arrow (e.g., arrow 207) may be displayed indicating the direction of change from the starting position cone to the end position cone. In yet another example, text may be displayed on or around the starting and end posture cones to indicate the direction of change of the currently selected setting. In yet another example, an animation of the avatar 204 going from the starting posture to the end posture may be used to illustrate the selected setting. For example, if the starting posture state is reclining and the end posture state is upright, avatar 204 may be initially displayed in the reclining posture, then moving to the upright posture.

In one example, the starting posture and the end posture may be represented by the same cone. For example, mobile and upright may be both represented by the upright cone 206. In such an example, the cone 206 may flash or display a pattern or text indicating that it is the starting and end posture cone. In the example of going from the upright posture to a mobile (e.g., walking) posture, animation of avatar 204 may be utilized to indicate the change from upright to mobile, by initially displaying avatar 204 in the upright posture, then animating avatar 204 to walk to indicate changing to a walking posture. Other methods of indicating the starting and end postures may be contemplated.

The screen 252 may allow the user to view posture transitions in an alternative manner. For example, instead of displaying all the posture transitions as shown in FIG. 9K, in control panel 226, the user may be presented with drop down menus for the starting posture and the end posture, and may make a selection for each. When the user selects a starting posture, the corresponding cone may flash or get highlighted, and when an end posture is selected, the corresponding posture cone may flash or get highlighted as well. When both postures are selected, an indication pattern may be displayed according to one of the above examples. A third box may indicate the current transition time associated with the two selected postures. The user may then modify the transition time if desired. In one example, parameters associated with the therapy corresponding to the starting and end postures may be displayed on screen 252.

Screen 252 may also display other options for the user to select during set up. For example, the user may select to check a posture state using the "start" button 238, which may determine the patient's current posture and update avatar 204 to display the current posture. In one example, avatar 204 may be displayed in the upright position by default. One or more examples of displaying a patient's current posture state via an external display device are described in co-pending U.S. patent application Ser. No. 12/985,965, titled "DISPLAY OF DETECTED PATIENT POSTURE STATE," and filed on Jan. 6, 2011, the entire content of which is incorporated herein by reference.

Once the user is satisfied with the modifications made (e.g., posture orientation, posture transition modifications, zone (e.g., cone) size modifications, and/or mobility rate modifications, the user may test the modified settings by selecting the "start" button 236. To be able to test the modifications, adaptive stimulation needs to be enabled in the IMD (e.g., IMD 14 or IMD 26) and parameters need to be defined for at least two different postures for the patient's active therapy. A programmer device (e.g., programmer 20, 30, or 40) may be used to activate the IMD (e.g., IMD 14 or IMD 26) and enable adaptive sitmulation. Selecting the "start" button 236 may initiate communication with the IMD to provide the IMD with the updated posture information for adaptive stimulation therapy. Additionally, message 266, shown in FIG. 9L, may be displayed to indicate to the user that the adaptive stimulation testing has started, and to instruct the patient to change postures to test the effectiveness and functionality of the modified settings in detecting posture state changes and applying the appropriate therapy stimulation.

As previously noted, the above discussion of the techniques of this disclosure references posture cones as one example of posture zones. It should be understood that the techniques of this disclosure are similarly applicable and may be modified to accommodate other shapes that can be used to define posture zones.

Figure 10A:
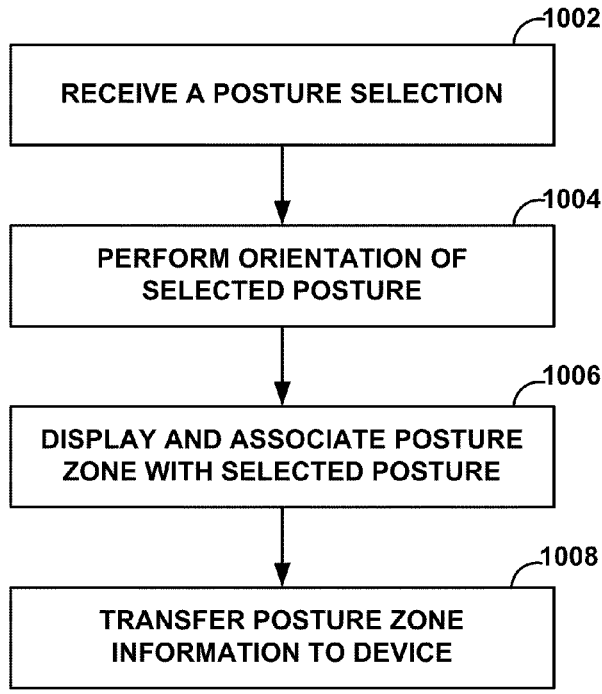
FIG. 10A is a flow diagram illustrating one example operation of a programmer device in accordance with aspects of this disclosure.

FIG. 10A is a flow diagram illustrating one example operation of a programmer device in accordance with aspects of this disclosure. A user may utilize the programmer device (e.g., programmer 20, 30, or 40) to set up the adaptive stimulation of an IMD (e.g., IMD 14 or 26) associated with a patient. The IMD may utilize adaptive stimulation to determine the therapy delivered to the patient. In one example, the therapy delivered by the IMD may be posture-dependent, where the IMD detects the posture of the patient and delivers therapy according to the detected posture. Detection of a current posture of the patient may be based on posture zones associated with the different postures, as described above. However, when the IMD is initially implanted in the a patient or if there are changes to the therapy delivered to the patient, the posture zones associated with different postures may be set up during an orientation process. To orient a posture zone, the user may utilize the programmer device to select a posture. A processor (e.g., processor 104) may receive the selected posture (1002) based on user input. The processor may also display an avatar representing the patient on a user interface of the programmer device, and may be in the selected posture (e.g., if the upright posture is selected, the avatar is displayed in an upright posture state).

While the patient is in the selected posture (e.g., upright, lying down, reclining, and so forth), the user may request, using the programmer device, orientation for the selection posture. The processor may perform orientation of the selected posture (1004), which may involve, for example, obtaining sensor information from the IMD (e.g., accelerometer data) and associating the obtained information with the selected posture. When the orientation for the selected posture is completed, the processor may display a posture zone on the user interface, and associate the posture zone with the selected posture (1006) and the obtained information. A posture zone for a selected posture may define a region relative to the patient avatar, such that, when sensor information obtained by the IMD indicate that the patient is within the posture region, then the posture of the patient is detected based on the posture regions, and the corresponding posture-based therapy is provided by the IMD. The user may repeat steps 1002 through 1006 for all desired postures, and when the user indicates completion of the orientation, the processor may transfer the information regarding the posture zones to the IMD (1008).

Figure 10B:
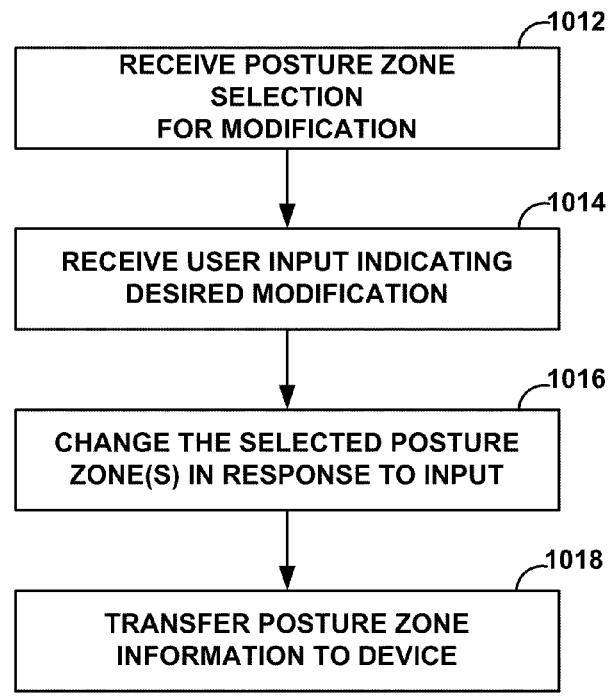
FIG. 10B is a flow diagram illustrating another example operation of a programmer device in accordance with aspects of this disclosure.

FIG. 10B is a flow diagram illustrating another example operation of a programmer device in accordance with aspects of this disclosure. Following orientation or at a subsequent time, the user may wish to manipulate the posture zones. During orientation, default posture zones may be associated with the corresponding postures. Additionally, default timing parameters (e.g., transition times) may be associated with the postures and the transitions between different postures, as discussed above. However, a user may wish to manipulate (e.g., modify) the posture zones and/or the timing parameters to accommodate different factors. For example, the size of the default posture zones may not be suitable for the size of the patient, and the user may wish to increase or decrease the size of the posture zones. The user may utilize a programmer device (e.g., programmer 30, 40, or 50) to select a desired posture zone for modification. A processor (e.g., processor 104) may receive the selected posture zone (1012). The user selection may indicate one posture zone or two posture zones to be modified. When one posture zone is selected, the modification may be a manipulation of properties of the posture zone (e.g., size change). If two posture zones are selected, the modification may be a manipulation of timing parameters associated with the posture zones (e.g., transition time change). The processor may receive user input via the user interface (e.g., user interface 106) indicating the desired modification to one or more parameters associated with the posture zone (1014), as described above. The processor may then change the selected one or more posture zones in response to the user input (1016). The user may repeat steps 1012 through 1016 for any one or more posture zones, and when completed, the processor may transfer the modified posture zone information to the IMD (1018).

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to support one or more aspects of the functionality described in this disclosure.

In addition, it should be noted that the systems described herein may not be limited to treatment of a human patient. In alternative examples, these systems may be implemented in non-human patients, e.g., primates, canines, equines, pigs, and felines. These animals may undergo clinical or research therapies that my benefit from the subject matter of this disclosure.

Many examples of the disclosure have been described. Various modifications may be made without departing from the scope of the claims. These and other examples are within the scope of the following claims.

The invention claimed is:

1. A method comprising:
controlling delivery of therapy from a medical device to a patient based on a detected posture state of the patient, wherein the medical device is configured to detect the posture state of the patient based on a comparison of a posture sensor output to one or more posture zones;
displaying a graphical representation of the one or more posture zones associated with the patient on a display device, wherein the display device is configured to be communicatively coupled to the medical device;
receiving user input via a user interface while the display device simultaneously displays the graphical representation of the one or more posture zones associated with the patient, wherein the user input comprises an indication to change one or more parameters associated with the one or more posture zones; and
changing the one or more parameters associated with the one or more posture zones in response to the user input, wherein the receiving and changing are performed via a processor.

2. The method of claim 1, wherein the indication comprises an indication to change the size of at least one of the one or more posture zones, the method further comprising:
changing the size of the at least one of the one or more posture zones according to the indication.

3. The method of claim 1, further comprising displaying an avatar of the patient in relation to the graphical representation of the one or more posture zones.

4. The method of claim 1, wherein the graphical representation comprises a graphical representation of at least one cone corresponding to the one or more posture zones.

5. The method of claim 4, further comprising changing an angle associated with the cone relative to a center vector passing through a center of the cone in response to the user input.

6. The method of claim 1, further comprising:
displaying a timing parameter associated with at least one of the one or more posture zones, wherein the medical device is configured to detect the posture state of the patient based at least in part on the timing parameter, wherein the indication comprises an indication to change the timing parameter associated with the at least one of the one or more posture zones; and
changing the timing parameter associated with the at least one of the one or more posture zones based on the indication.

7. The method of claim 6, wherein the timing parameter comprise transition times associated with transitioning from a first posture state to a second posture state.

8. The method of claim 7, further comprising displaying the indication to change the timing parameter, wherein displaying the indication comprises displaying a first pattern on the graphical representation of the zone associated with the first posture state and displaying a second pattern on the graphical representation of the zone associated with the second posture state.

9. The method of claim 7, further comprising accepting the second posture state as a current posture of the patient if the patient remains in the second posture state for an amount of time equal to or greater than the transition time.

10. The method of claim 1, wherein displaying a graphical representation of posture zones comprises displaying a graphical representation of multiple postures zones of the one or more posture zones simultaneously with each other.

11. The method of claim 10, further comprising displaying an avatar of the patient in relation to the graphical representation of the multiple posture zones.

12. The method of claim 1, further comprising transmitting the change to the medical device.

13. The method of claim 1, further comprising receiving the output of the posture sensor from the medical device via a telemetry module.

14. The method of claim 1, wherein the graphical representation of the one or more posture zones is defined based on the one or more parameters associated with the one or more posture zones.

15. The method of claim 1, further comprising:
detecting the posture state of the patient based on the posture sensor output being within a zone of the one or more posture zones; and
delivering therapy to the patient via the medical device based on the detected posture state of the patient.

16. A system comprising:
means for controlling delivery of therapy from a medical device to a patient based on a detected posture state of the patient, wherein the medical device is configured to detect the posture state of the patient based on a comparison of a posture sensor output to one or more posture zones;
means for displaying a graphical representation of the one or more posture zones associated with the patient, wherein the display device is configured to be communicatively coupled to the medical device;
means for receiving user input while the means for displaying simultaneously displays the graphical representation of the one or more posture zones associated with the patient, wherein the user input comprises an indication to change one or more parameters associated with the one or more posture zones; and means for changing the one or more parameters associated with the one or more posture zones in response to the user input.

17. The system of claim 16, wherein the indication comprises an indication to change the size of at least one of the one or more posture zones, the system further comprising:

means for changing the size of the at least one of the one or more zones according to the indication.

18. The system of claim 16, further comprising means for displaying an avatar of the patient in relation to the graphical representation of the one or more posture zones.

19. The system of claim 16, wherein the graphical representation comprises a graphical representation of at least one cone corresponding to the one or more posture zones.

20. The system of claim 19, further comprising means for changing an angle associated with the cone relative to a center vector passing through a center of the cone in response to the user input.

21. The system of claim 16, further comprising:

means for displaying a timing parameter associated with at least one of the one or more posture zones, wherein the indication comprises an indication to change the timing parameter associated with the at least one of the one or more posture zones; and means for changing the timing parameter associated with the at least one of the one or more posture zones based on the indication.

22. The system of claim 21, wherein the timing parameter comprise transition times associated with transitioning from a first posture state to a second posture state.

23. The system of claim 22, further comprising means for displaying the indication to change the timing parameter, wherein the means for displaying the indication comprises means for displaying a first pattern on the graphical representation of the zone associated with the first posture state and means for displaying a second pattern on the graphical representation of the zone associated with the second posture state.

24. The system of claim 22, further comprising means for accepting the second posture state as a current posture of the patient if the patient remains in the second posture state for an amount of time equal to or greater than the transition time.

25. A non-transitory computer-readable storage medium comprising instructions that, upon execution, cause one or more processors to:

control delivery of therapy from a medical device to a patient based on a detected posture state of the patient, wherein the medical device is configured to detect the posture state of the patient based on a comparison of a posture sensor output to one or more posture zones;

display a graphical representation of the one or more posture zones associated with the patient on a display device, wherein the display device is configured to be communicatively coupled to the medical device;

receive user input while the display device simultaneously displays the graphical representation of the one or more posture zones associated with the patient, wherein the user input comprises an indication to change one or more parameters associated with the one or more posture zones; and change the one or more parameters associated with the one or more posture zones in response to the user input.

26. The computer-readable medium of claim 25, wherein the indication comprises an indication to change the size of at least one of the one or more posture zones, the computer-readable medium further comprising instructions that cause the processor to:

change the size of the at least one of the one or more posture zones according to the indication.

27. The computer-readable medium of claim 25, further comprising instructions that cause the processor to display an avatar of the patient in relation to the graphical representation of the one or more posture zones.

28. The computer-readable medium of claim 25, wherein the graphical representation comprises a graphical representation of at least one cone corresponding to the one or more posture zones.

29. The computer-readable medium of claim 28, further comprising instructions that cause the processor to change an angle associated with the cone relative to a center vector passing through a center of the cone in response to the user input.

30. The computer-readable medium of claim 25, further comprising instructions that cause the processor to:

display a timing parameter associated with at least one of the one or more posture zones, wherein the indication comprises an indication to change the timing parameter associated with the at least one of the one or more posture zones; and change the timing parameter associated with the at least one of the one or more posture zones based on the indication.

31. The computer-readable medium of claim 30, wherein the timing parameter comprises a transition time associated with transitioning from a first posture state to a second posture state.

32. The computer-readable medium of claim 31, further comprising instructions that cause the processor to display the indication to change the timing parameter, wherein the instructions to display the indication comprise instructions that cause the processor to display a first pattern on the graphical representation of the zone associated with the first posture state and display a second pattern on the graphical representation of the zone associated with the second posture state.

33. The computer-readable medium of claim 31, further comprising instructions that cause the processor to accept the second posture state as a current posture of the patient if the patient remains in the second posture state for an amount of time equal to or greater than the transition time.

34. A system comprising:

a medical device configured to deliver therapy to a patient;

a posture sensor configured to generate a posture sensor output;

a display device configured to display a graphical representation of one or more posture zones associated with a patient, wherein the display device is configured to be communicatively coupled to the medical device, wherein the medical device is configured to deliver therapy to the patient based on a detected posture state of the patient, and wherein the medical device is configured to detect the posture state of the patient based on a comparison of a posture sensor output to the one or more posture zones;

a user interface configured to receive user input, wherein the user input comprises an indication to change one or more parameters associated with the one or more posture zones, and wherein the user interface is configured to receive the user input while the display device simultaneously displays the graphical representation of the one or more posture zones associated with the patient; and a processor configured to change the one or more parameters associated with the one or more posture zones in response to the user input.

35. The system of claim 34, further comprising a programmer configured to program the medical device, wherein the programmer includes the display device, the user interface, and the processor.

36. The system of claim 34:
wherein the indication comprises an indication to change the size of at least one of the one or more posture zones, and
wherein the processor is configured to change the size of the at least one of the one or more posture zones according to the indication.

37. The system of claim 34, wherein the display device is further configured to display an avatar of the patient in relation to the graphical representation of the one or more posture zones.

38. The system of claim 34, wherein the graphical representation comprises a graphical representation of at least one cone corresponding to the one or more posture zones.

39. The system of claim 38, wherein the processor is configured to change an angle associated with the cone relative to a center vector passing through a center of the cone in response to the user input.

40. The system of claim 34,
wherein the display device is configured to display timing parameters associated with at least one of the one or more posture zones,
wherein the indication comprises an indication to change the timing parameter associated with the at least one of the one or more posture zones, and
wherein the processor is configured to change the timing parameter associated with the at least one of the one or more posture zones based on the indication.

41. The system of claim 40, wherein the timing parameters comprise transition times associated with transitioning from a first posture state to a second posture state.

42. The system of claim 41, wherein the display device is further configured to display the indication to change the timing parameter by displaying a first pattern on the graphical representation of the zone associated with the first posture state and displaying a second pattern on the graphical representation of the zone associated with the second posture state.

43. The system of claim 41, wherein the processor is further configured to accept the second posture state as a current posture state of the patient if the patient remains in the second posture state for an amount of time equal to or greater than the transition time.

44. The system of claim 34, wherein the display device is configured to display a graphical representation of multiple postures zones of the one or more posture zones simultaneously with each other.

45. The system of claim 44, wherein the display device is configured to display an avatar of the patient in relation to the graphical representation of the multiple posture zones.

46. The system of claim 34, wherein the processor is configured to transmit the change to the medical device.

47. The system of claim 34, wherein the display device includes a telemetry module configured to receive the output of the posture sensor from the medical device.

48. The system of claim 34, wherein the graphical representation of the one or more posture zones is defined based on the one or more parameters associated with the one or more posture zones.

49. The system of claim 34, wherein the medical device is configured to detect the posture state of the patient based on the posture sensor output being within a zone of the one or more posture zones, and deliver therapy to the patient via the medical device based on the detected posture state of the patient.

* * * * *

UNITED STATES PATENT AND TRADEMARK OFFICE
CERTIFICATE OF CORRECTION

PATENT NO. : 9,956,418 B2  
APPLICATION NO. : 12/986039  
DATED : May 1, 2018  
INVENTOR(S) : Davis et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 768 days.

Signed and Sealed this  
Seventh Day of February, 2023

Katherine Kelly Vidal  
*Director of the United States Patent and Trademark Office*